US005665579A

United States Patent [19]
Fitzmaurice et al.

[11] Patent Number: 5,665,579
[45] Date of Patent: Sep. 9, 1997

[54] INVERTASE GENES AND USES THEREOF

[75] Inventors: Leona C. Fitzmaurice; T. Erik Mirkov; Kathryn J. Elliott; William Owen Butler, all of San Diego, Calif.; Yoshihiro Konno, Onishi, Japan; Craig Duane Dickinson, San Diego, Calif.

[73] Assignee: The Salk Institute Biotechnology/Industrial Associates, Inc., San Diego, Calif.

[21] Appl. No.: 245,809

[22] Filed: May 17, 1994

Related U.S. Application Data

[63] Continuation of Ser. No. 771,331, Oct. 4, 1991, abandoned, which is a continuation-in-part of Ser. No. 660,344, Feb. 22, 1991, abandoned.

[51] Int. Cl.$^6$ .......................... A01H 5/00; C12N 15/29; C12N 15/82; C12N 15/56
[52] U.S. Cl. .......................... 435/172.3; 435/320.1; 435/201; 435/411; 536/23.1; 536/23.2; 536/23.6; 536/24.1; 536/24.5; 800/205; 800/DIG. 44
[58] Field of Search .......................... 435/172.3, 240.4, 435/320.1, 201; 536/23.2, 23.6, 23.7, 24.1, 24.5, 23.1; 800/205, 255, DIG. 44; 935/64

[56] References Cited

U.S. PATENT DOCUMENTS

| | | | |
|---|---|---|---|
| 4,394,443 | 7/1983 | Weissman et al. | 435/6 |
| 4,446,235 | 5/1984 | Seeburg | 435/91 |
| 4,801,540 | 1/1989 | Hiatt et al. | 435/172.3 |
| 4,943,674 | 7/1990 | Houck et al. | 800/205 |
| 5,254,800 | 10/1993 | Bird et al. | 800/205 |

FOREIGN PATENT DOCUMENTS

| | | |
|---|---|---|
| 0332104 | 9/1989 | European Pat. Off. . |
| 0442592 | 8/1991 | European Pat. Off. . |
| 8912230 | 12/1989 | WIPO . |
| 8912059 | 12/1989 | WIPO . |
| 8912386 | 12/1989 | WIPO . |
| 9306711 | 4/1993 | WIPO . |
| 9307257 | 4/1993 | WIPO . |

OTHER PUBLICATIONS

Derwent World Patents Index WPI Accession No: 91-246636, "Transgenic plants with altered habit and/or yield—containing DNA coding for products capable of altering photoassimilate distribution and/or production," to Willmitzer et al.

Chrispeels, "Sorting of protein in the secretory system," *Ann. Rev. Plant. Physiol. Plant Molec. Biol.*, 42:21-53 (1991).

Saalbach, et al., "Different legumin protein domains act as vacuolar targeting signals," *Plant Cell*, 3:695-708 (1991).

Bustos et al., "Regulation of β-glucuronidase expression in transgenic tobacco plants by an A/T-rich, cis-acting sequence found upstream of a French bean β-phaseolin gene," *Plant Cell*, 1:839-853 (1989).

Callis et al., "Introns increase gene expression in cultured maize cells," *Genes Dev.*, 1:1183-1200 (1987).

DeLoose et al., "Primary structure of a hormonally regulated β-glucanase of *Nicotiana plumbaginifolia*," *Gene*, 70:13-23 (1988).

Dean et al., "mRNA transcripts of several plant genes are polyadenylated at multiple sites in vivo," *Nucl. Acids Res.*, 14:2229-2240 (1986).

Forde et al., "Nuclear factors interact with conserved A/T-rich elements upstream of a nodule-enhanced glutamine synthetase gene from French bean," *Plant Cell*, 2:925-939 (1990).

Giaquinta et al., "Pathway of phloem unloading of sucrose in corn roots," *Plant Physiol.*, 72:362-367 (1983).

Jensen et al., "Interaction of a nodule specific, trans-acting factor with distinct DNA elements in the soybean leghaemoglobin $ibc_3$ 5' upstream region," *EMBO J.*, 7:1265-1271 (1988).

Jofuku et al., "Interaction of an embryo DNA binding protein with a soybean lectin gene upstream region," *Nature*, 328:734-737 (1987).

Joshi, C.P., "An inspection of the domain between putative TATA box and translation start site in 79 plant genes," *Nucl. Acids. Res.*, 15:6643-6653 (1987a).

Joshi, C.P., "Putative polyadenylation signals in nuclear genes of higher plants: a compilation and analysis," *Nucl. Acids Res.*, 15:9627-9640 (1987b).

Martin et al., "Characterization of the levanase gene of *Bacillus subtillis* which shows homology to yeast invertase," *Mol. Gen. Genet.*, 208:177-184 (1987).

McElroy et al., "Isolation of an efficient actin promoter for use in rice transformation," *Plant Cell*, 2:163-171 (1990).

(List continued on next page.)

*Primary Examiner*—David T. Fox
*Assistant Examiner*—Elizabeth F. McElwain
*Attorney, Agent, or Firm*—Burns, Doane, Swecker & Mathis, L.L.P.

[57] ABSTRACT

Transgenic plants that are modified to produce fruits that have altered levels of soluble solids compared to non-transgenic species of the same species are provided. The transgenic plants are modified by introduction of DNA constructs that encode invertase operatively linked to DNA encoding regulatory regions that direct transcription of the DNA encoding invertase and to DNA encoding sequences that direct proper processing of the invertase through the secretory pathways of the plant and targeting of the invertase to the vacuole.

In particular, DNA constructs encoding tomato plant vacuolar invertase in operative linkage with a developmentally regulated promoter region are provided. Preferred regulatory and structural DNA is obtained from genomic DNA clones and cDNA clones encoding tomato fruit vacuolar invertases from the commercial tomato plant, *Lycopersicon esculentum*, and wild tomato plant, *Lycopersicon pimpinellifolium*.

Probes derived from the genomic DNA and cDNA, antibodies specific for tomato fruit invertase, and uses therefore, are also provided.

17 Claims, 8 Drawing Sheets

OTHER PUBLICATIONS

Miron et al., "Sucrose phosphate synthase, sucrose synthase, and invertase activities in developing fruit of *Lycopersicon esculentum* Mill. and the sucrose accumulating *Lycopersicon hirsutum* Humb. and Bonpl., " *Plant Physiol.*, 95:623–627 (1991).

Ricardo, C.P.P., "Alkaline β-fructofuranosidases of tuberous roots: Possible physiological function," *Planta*, 118:333–343 (1974).

Ricardo et al., "Development of tuberous roots and sugar accumulation as related to invertase activity and mineral nutrition," *Planta*, 118:43–55 (1974).

von Heijne, G., "A new method for predicting signal sequence cleavage sites," *Nucl. Acids Res.*, 14:4683–4690 (1986).

Boller et al., "Hydrolytic enzymes in the central vacuole of plant cells," *Plant Physiol.*, 63:1123–1132 (1979).

Esmon et al., "Structure, assembly, and secretion of octameric invertase," *J. Biol. Chem.*, 262:4387–4394 (1987).

Iwatsubo, et al., "The development of activity of cell wall bound β-fructofuranosidase with ripening and senescence of tomato fruit," *Agr. Biol. Chem.*, 39(4):907–908 (1975).

Iwatsubo, et al., "Increase of β-fructofuranosidase content in tomato fruit during the ripening process," *Agr. Biol. Chem.*, 40(6):1243–1244 (1976).

Nakagawa, et al., "Purification and some properties of two types of β-fructofuranosidase from tomato fruit," *Agr. Biol. Chem.*, 36:18–26 (1971).

Sturm, et al., "cDNA cloning of carrot extracellular β-fructosidase and its expression in response to wounding and bacterial infection," *Plant Cell*, 2:1107–1119 (1990).

Dickinsen, et al., "Slow-growth phenotype of transgenic tomato expressing apoplastic invertase," *Plant Physiology*, 95:420–425 (1991).

Endo, et al., "Size and levels of mRNA for acid invertase in ripe tomato fruit," *Plant Cell Physiology*, 31(5):655–659 (1990).

Manning, et al., "Distribution of acid invertase in the tomato plant," *Phytochemistry*, 14:1965–1969 (1975).

Takehana, et al., "Purification of some properties of β-fructofuranosidase from tomato fruit," *Bull Fac Hort, Chiba Univ.*, 18:67–76 (1970).

Yelle, et al., "Genetic and biochemical analysis of sucrose accumulation in tomato fruit (Abstract No. 49)," *Horticultural Biotechnology Symposium, Univ. of Calif.*, Aug. 21–23 (1989).

Bracho, et al., "Purification and partial characterization of potato (*Soanum tuberosum*) invertase and its endogenous proteinaceous inhibitor," *Plant Physiology*, 92:386–394 (1990).

Faye, et al., "Evidence for the glycoprotein nature of radish β-fructosidase," *Biochimie*, 61:51–59 (1979).

Karuppiah, et al., "Purification and characterization of souble (cytosolic) and bound (cell wall) isoforms of invertases in barley (*Hordium volgare*) elongating stem tissue," *Plant Physiology*, 91:993–998 (1989).

Lauriere, et al., "Characterization of β-fructosidase, an extra–cellular glycoprotein of carrot cells," *Biochimie*, 70:1483–1491 (1988).

Leigh, et al., "The localization of acid invertase activity and sucrose in the vacuoles of storage roots of bettroot (*Beta vulgaris*)," *Biochem. J.*, 178:539–547 (1979).

Prado, et al., "Purification and characterization of *Ricinus communis* invertase," *Journal of Biological Chemistry*, 260(8):4952–4957 (1985).

von Schaewen et al., "Expression of a yeast–derived invertase in the cell wall of tobacco and *Arabidopsis* plants leads to accumulation of carbohydrate and inhibition of photosynthesis and strongly influences growth and phenotype of transgenic tobacco plants," *The EMBO Journal*, 9(10):3033–3044 (1990).

Morton, et al., "Monoclonal antibody identifies a 200–kDa subunit of the dihycropyridine–sensitive calcium channel," *Journal of Biological Chemistry*, 262(25):11904–11907 (1987).

Lichtenstein, "Anti–sense RNA as a tool to study plant gene expression," *Nature*, 333:801–802 (1988).

Crum, et al., "Complementary oligodeoxynucleotide mediated inhibition of tobacco mosaic virus RNA translation in vitro," *Nucleic Acids Research*, 16(10):4569–4581 (1988).

Bednarek, et al., "A carboxyl–terminal propeptide is necessary for proper sortin of barley lectin to vacuoles of tobacco," *Plant Cell*, 2:1145–1155 (1990).

Freeman, et al., "A comparison of methods for plasmid delivery into plant protoplasts," *Plant & Cell Physiol.*, 25(8):1353–1365 (1984).

Lorz, et al., "Gene transfer to cereal cells mediated by protoplast transformation," *Mol. Gen. Genet.*, 199:178–182 (1985).

Krens, et al., "In vitro transformation of plant protoplasts with Ti–plasmid DNA," *Nature*, 296:72–74 (1982).

Tague, et al., "A short domain of the plant vacuolar protein phytohemagglutinin targets invertase to the yeast vacuole," *Plant Cell*, 2:553–546 (1990).

Yelle, et al., "Sink metabolism in tomato fruit," *Plant Physiol.*, 95:1026–1035 (1991).

Faye, et al., "Structure, biosynthesis, and function of asparagine–linked glycans on plant glycoproteins," *Physiologia Plantarum*, 75:309–314 (1989).

Elliott, et al., "Gene regulation during fruit ripening: Cloning and characterization of tomato fruit vacuolar invertase cDNA and genomic sequences," Third Int'l Congress Plant Molec. Biol. in Tucson, AZ, Oct. 4, 1991.

Fitzmaurice, et al., "Gene Expression During Tomato Fruit Development," presented at the Tomato Biotech. Symposium, Davis, CA, Aug. 20–22, 1986.

Davies et al. "Identification of cDNA clones for tomato (*Lycopersicon esculentum* Mill.) MRNAs that accumulate during furit ripening and leaf senescence in response to ethylene", *Planta* 179:73–80 (1989).

Gray et al., "Molecular biology of fruit ripening and its maipulation with antisense genes", *Plant Molecular Biology* 19:69–87 (1992).

Goldenberg et al 1966 Bol. Genetico 2(pp. 1 and 9; Table 7).

Atanassoi 1983 In Handbook of Plant Cell Culture vol 4; Evans et al (ed.); MacMillan Publ. Co. pp. 652–653 and 664–665.

Shahin 1984 In Cell Culture and Sonatic Cell Genetics of Plants vol 1; Vasil Ed.; Academic Press pp. 370–371.

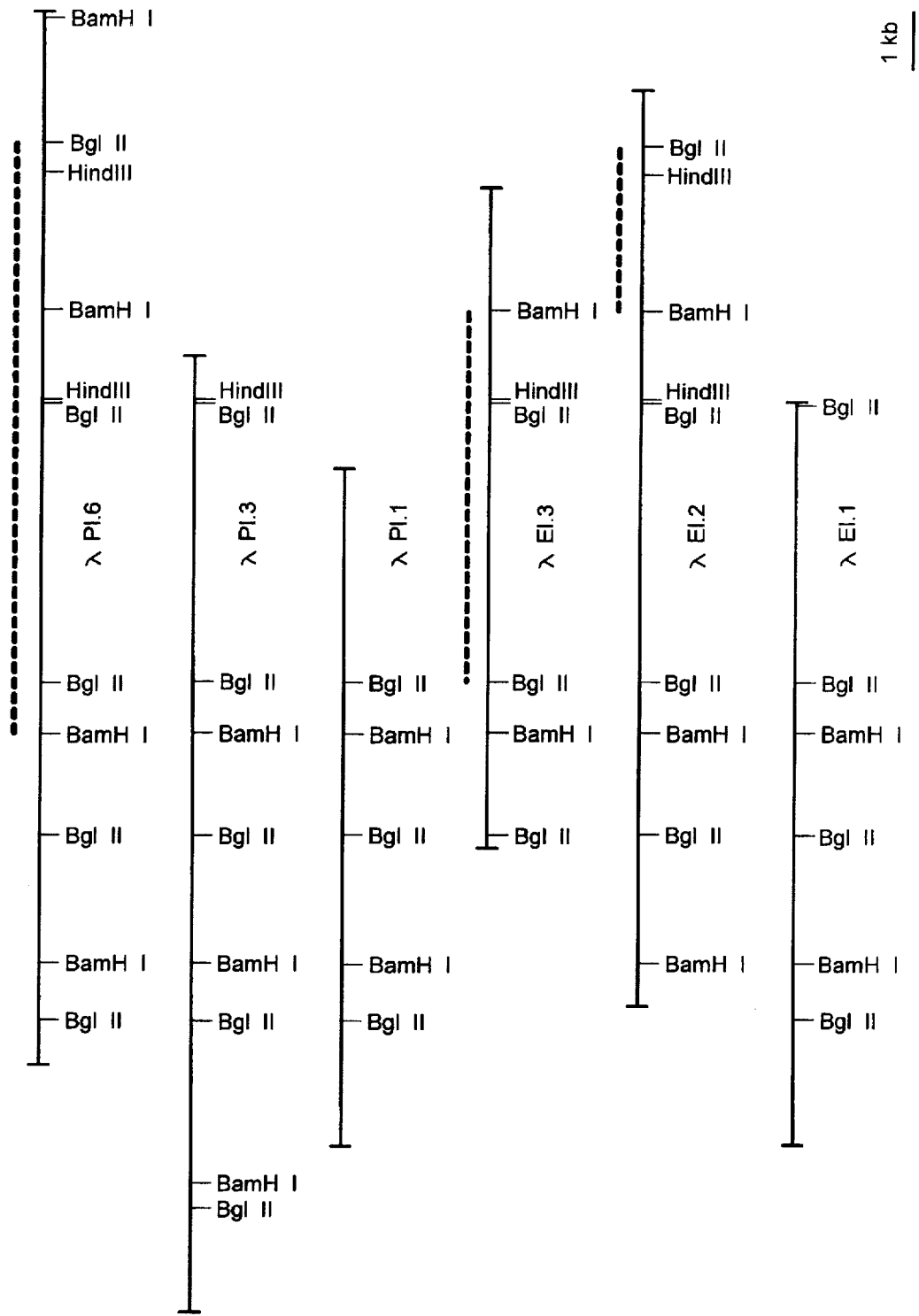
FIG. 1 RESTRICTION ENZYME MAPS OF INVERTASE GENOMIC CLONES

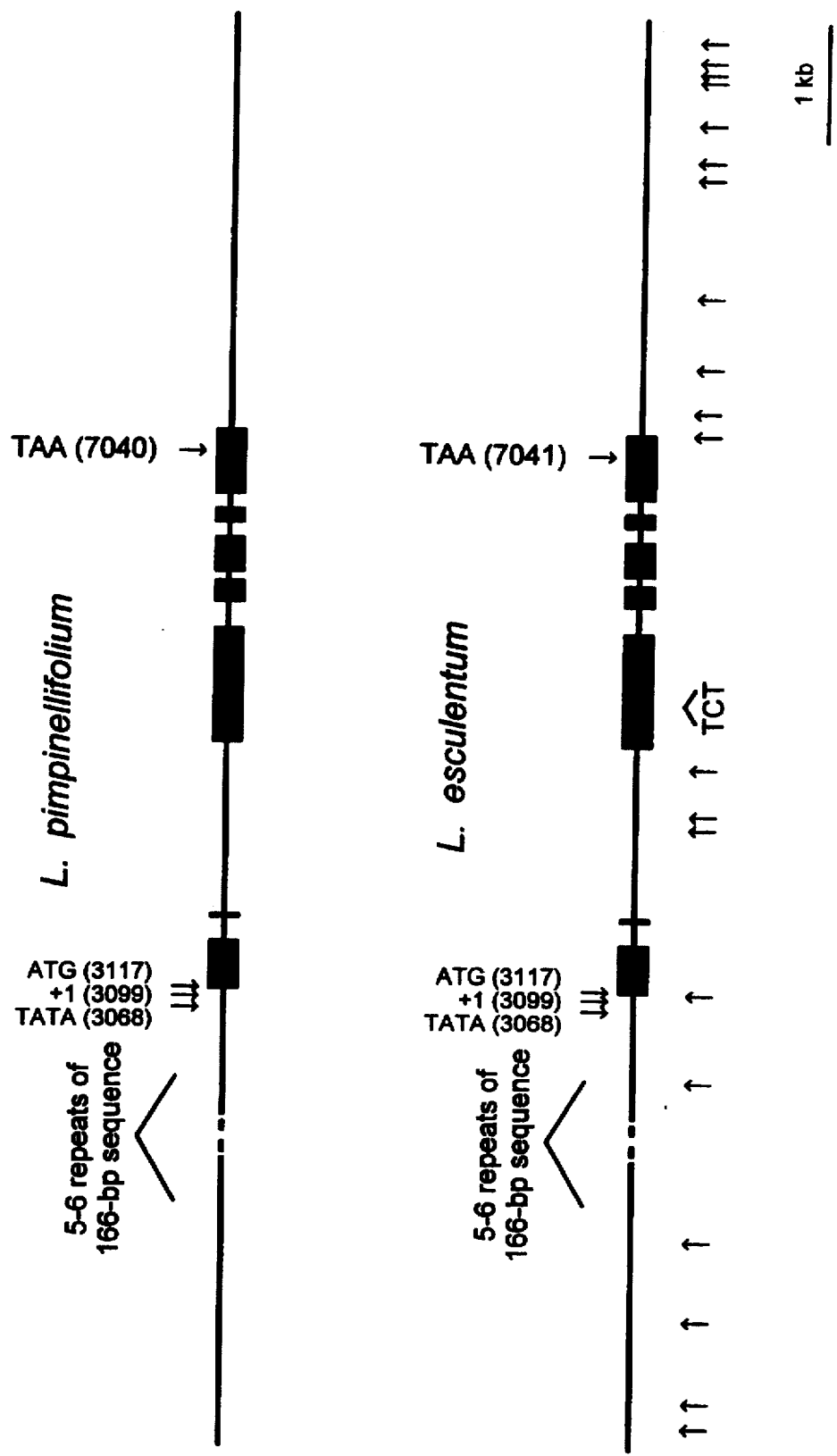
FIG. 2 SCHEMATIC OF INVERTASE GENOMIC CLONES

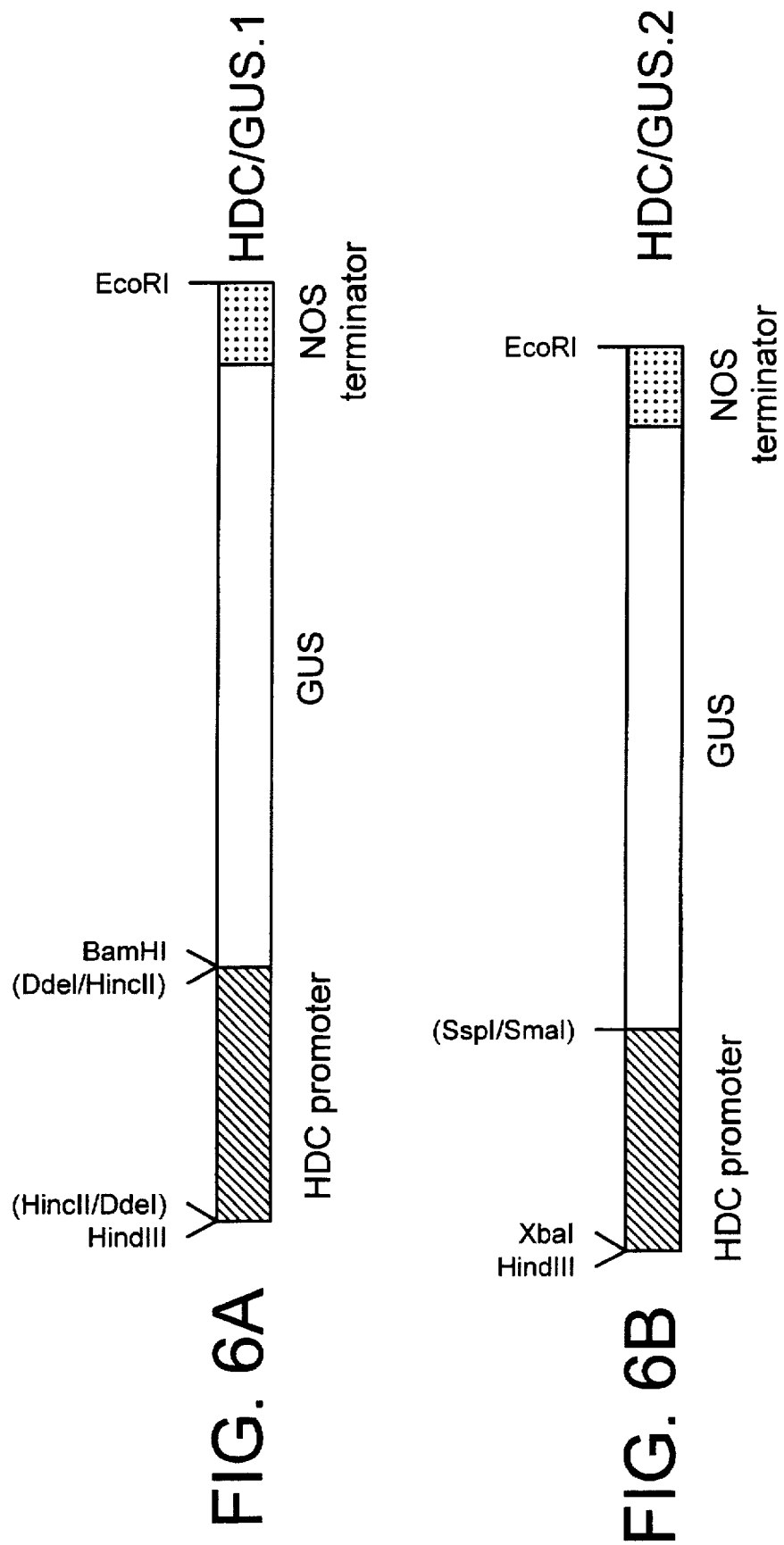

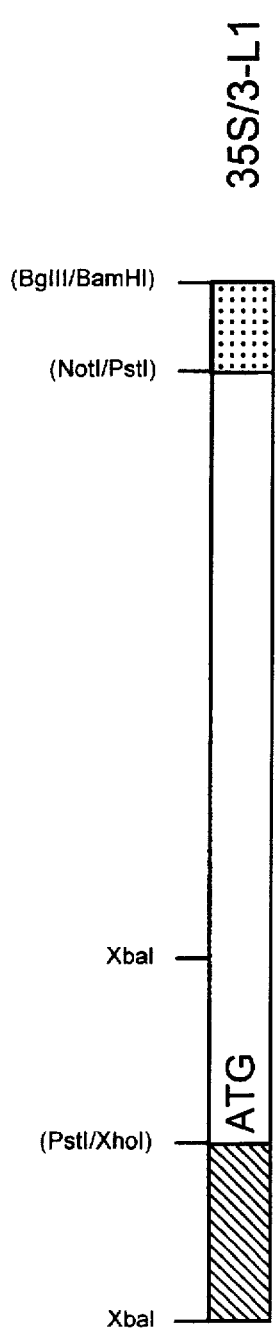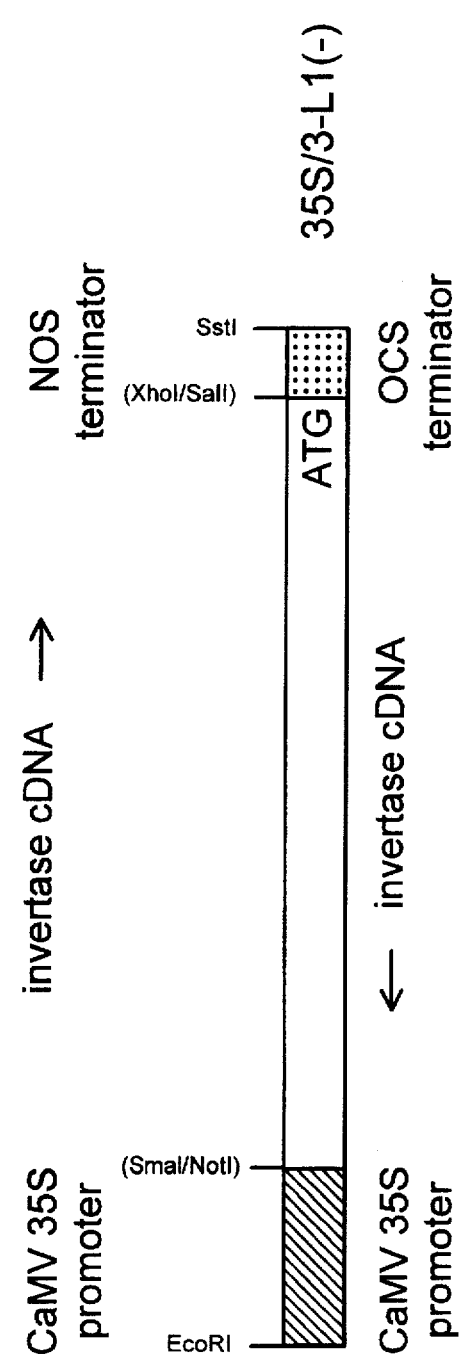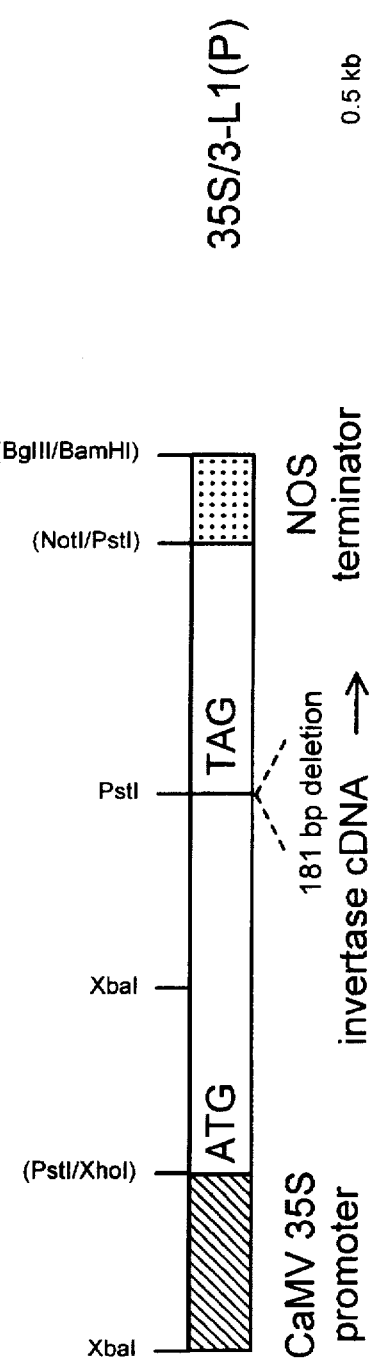

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
        ( A ) LENGTH: 635 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Met Ala Thr Gln Cys Tyr Asp Pro Glu Asn Ser Ala Ser Arg Tyr Thr
 1               5                  10                  15

Leu Leu Pro Asp Gln Pro Asp Ser Gly His Arg Lys Ser Leu Lys Ile
            20                  25                  30

Ile Ser Gly Ile Phe Leu Ser Val Phe Leu Leu Leu Ser Val Ala Phe
        35                  40                  45
```

```
Phe Pro Ile Leu Asn Asn Gln Ser Pro Asp Leu Gln Ile Asp Ser Arg
    50              55                  60
Ser Pro Ala Pro Pro Ser Arg Gly Val Ser Gln Gly Val Ser Asp Lys
 65             70              75                          80
Thr Phe Arg Asp Val Ala Gly Ala Ser His Val Ser Tyr Ala Trp Ser
                85                  90                      95
Asn Ala Met Leu Ser Trp Gln Arg Thr Ala Tyr His Phe Gln Pro Gln
            100                 105                 110
Lys Asn Trp Met Asn Asp Pro Asn Gly Pro Leu Tyr His Lys Gly Trp
        115                 120                 125
Tyr His Leu Phe Tyr Gln Tyr Asn Pro Asp Ser Ala Ile Trp Gly Asn
    130             135                 140
Ile Thr Trp Gly His Ala Val Ser Lys Asp Leu Ile His Trp Leu Tyr
145             150                 155                     160
Leu Pro Phe Ala Met Val Pro Asp Gln Trp Tyr Asp Ile Asn Gly Val
                165                 170                 175
Trp Thr Gly Ser Ala Thr Ile Leu Pro Asp Gly Gln Ile Met Met Leu
            180                 185                 190
Tyr Thr Gly Asp Thr Asp Asp Tyr Val Gln Val Gln Asn Leu Ala Tyr
        195                 200                 205
Pro Ala Asn Leu Ser Asp Pro Leu Leu Asp Trp Val Lys Phe Lys Gly
    210             215                 220
Asn Pro Val Leu Val Pro Pro Gly Ile Gly Val Lys Asp Phe Arg
225             230                 235                     240
Asp Pro Thr Thr Ala Trp Thr Gly Pro Gln Asn Gly Gln Trp Leu Leu
                245                 250                 255
Thr Ile Gly Ser Lys Ile Gly Lys Thr Gly Val Ala Leu Val Tyr Glu
            260                 265                 270
Thr Ser Asn Phe Thr Ser Phe Lys Leu Leu Asp Gly Val Leu His Ala
        275                 280                 285
Val Pro Gly Thr Gly Met Trp Glu Cys Val Asp Phe Tyr Pro Val Ser
    290             295                 300
Thr Lys Lys Thr Asn Gly Leu Asp Thr Ser Tyr Asn Gly Pro Gly Val
305             310                 315                     320
Lys His Val Leu Lys Ala Ser Leu Asp Asp Asn Lys Gln Asp His Tyr
                325                 330                 335
Ala Ile Gly Thr Tyr Asp Leu Gly Lys Asn Lys Trp Thr Pro Asp Asn
            340                 345                 350
Pro Glu Leu Asp Cys Gly Ile Gly Leu Arg Leu Asp Tyr Gly Lys Tyr
        355                 360                 365
Tyr Ala Ser Lys Thr Phe Tyr Asp Pro Lys Lys Glu Arg Arg Val Leu
    370             375                 380
Trp Gly Trp Ile Gly Glu Thr Asp Ser Glu Ser Ala Asp Leu Gln Lys
385             390                 395                     400
Gly Trp Ala Ser Val Gln Ser Ile Pro Arg Thr Val Leu Tyr Asp Lys
                405                 410                 415
Lys Thr Gly Thr His Leu Leu Gln Trp Pro Val Glu Glu Ile Glu Ser
            420                 425                 430
Leu Arg Val Gly Asp Pro Thr Val Lys Gln Val Asp Leu Gln Pro Gly
        435                 440                 445
Ser Ile Glu Leu Leu Arg Val Asp Ser Ala Ala Glu Leu Asp Ile Glu
    450             455                 460
Ala Ser Phe Glu Val Asp Lys Val Ala Leu Gln Gly Ile Ile Glu Ala
```

```
465                          470                          475                          480
Asp  His  Val  Gly  Phe  Ser  Cys  Ser  Thr  Ser  Gly  Gly  Ala  Ala  Ser  Arg
                    485                      490                          495

Gly  Ile  Leu  Gly  Pro  Phe  Gly  Val  Ile  Val  Ile  Ala  Asp  Gln  Thr  Leu
               500                      505                     510

Ser  Glu  Leu  Thr  Pro  Val  Tyr  Phe  Tyr  Ile  Ser  Lys  Gly  Ala  Asp  Gly
               515                      520                     525

Arg  Ala  Glu  Thr  His  Phe  Cys  Ala  Asp  Gln  Thr  Arg  Ser  Ser  Glu  Ala
     530                         535                     540

Pro  Gly  Val  Gly  Lys  Gln  Val  Tyr  Gly  Ser  Ser  Val  Pro  Val  Leu  Asp
545                      550                     555                          560

Gly  Glu  Lys  His  Ser  Met  Arg  Leu  Leu  Val  Asp  His  Ser  Ile  Val  Glu
                    565                      570                          575

Ser  Phe  Ala  Gln  Gly  Gly  Arg  Thr  Val  Ile  Thr  Ser  Arg  Ile  Tyr  Pro
               580                      585                     590

Thr  Lys  Ala  Val  Asn  Gly  Ala  Ala  Arg  Leu  Phe  Val  Phe  Asn  Asn  Ala
               595                 600                     605

Thr  Gly  Ala  Ser  Val  Thr  Ala  Ser  Val  Lys  Ile  Trp  Ser  Leu  Glu  Ser
     610                    615                     620

Ala  Asn  Ile  Gln  Ser  Phe  Pro  Leu  Gln  Asp  Leu
625                      630                     635
```

( 2 ) INFORMATION FOR SEQ ID NO:2:

( i ) SEQUENCE CHARACTERISTICS:
    ( A ) LENGTH: 2196 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 7..1914
    ( D ) OTHER INFORMATION: /product="L. esculentum vacuolar invertase"

( x i ) SEQUENCE DESCRIPTION: SEQ ID NO:2:

```
TCTATT ATG GCC ACT CAG TGT TAT GAC CCC GAA AAC TCC GCC TCT CGT                48
       Met Ala Thr Gln Cys Tyr Asp Pro Glu Asn Ser Ala Ser Arg
       1               5                   10

TAC ACA TTA CTC CCG GAT CAA CCC GAT TCC GGC CAC CGG AAG TCC CTT              96
Tyr Thr Leu Leu Pro Asp Gln Pro Asp Ser Gly His Arg Lys Ser Leu
15              20                  25                      30

AAA ATC ATC TCC GGC ATT TTC CTC TCC GTT TTC CTT TTG CTT TCT GTA             144
Lys Ile Ile Ser Gly Ile Phe Leu Ser Val Phe Leu Leu Leu Ser Val
                35                  40                      45

GCC TTC TTT CCG ATC CTC AAC AAC CAG TCA CCG GAC TTG CAA ATC GAC             192
Ala Phe Phe Pro Ile Leu Asn Asn Gln Ser Pro Asp Leu Gln Ile Asp
            50                  55                      60

TCC CGT TCG CCG GCG CCG CCG TCA AGA GGT GTT TCT CAG GGA GTC TCC             240
Ser Arg Ser Pro Ala Pro Pro Ser Arg Gly Val Ser Gln Gly Val Ser
        65                  70                      75

GAT AAA ACT TTT CGA GAT GTA GCC GGT GCT AGT CAC GTT TCT TAT GCG             288
Asp Lys Thr Phe Arg Asp Val Ala Gly Ala Ser His Val Ser Tyr Ala
    80                  85                      90

TGG TCC AAT GCT ATG CTT AGC TGG CAA AGA ACG GCT TAC CAT TTT CAA             336
Trp Ser Asn Ala Met Leu Ser Trp Gln Arg Thr Ala Tyr His Phe Gln
95                  100                     105                     110

CCT CAA AAA AAT TGG ATG AAC GAT CCT AAT GGA CCA TTG TAT CAC AAG             384
```

-continued

| | | | | | | | | | | | | | | | | |
|---|---|---|---|---|---|---|---|---|---|---|---|---|---|---|---|---|
| Pro | Gln | Lys | Asn | Trp | Met | Asn | Asp | Pro | Asn | Gly | Pro | Leu | Tyr | His | Lys | |
| | | | | 115 | | | | 120 | | | | | | 125 | | |
| GGA | TGG | TAC | CAC | CTT | TTT | TAT | CAA | TAC | AAT | CCA | GAT | TCA | GCT | ATT | TGG | 432 |
| Gly | Trp | Tyr | His | Leu | Phe | Tyr | Gln | Tyr | Asn | Pro | Asp | Ser | Ala | Ile | Trp | |
| | | | 130 | | | | | 135 | | | | | 140 | | | |
| GGA | AAT | ATC | ACA | TGG | GGC | CAT | GCT | GTA | TCC | AAG | GAC | TTG | ATC | CAC | TGG | 480 |
| Gly | Asn | Ile | Thr | Trp | Gly | His | Ala | Val | Ser | Lys | Asp | Leu | Ile | His | Trp | |
| | | 145 | | | | | 150 | | | | | 155 | | | | |
| CTC | TAC | TTG | CCT | TTT | GCC | ATG | GTT | CCT | GAT | CAA | TGG | TAT | GAT | ATT | AAC | 528 |
| Leu | Tyr | Leu | Pro | Phe | Ala | Met | Val | Pro | Asp | Gln | Trp | Tyr | Asp | Ile | Asn | |
| 160 | | | | | 165 | | | | | 170 | | | | | | |
| GGT | GTC | TGG | ACA | GGG | TCC | GCT | ACC | ATC | CTA | CCC | GAT | GGT | CAG | ATC | ATG | 576 |
| Gly | Val | Trp | Thr | Gly | Ser | Ala | Thr | Ile | Leu | Pro | Asp | Gly | Gln | Ile | Met | |
| 175 | | | | | 180 | | | | | 185 | | | | | 190 | |
| ATG | CTT | TAT | ACC | GGT | GAC | ACT | GAT | GAT | TAT | GTG | CAA | GTG | CAA | AAT | CTT | 624 |
| Met | Leu | Tyr | Thr | Gly | Asp | Thr | Asp | Asp | Tyr | Val | Gln | Val | Gln | Asn | Leu | |
| | | | | 195 | | | | 200 | | | | | 205 | | | |
| GCG | TAC | CCC | GCC | AAC | TTA | TCT | GAT | CCC | CTT | CTA | GAC | TGG | GTC | AAG | TTC | 672 |
| Ala | Tyr | Pro | Ala | Asn | Leu | Ser | Asp | Pro | Leu | Leu | Asp | Trp | Val | Lys | Phe | |
| | | | 210 | | | | | 215 | | | | | 220 | | | |
| AAA | GGC | AAC | CCG | GTT | CTG | GTT | CCT | CCA | CCC | GGC | ATT | GGT | GTC | AAG | GAC | 720 |
| Lys | Gly | Asn | Pro | Val | Leu | Val | Pro | Pro | Pro | Gly | Ile | Gly | Val | Lys | Asp | |
| | | 225 | | | | | 230 | | | | | 235 | | | | |
| TTT | AGA | GAC | CCG | ACT | ACT | GCT | TGG | ACC | GGA | CCA | CAA | AAT | GGG | CAA | TGG | 768 |
| Phe | Arg | Asp | Pro | Thr | Thr | Ala | Trp | Thr | Gly | Pro | Gln | Asn | Gly | Gln | Trp | |
| 240 | | | | | 245 | | | | | 250 | | | | | | |
| CTG | TTA | ACA | ATC | GGG | TCT | AAG | ATT | GGT | AAA | ACG | GGT | GTT | GCA | CTT | GTT | 816 |
| Leu | Leu | Thr | Ile | Gly | Ser | Lys | Ile | Gly | Lys | Thr | Gly | Val | Ala | Leu | Val | |
| 255 | | | | | 260 | | | | | 265 | | | | | 270 | |
| TAT | GAA | ACT | TCC | AAC | TTC | ACA | AGC | TTT | AAG | CTA | TTG | GAT | GGA | GTG | CTG | 864 |
| Tyr | Glu | Thr | Ser | Asn | Phe | Thr | Ser | Phe | Lys | Leu | Leu | Asp | Gly | Val | Leu | |
| | | | | 275 | | | | 280 | | | | | 285 | | | |
| CAT | GCG | GTT | CCG | GGT | ACG | GGT | ATG | TGG | GAG | TGT | GTG | GAC | TTT | TAC | CCG | 912 |
| His | Ala | Val | Pro | Gly | Thr | Gly | Met | Trp | Glu | Cys | Val | Asp | Phe | Tyr | Pro | |
| | | | 290 | | | | | 295 | | | | | 300 | | | |
| GTA | TCT | ACT | AAA | AAA | ACA | AAC | GGG | TTG | GAC | ACA | TCA | TAT | AAC | GGG | CCG | 960 |
| Val | Ser | Thr | Lys | Lys | Thr | Asn | Gly | Leu | Asp | Thr | Ser | Tyr | Asn | Gly | Pro | |
| | | 305 | | | | | 310 | | | | | 315 | | | | |
| GGT | GTA | AAG | CAT | GTG | TTA | AAA | GCA | AGT | TTA | GAT | GAC | AAT | AAG | CAA | GAT | 1008 |
| Gly | Val | Lys | His | Val | Leu | Lys | Ala | Ser | Leu | Asp | Asp | Asn | Lys | Gln | Asp | |
| 320 | | | | | 325 | | | | | 330 | | | | | | |
| CAT | TAT | GCT | ATT | GGT | ACG | TAT | GAC | TTG | GGA | AAG | AAC | AAA | TGG | ACA | CCC | 1056 |
| His | Tyr | Ala | Ile | Gly | Thr | Tyr | Asp | Leu | Gly | Lys | Asn | Lys | Trp | Thr | Pro | |
| 335 | | | | | 340 | | | | | 345 | | | | | 350 | |
| GAT | AAC | CCG | GAA | TTG | GAT | TGT | GGA | ATT | GGG | TTG | AGA | CTA | GAC | TAT | GGG | 1104 |
| Asp | Asn | Pro | Glu | Leu | Asp | Cys | Gly | Ile | Gly | Leu | Arg | Leu | Asp | Tyr | Gly | |
| | | | | 355 | | | | 360 | | | | | 365 | | | |
| AAA | TAT | TAT | GCA | TCA | AAG | ACT | TTT | TAT | GAC | CCG | AAG | AAA | GAA | CGA | AGA | 1152 |
| Lys | Tyr | Tyr | Ala | Ser | Lys | Thr | Phe | Tyr | Asp | Pro | Lys | Lys | Glu | Arg | Arg | |
| | | | 370 | | | | | 375 | | | | | 380 | | | |
| GTA | CTG | TGG | GGA | TGG | ATT | GGG | GAA | ACT | GAC | AGT | GAA | TCT | GCT | GAC | CTG | 1200 |
| Val | Leu | Trp | Gly | Trp | Ile | Gly | Glu | Thr | Asp | Ser | Glu | Ser | Ala | Asp | Leu | |
| | | 385 | | | | | 390 | | | | | 395 | | | | |
| CAG | AAG | GGA | TGG | GCA | TCT | GTA | CAG | AGT | ATT | CCA | AGG | ACA | GTG | CTT | TAC | 1248 |
| Gln | Lys | Gly | Trp | Ala | Ser | Val | Gln | Ser | Ile | Pro | Arg | Thr | Val | Leu | Tyr | |
| 400 | | | | | 405 | | | | | 410 | | | | | | |
| GAC | AAG | AAG | ACA | GGG | ACA | CAT | CTA | CTT | CAG | TGG | CCA | GTG | GAA | GAA | ATT | 1296 |
| Asp | Lys | Lys | Thr | Gly | Thr | His | Leu | Leu | Gln | Trp | Pro | Val | Glu | Glu | Ile | |
| 415 | | | | | 420 | | | | | 425 | | | | | 430 | |
| GAA | AGC | TTA | AGA | GTG | GGT | GAT | CCT | ACT | GTT | AAG | CAA | GTC | GAT | CTT | CAA | 1344 |

|     |     |     |     |     |     |     |     |     |     |     |     |     |     |     |      |
| --- | --- | --- | --- | --- | --- | --- | --- | --- | --- | --- | --- | --- | --- | --- | ---- |
| Glu | Ser | Leu | Arg | Val<br>435 | Gly | Asp | Pro | Thr | Val<br>440 | Lys | Gln | Val | Asp | Leu<br>445 | Gln  |
| CCA<br>Pro | GGC<br>Gly | TCA<br>Ser | ATT<br>Ile<br>450 | GAG<br>Glu | CTA<br>Leu | CTC<br>Leu | CGT<br>Arg | GTT<br>Val<br>455 | GAC<br>Asp | TCA<br>Ser | GCT<br>Ala | GCA<br>Ala | GAG<br>Glu<br>460 | TTG<br>Leu | GAT<br>Asp | 1392 |
| ATA<br>Ile | GAA<br>Glu<br>465 | GCC<br>Ala | TCA<br>Ser | TTT<br>Phe | GAA<br>Glu | GTG<br>Val | GAC<br>Asp<br>470 | AAA<br>Lys | GTC<br>Val | GCG<br>Ala | CTT<br>Leu | CAG<br>Gln<br>475 | GGA<br>Gly | ATA<br>Ile | ATT<br>Ile | 1440 |
| GAA<br>Glu | GCA<br>Ala<br>480 | GAT<br>Asp | CAT<br>His | GTA<br>Val | GGT<br>Gly | TTC<br>Phe<br>485 | AGT<br>Ser | TGC<br>Cys | TCT<br>Ser | ACT<br>Thr | AGT<br>Ser<br>490 | GGA<br>Gly | GGT<br>Gly | GCT<br>Ala | GCT<br>Ala | 1488 |
| AGC<br>Ser<br>495 | AGA<br>Arg | GGC<br>Gly | ATT<br>Ile | TTG<br>Leu | GGA<br>Gly<br>500 | CCA<br>Pro | TTT<br>Phe | GGT<br>Gly | GTC<br>Val | ATA<br>Ile<br>505 | GTA<br>Val | ATT<br>Ile | GCT<br>Ala | GAT<br>Asp | CAA<br>Gln<br>510 | 1536 |
| ACG<br>Thr | CTA<br>Leu | TCT<br>Ser | GAG<br>Glu | CTA<br>Leu<br>515 | ACG<br>Thr | CCA<br>Pro | GTT<br>Val | TAC<br>Tyr | TTT<br>Phe<br>520 | TAC<br>Tyr | ATT<br>Ile | TCT<br>Ser | AAA<br>Lys | GGA<br>Gly<br>525 | GCT<br>Ala | 1584 |
| GAT<br>Asp | GGT<br>Gly | CGT<br>Arg | GCA<br>Ala<br>530 | GAG<br>Glu | ACT<br>Thr | CAC<br>His | TTC<br>Phe | TGT<br>Cys<br>535 | GCT<br>Ala | GAT<br>Asp | CAA<br>Gln | ACT<br>Thr | AGA<br>Arg<br>540 | TCC<br>Ser | TCT<br>Ser | 1632 |
| GAG<br>Glu | GCT<br>Ala | CCG<br>Pro<br>545 | GGA<br>Gly | GTT<br>Val | GGT<br>Gly | AAA<br>Lys | CAA<br>Gln<br>550 | GTT<br>Val | TAT<br>Tyr | GGT<br>Gly | AGT<br>Ser | TCA<br>Ser<br>555 | GTA<br>Val | CCT<br>Pro | GTG<br>Val | 1680 |
| TTG<br>Leu | GAC<br>Asp<br>560 | GGT<br>Gly | GAA<br>Glu | AAA<br>Lys | CAT<br>His | TCA<br>Ser<br>565 | ATG<br>Met | AGA<br>Arg | TTA<br>Leu | TTG<br>Leu | GTG<br>Val<br>570 | GAT<br>Asp | CAC<br>His | TCA<br>Ser | ATT<br>Ile | 1728 |
| GTG<br>Val<br>575 | GAG<br>Glu | AGC<br>Ser | TTT<br>Phe | GCT<br>Ala | CAA<br>Gln<br>580 | GGA<br>Gly | GGA<br>Gly | AGA<br>Arg | ACA<br>Thr | GTC<br>Val<br>585 | ATA<br>Ile | ACA<br>Thr | TCG<br>Ser | CGA<br>Arg | ATT<br>Ile<br>590 | 1776 |
| TAC<br>Tyr | CCA<br>Pro | ACA<br>Thr | AAG<br>Lys | GCA<br>Ala<br>595 | GTA<br>Val | AAT<br>Asn | GGA<br>Gly | GCA<br>Ala | GCA<br>Ala<br>600 | CGA<br>Arg | CTC<br>Leu | TTT<br>Phe | GTT<br>Val | TTC<br>Phe<br>605 | AAC<br>Asn | 1824 |
| AAT<br>Asn | GCC<br>Ala | ACA<br>Thr | GGG<br>Gly<br>610 | GCT<br>Ala | AGC<br>Ser | GTT<br>Val | ACT<br>Thr | GCC<br>Ala<br>615 | TCC<br>Ser | GTC<br>Val | AAG<br>Lys | ATT<br>Ile | TGG<br>Trp<br>620 | TCA<br>Ser | CTT<br>Leu | 1872 |
| GAG<br>Glu | TCA<br>Ser | GCT<br>Ala<br>625 | AAT<br>Asn | ATT<br>Ile | CAA<br>Gln | TCC<br>Ser | TTC<br>Phe<br>630 | CCT<br>Pro | TTG<br>Leu | CAA<br>Gln | GAC<br>Asp | TTG<br>Leu<br>635 | TAATCTTCTT |     |     | 1921 |

| | | | | | |
|---|---|---|---|---|---|
| TATTTCGTTT | TTTTTTTCTT | TTTCATTTGA | AGGTTATTTC | ACCGACGTCC | CATCAAGAAA | 1981 |
| GGGAAGAGGG | AGATCAATAT | ATGTAGTGTT | ATTCGCCCTA | CCTTAGGATT | AGATGTCATC | 2041 |
| TAGCAATGTC | AAATCTAGTA | GAGTATACAA | TGTATGGGTT | CCTGGAAACC | GAGTAGAGCT | 2101 |
| TACCTGGATT | CTATGTAAAC | TAAGAAAGCT | CAGCAAATAT | ATGCACAAAT | AATTTACAGA | 2161 |
| AACAACTTGG | GAATGTTGAC | AAAAAAAAAA | AAAAA | | | 2196 |

( 2 ) INFORMATION FOR SEQ ID NO:3:

( i ) SEQUENCE CHARACTERISTICS:
        ( A ) LENGTH: 10395 base pairs
        ( B ) TYPE: nucleic acid
        ( C ) STRANDEDNESS: double
        ( D ) TOPOLOGY: unknown ( i i ) MOLECULE TYPE: DNA (genomic)

( v i ) ORIGINAL SOURCE:
        ( A ) ORGANISM: Lycopersicon esculentum ( i x ) FEATURE:
        ( A ) NAME/KEY: misc_feature
        ( B ) LOCATION: 2166
        ( D ) OTHER INFORMATION: /note= "N represents approximately
        0.2 kb of missing sequence in the repetitive DNA region."

( i x ) FEATURE:
    ( A ) NAME/KEY: prim_transcript
    ( B ) LOCATION: 3117..7042

( x i ) SEQUENCE DESCRIPTION: SEQ ID NO:3:

```
GATCTCGATA  AGTTATGTCT  TGTTGGAATC  GATATCAAAT  AACCGTCGAC  GGTATCTTTG     60
ATATGAGGTA  GCGCTCAATG  ATATAAATTG  TGATGAGGAT  CTTGAATTCA  AATCTGTCAT    120
ATAGTGTGAA  CAGATAAATG  GTTAGCCAAG  TAAAATGCAC  AATTCAAGTA  TATTTTGTTT    180
CACTTAGAAA  AGTGACATTT  TGGACTGGTA  GTCCATAAAT  CAAGGTATAA  TGTCAGTGGG    240
GTACAAATAA  ATTATTATGT  GATAGTATAA  CCGTAAGATA  TCAAATACGG  TTTGTGCCTT    300
GGGGCATAAA  GGTTTATCGC  AAAAATCCTG  ACATTATTGG  AGATGTTTTC  TCCTTTGGTG    360
GATGCAATGA  GGTTTGTTTT  GATCTGGCAA  CATATGAAAA  ACTTGAATGC  ATGTAATGAA    420
AAATTGTAAT  GAAGGTTATA  TGAAAATCCT  TGAAACAATC  CAGGTGTCTG  AAGCATATAA    480
AGGTTGAAAG  AAACTTATCC  AATAAAGCTT  CAAGAATCCT  TATATGGATT  GAAATAGTCA    540
AGGAAGAAAA  AGGGTACAAA  AGAATGACCC  TAATTGTCCT  TGTATTTTA   TGAAAAGGTC    600
TTGGTAAGAC  AAAATTTTGT  CTTGACCTAC  AGATTGTTAA  TTTGACAAAT  AAAATATTTG    660
TCTAACAGAC  AACAGTGCAC  ATACACTGAA  AAATTTGAT   GCAATTTAT   GTGGATATAT    720
CGCATTCATT  GAGTACCCCA  ATGATTATGA  GATCACTTGA  CATAAATGAT  GATTCAGTTT    780
GATCTCAAAA  GAAGGATAAG  AGTTTCTTGG  TGATGAAACT  CTATCTTGGT  GCAATGAGGG    840
CACTAGTGCA  TCTTACTAAC  AATATTTGAC  TAGATATTTG  TTTTGCAGTA  AATTTACTGG    900
CAAGATTCAG  TTTCTCCCCG  ATAAAGGAC   ATTGAAATGG  TGTTGAGCAC  ATGAATGAAT    960
ATCCTCAAAG  GACCATAGTT  ATGGGTTTAT  TCTATCCCGA  GGAATCCAAG  ACAAAATTGA   1020
TTGATTACGC  AGATGCAGAA  TATTTATCTG  ATCCGCATAA  AGCTCTATCT  CAAGCACGCT   1080
ATGTGTTTGC  ATGTGGAGGC  ACAATAATAT  CCTGGGGATC  AATGAAGCAA  ATGTTGCTCT   1140
GCAGAAATAA  AAGTCCTCCA  TGAAGCAAGT  CAAAAGTGCG  TCTGGTTGAG  ATAAATGACA   1200
CACCATATTC  AAGAAATGTG  TGGTTTTTCT  TTAAAAAAG   AATATACCAA  CCACAATGTA   1260
CAAAGATTGG  AGACATCATC  ACAAGAAATC  AAGTGATGTT  TTAATCAGGG  GGAGTACAAT   1320
ACGCGTTGCA  CTCTTTTTCC  CTTGATCGAG  GTTTTTTCC   CACTGGATTT  TCCTGACAAG   1380
GTTTTTAATG  AGGCAACAAA  TGGTGCGTAT  CAAAAGATAT  GTGTACTCTT  TTTCCTTCAC   1440
TAGAATTTTT  TCCCACAGGG  TTTTTCCTAG  TAAGGTTTTA  ACGAGGCACA  TTATCTATGG   1500
ACATCCAAGG  GGGAGTGTTA  TAAATACATT  GAATTAAGTG  GATAGTCCAT  AAGGTTGGCA   1560
CATGAACAAC  CATTCATATT  CACTAGGTGA  CATGAACCTT  TTTGGATAAG  AATGTATCTA   1620
TTTATTATGA  TACTTAATAT  GGTAATCTTT  GGAGTGATTT  CTCACTCTAT  AAATAGAGTT   1680
GTTCATTCAC  TATTGTAATA  TATACATATG  AGACTTGAAT  ACACTTGAAT  ACGAAGAAAG   1740
TCTTATCTTC  CATCTTACTT  CTCTTGTCTT  CTCTCTTTAT  GATTATATTC  TTATGAGCTT   1800
GATTTTATAA  CACGAATCTC  ATTATACGAA  AAGTTTTACT  ATTTATATTT  AATTAATAGA   1860
GGATTTAAAC  TTTTTAAATT  TCTGTCTTTA  TAGATGAGAA  CTTGTCTTTT  TGTTGAATCC   1920
AACTAAACAT  TCAATGAAGA  CAAATCAACC  TGTAAATCCC  TTCAAGTAG   GATTTATTCG   1980
AATCTCATTA  TACGAAAAGT  TTTACTATTT  ATATTTAATT  AATAGAGGAT  TTAAACTTTT   2040
TAAATTTCTG  TCTTTATAGT  AGAGAACTTG  TCTTTTTGTT  GAATCCAACT  AAACATTCAA   2100
TGAAGACAAA  TCAACCTGTA  AATCCCTTTC  AAGTAGGATT  TATTCGAATC  TCATTATACG   2160
```

```
AAAAGNCTTT  TTGTTGAATC  CAACTAAACA  TTCAATGAAT  ACAAATCAAC  CTGTAAATCC    2220
CTTTCAAGTA  GGATTTATTC  GAATCTCATT  ATACGAAAAG  TTTTACTATT  TATATTTAAT    2280
TAATAGAGAA  TTTAAACTTT  TTAAATTTCT  GTCTTATAG   ATGAGAACTT  GTCTTTTTGT    2340
TGAATCCAAC  TAAACATTCA  ATGAATACAA  ATCAACCTGT  AAATCCCTTT  CAAGTAGGAT    2400
TTATTCGAAT  CTCATTATAC  GAAAAGTTTT  ACTAGTTATA  TTTAATTAAT  ATTCAAGTCT    2460
CAATTTTTTT  TTAAATATTT  ACATTCCACA  TTTTAATCTA  TAATGAAAGT  TACTAAAATA    2520
TACTATCAAG  GAGAAAATAT  ACAAATGGC   CCATAACGAT  AGTCTTTAAT  ATATAATAAA    2580
TATGTTCATT  TGGATCCTTA  ATATATTTCA  CTTGATTAAA  ATAATAATAA  ATGTATAATA    2640
AAAAGTGGTC  ATTTTGGTCT  TTTGTCCTAA  ACATAGAGTT  TTTTACCTT   CAAAGAAAAA    2700
TCTTCCATAA  AATCTAATAC  TATTTTTTTT  TAATTCTCC   AACAAAATTT  ATTATTTTCT    2760
CTTTTAAATA  TTATTTTACT  GACCTAATAA  CAGTTTTTAT  TTTGAGCAAG  AAAAGTAGTA    2820
AATTTTGTTA  AATAAAGAAC  CAAAATAAAT  CATTTTAATC  AAAGTAAAAT  ATAATAACGA    2880
TTAAAATAAA  GTATACATTA  AGTCATTTCA  ATGAAGTGAA  ATAAATGAAG  AAGTAAAATA    2940
AAAAAATTAA  CCAAACAGTA  AGCATAGTTT  TGGTCATTTT  CTCTAATCCC  AAGTGTACCT    3000
CAAATTATAA  AAGTCCTTTT  GTTACTCAAT  TTCGTTGGTC  CCAGTCATTT  TCTGTGTTCA    3060
TCACCTATAT  ATATAGCAGT  AGACTAGTAG  CTTCTCCCAT  TCCTCTATCT  TCTATTATGG    3120
CCACTCAGTG  TTATGACCCC  GAAAACTCCG  CCTCTCGTTA  CACATTACTC  CCGGATCAAC    3180
CCGATTCCGG  CCACCGGAAG  TCCCTTAAAA  TCATCTCCGG  CATTTCCTC   TCCGTTTTCC    3240
TTTTGCTTTC  TGTAGCCTTC  TTTCCGATCC  TCAACAACCA  GTCACCGGAC  TTGCAAATCG    3300
ACTCCCGTTC  GCCGGCGCCG  CCGTCAAGAG  GTGTTTCTCA  GGGAGTCTCC  GATAAAACTT    3360
TTCGAGATGT  AGCCGGTGCT  AGTCACGTTT  CTTATGCGTG  GTCCAATGCT  ATGCTTAGCT    3420
GGCAAAGAAC  GGCTTACCAT  TTCAACCTC   AAAAAATTG   GATGAACGGT  AATTAACTTT    3480
CTTATTTTGA  CTTTTCTTTA  ATTTCTTTTT  TATTTGATCT  TAAAATTGAA  ATTATTTATA    3540
AATACTTATA  ACAGTTCTTT  TTTTTCTCAA  TGATATTTAT  GGCTATTGAT  CTGTTGGGGG    3600
TATCTTTTGG  ATTCTGATTG  GATGCTATTC  TGCAGATCCT  AATGGTGAGT  TCAAAGTTAA    3660
TTATTATCAC  TATTTTCTGC  TAGTTTTTAA  TTAATTATAT  TCTTAAACTA  TGATTATAAC    3720
TTTTAAAGCA  ATCTCATGAA  TGAGCAAATC  ATTAATTCGG  GTGCTTATGT  ATATCATCTC    3780
GGTTAATCCT  TTTACCTTAT  ACTCAAAAAC  AAATATTACT  CCCTTCAAAA  TAATTGATGT    3840
TTGACATAAT  CAATGTGATG  TTTAATTTTT  TTTTCTTTCA  AATTTGCCCT  TCCTAACCCC    3900
TATAATGATT  ATGTCAAATC  CAAAGTGAAA  AGACTATCAT  AATTACATAT  GCTTAGTCA     3960
CAATTAATTC  ATGTTAAATC  ATCAATAGTT  TTGGATTGGA  GGGAGTACTC  ATTAGGAAAA    4020
ATAATTAAGC  TAAATCATTC  TTATTTTCAC  TGTACATTAT  TTAGATTAAG  GGTGAAATAG    4080
GGGAGGAATC  AATTATCTTA  TTTTTCTAAA  TGGACAAGTA  TTTTGAAATA  ACAAATTTTA    4140
AGAAACACG   TCAAGTCAAA  TAGAGTAGGA  TGGATGGAGT  AAATTCTAAC  CTTTCTAGAT    4200
ATTCATAAAA  ATTAGTTGAA  CAGACATTTT  AATAAAGACC  ACAAGTTGAT  GAATTAAGCT    4260
TGTTGTTCCA  ATATAATTGG  GATTAACATG  AGATCTTGTG  GCAGTAATGT  TTTTTGCTTT    4320
TGTGCAATTT  TCCAATAAAA  AGAAAACACT  TGATTGGGTC  AGTATTATAC  AAGTTTGGAA    4380
ACCAATCACG  TTATGTGGGT  CATACTTTTT  TGTAGTAATG  TAATAATACC  AATAGTGGGG    4440
CCCCCACTCA  AAGTAATCCA  TCTTCCACTT  GATTTTTTA   TTTTTTTTG   AAATGGAGTA    4500
GGTTATCTTG  GCCGCTTAGC  AATTACTATT  ATCATGAGTA  AATGACGGAA  ATTATAAATT    4560
```

```
TTTAAGATAA  AATTATTATT  AATCTTTTAT  AATTTTATGG  TTATAAAAGT  CTCTCAAACT   4620
AATACAATAA  TATAAGCGCT  GATACATGAG  TCTGATGTGC  GAGATACATT  AATCTGATAG   4680
GTAAAAATGA  GGAACTAGAA  ATTTATAAAA  CTAATATGAA  TAATGATAAT  AAGATAACTT   4740
AAATGTGAAA  TTTCTATCAT  TTCTCCTAAC  ATACCACTAG  TGAAATTTGT  TTACGTATCT   4800
TGTTGAAGAA  AATCTTATCC  AAAAGTCAAA  AATAAAAACT  CGTGGCCAAA  TTTTCAAAAA   4860
AAAAAGAAGG  TTATCTTTTT  GCCGCAAAAA  GCATAGCAAT  TTGGTACGG   AACGTATTGA   4920
GATTTGTAG   AGTATTTTAT  AATTCAAATT  GCATAGAAAA  GTCTTACCTA  TACAAGTAAA   4980
AACTTTGAAA  TTTCTATTAA  CGTGAATAAA  TTGGTTAACA  GGACCATTGT  ATCACAAGGG   5040
ATGGTACCAC  CTTTTTATC   AATACAATCC  AGATTCAGCT  ATTTGGGGAA  ATATCACATG   5100
GGGCCATGCT  GTATCCAAGG  ACTTGATCCA  CTGGCTCTAC  TTGCCTTTTG  CCATGGTTCC   5160
TGATCAATGG  TATGATATTA  ACGGTGTCTG  GACAGGGTCC  GCTACCATCC  TACCCGATGG   5220
TCAGATCATG  ATGCTTTATA  CCGGTGACAC  TGATGATTAT  GTGCAAGTGC  AAAATCTTGC   5280
GTACCCCGCC  AACTTATCTG  ATCCTCTCCT  TCTAGACTGG  GTCAAGTTCA  AAGGCAACCC   5340
GGTTCTGGTT  CCTCCACCCG  GCATTGGTGT  CAAGGACTTT  AGAGACCCGA  CTACTGCTTG   5400
GACCGGACCA  CAAAATGGGC  AATGGCTGTT  AACAATCGGG  TCTAAGATTG  GTAAAACGGG   5460
TGTTGCACTT  GTTATGAAA   CTTCCAACTT  CACAAGCTTT  AAGCTATTGG  ATGGAGTGCT   5520
GCATGCGGTT  CCGGGTACGG  GTATGTGGGA  GTGTGTGGAC  TTTTACCCGG  TATCTACTAA   5580
AAAAACAAAC  GGGTTGGACA  CATCATATAA  CGGGCCGGGT  GTAAAGCATG  TGTTAAAAGC   5640
AAGTTTAGAT  GACAATAAGC  AAGATCATTA  TGCTATTGGT  ACGTATGACT  TGGGAAAGAA   5700
CAAATGGACA  CCCGATAACC  CGGAATTGGA  TTGTGGAATT  GGGTTGAGAC  TAGACTATGG   5760
GAAATATTAT  GCATCAAAGA  CTTTTTATGA  CCCGAAGAAA  GAACGAAGAG  TACTGTGGGG   5820
ATGGATTGGG  GAAACTGACA  GTGAATCTGC  TGACCTGCAG  AAGGGATGGG  CATCTGTACA   5880
GGTATGGACT  TGGATGAACA  CATTGTTTTG  TTATTTTACT  TTGCACCATA  CACAGCGTCT   5940
AGTTGTATCG  TAATAATCAT  GGTAGGGAAA  TTTCTTATTT  AGAGAAAGTT  GTTATAATCA   6000
ATGCATTTGT  AGGTGAAGTA  AATTCTGAAT  TGTATATGAA  ACGTGTCTAA  TAGTGTTTCG   6060
AAATAACAGA  GTATTCCAAG  GACAGTGCTT  TACGACAAGA  AGACAGGGAC  ACATCTACTT   6120
CAGTGGCCAG  TGGAAGAAAT  TGAAAGCTTA  AGAGTGGGTG  ATCCTACTGT  TAAGCAAGTC   6180
GATCTTCAAC  CAGGCTCAAT  TGAGCTACTC  CGTGTTGACT  CAGCTGCAGA  GGTTTGTTGC   6240
GTTACTTTTG  TTTTAAATTA  CAAACACGCG  CTTAATCTGC  AGTCCCAAAA  CTTGTTTAGC   6300
TATTGTGCAG  TTGGATATAG  AAGCCTCATT  TGAAGTGGAC  AAAGTCGCGC  TTCAGGGAAT   6360
AATTGAAGCA  GATCATGTAG  GTTTCAGTTG  CTCTACTAGT  GGAGGTGCTG  CTAGCAGAGG   6420
CATTTTGGGA  CCATTGGTG   TCATAGTAAT  TGCTGATCAA  ACGCTATCTG  AGCTAACGCC   6480
AGTTTACTTT  TACATTTCTA  AAGGAGCTGA  TGGTCGTGCA  GAGACTCACT  TCTGTGCTGA   6540
TCAAACTAGG  TTTGCTTTTC  TATCTGGCAC  AATTAATTTG  TCCTTGTAAA  ATGGAGATGG   6600
ATAAAGTAG   CGGGTTGTTG  ATCTGATATA  TGCAGATCCT  CTGAGGCTCC  GGGAGTTGGT   6660
AAACAAGTTT  ATGGTAGTTC  AGTACCTGTG  TTGGACGGTG  AAAAACATTC  AATGAGATTA   6720
TTGGTAAGTG  ATAATGATTC  CCTTATTTTA  CCTTGATTTT  ATTCCATTTC  TTCACTTCAC   6780
AATAATTAAA  GTACTTGGCA  GTTGCATTTG  AGTAAAGGT   TTTTTATAAA  CTGAATTTTA   6840
GGTGGATCAC  TCAATTGTGG  AGAGCTTTGC  TCAAGGAGGA  AGAACAGTCA  TAACATCGCG   6900
AATTTACCCA  ACAAAGGCAG  TAAATGGAGC  AGCACGACTC  TTTGTTTTCA  ACAATGCCAC   6960
```

| | | | | | |
|---|---|---|---|---|---|
| AGGGGCTAGC | GTTACTGCCT | CCGTCAAGAT | TTGGTCACTT | GAGTCAGCTA | ATATTCAATC | 7020
| CTTCCCTTTG | CAAGACTTGT | AATCTTCTTT | ATTTCGTTTT | TTTTTTCTTT | TTCATTTGAA | 7080
| GGTTATTTCA | CCGACGTCCC | ATCAAGAAAG | GGAAGAGGGA | GATCAATATA | TGTAGTGTTA | 7140
| TTCGCCCTAC | CTTAGGATTA | GATGTCATCT | AGCAATGTCA | AATCTAGTAG | AGTATACAAT | 7200
| GTATGGGTTC | CTGGAAACCG | AGTAGAGCTT | ACCTGGATTC | TATGTAAACT | AAGAAAGCTC | 7260
| AGCAAATATA | TGCACAAATA | ATTTACAGAA | ACAACTTGGG | AATGTTGACA | AACTTGATTA | 7320
| TTTTTTCTTT | TATATAACTA | GTAATAACGG | CAAGCTCTCC | GCAATCTCGT | TGAGCAAAAG | 7380
| TATAAATGGT | TACGAGCCAC | CTAAATATTT | TTGTTCAACG | AGATTGGAAT | TGGAGCTTAT | 7440
| TATACACAAC | ATATACAACA | ATGATTCATC | TTCTAACTCA | TACAATTCTA | TACGTAAGGT | 7500
| CGAAGTTAGG | AGGGAGTGAG | CAACTTGGTA | AAAAGTATAT | GGTATAAGTA | AGATATTTTT | 7560
| AAATGTATTA | TGTATCAGTT | GTACTCAATC | AAAGAGCGGA | TAAATACAAT | TGATACAATA | 7620
| TACAAAATAG | TTATGCACTA | AATAATAAAT | AGAGGATAAA | ATGTAAAAGA | AATACAAAAT | 7680
| ATAATTCTCT | CGATCTCGCT | CCCGTCTCTC | CTCTCTCGAT | CTCACTCATC | TCTCTTCTCT | 7740
| TAATATGTAT | TCATTTAAT | ACAAATTAGT | TTCTATTTGT | ATTTTTCTT | CAAAATTCAC | 7800
| GAAAAAAAT | ATATATAAAT | ATAAATGCAT | AGCGAACAAG | AATATTATTA | TGAATCATAA | 7860
| ATAATGAAAC | TGTAGTTATG | GAATACTTTT | AAGGGTTAAT | GTTTGTTGTT | TTTGAAATTT | 7920
| CCCCTCTTGA | AGCCCTTAAG | TGCAAATCTT | GAATCCACTA | TGAATATGAT | TCATTCTTTA | 7980
| TACATATACA | ATAATAATGA | TACATTTCTA | TTTACGAATG | ATATAATTCC | CGTACAAATA | 8040
| AATTTAGAGT | TACAAAAGAA | GATCAGCCCA | GCCCATCTAA | TTCAAGCCTC | GTGGGCCAAG | 8100
| AAATTTAATG | AGCTAAGGAA | GGTTGGCCCT | TTATTTGAAA | GTGCCTAAAT | TGTTCAACTC | 8160
| AACCTAATTT | TAGAAGGGCC | ACAAACTGGG | GGGGTTAGCA | TTTTTTTCCT | TTTTAAACTT | 8220
| AAAGCTCTAT | ACCATCAAGT | AAATGAGACT | ATTTTCAAAT | CAAATATGGT | AACAATGGTG | 8280
| TTTTTTCAAT | AACACTAACA | AAAAATTTGT | ATGATTAACA | TGTACCTTGG | ATACTACATG | 8340
| CCCAAGCTAC | ATGTATATGT | TGTGATGCAT | TCCAAATATG | CAAGCGAGAT | AAGAGCGACC | 8400
| AAGATGGGTG | GGAGGCGAGG | GCTTGGAATT | TGTTTATATA | TCCTAGATAC | ATGCGAATCC | 8460
| ATTTGAATGA | AGTCCTTCTA | GAATAAATAG | ACGTATCGAA | ATGCACCAAA | ATCTAGTAAG | 8520
| ATTTGTAATG | TTACAGCATA | ACGTGCATCT | AAGTAATTAG | CTAGCTCATA | CACTAGTGAG | 8580
| ATCCTTTTAG | TTACCGTATA | TAAATAGTTT | TGACCCATGG | GACGATCCTA | ACCTGTTCCC | 8640
| GATCAAGACT | CAAGGGCTTA | TAAGTCCTAA | TGTTGAATGG | TCTTGTAAAT | CCTATCACAA | 8700
| CCATACCCCA | ATACCGAGTT | GGGTTGGACC | GGCTCCATGG | GCTTAGCAAA | CTTTGACATA | 8760
| TCTACACATA | ATGGAACAAA | TGAAAAAAAA | AATACGAAAT | GAAATTATTT | TTAAAACAAT | 8820
| AAAGACAATA | TTTTTTAGA | GAAAGTTACA | AAATTATATA | CAACTTAATA | TTATTATATC | 8880
| CTCTAAAAAT | TCCTATCTTT | GAATTAAATA | CAAAAATTTC | CTTTTTCCTT | CTCTCTCTTT | 8940
| TTTCATCCGG | ATACATCACT | CGACCTCTAT | GAAATACACC | ACAATTTGT | TTGTGTATAC | 9000
| TAATATGGTA | GAAATATTAT | TACCGATACA | TAACCCCAAT | TATTTCAAAT | ATAATTATAT | 9060
| TAGTGATACA | CAACTTATTT | ATTGTTTGTT | ATATATATAG | AGCGAATGAG | CAATGTATCC | 9120
| ACAAGTTTTG | AAAAATCCAA | AATCATTTAT | TTAAAAAACT | TTTAAGATAA | TGTGTAATTA | 9180
| ACGCCTAAAA | ACTATTGAGG | TTTCTGTATT | CTGTATTGTA | TTCCTTTTAA | GGAAAAATAT | 9240
| ATAATAACAA | ACTATTAATT | CAAATTAAAT | GTTATATACA | CAATTTGATT | TAACCTGTAG | 9300
| CAAAATATTT | TCATTCGCCT | CTCTCCCTAG | GTTTCTCACT | CGCCACTCTC | GCTTTTATAC | 9360

-continued

| | | | | | |
|---|---|---|---|---|---|
| AAACACAAAT | GTATAAAATG | TGTTTGTGTT | TGTATAAAGC | GAGAGAAAAT | GTATATACAA | 9420 |
| ATATGAATAC | ATATATTTTC | GTCCTATATA | CTTATAATGA | TACAAATACA | GATCTTTTCC | 9480 |
| TATCCAGTTC | TCTTTGTCT | TTCTCACTTT | ATACAAACAC | AAATTATACA | AATTACAATG | 9540 |
| TATAATTATT | GTTGCATAAA | GCGAGAGAGA | GATTCGATAT | ACAAATAGTT | TATTTCGATT | 9600 |
| CAATTATATA | TAAATTCAAA | TTTTATGCAG | ATATGCAAAC | AAATAAAATA | AAATTTGAGA | 9660 |
| GGCTGTCAGC | GATTTATGCC | AACGATTTAT | ACAAATGACC | TACCACCGAA | ATTATACAAA | 9720 |
| TCTGAAGCAT | TGCCAGCGAG | CTATACAATC | TGATGCTCCA | TAACAAACAT | AAAATTTATC | 9780 |
| ATGGAACGTA | AATATACAAA | CTATGACTAT | AACATTCAAA | TATAATTTTT | ATGTTTGCCA | 9840 |
| TATATGAAAA | TTGATCTAAG | CCTTTCGAAC | TATCCGATGT | CAATAGTTTC | ACCCAGATAG | 9900 |
| CCATTAATAT | CAAAGTTCAG | GCCCAGATCA | TTGGGATAAT | TTGGGCCTAT | ATTGTGGACC | 9960 |
| GTGACTCGAA | AAACACCTAA | TGCTACAGGC | TACACCAAAT | TGATTAATGA | TTTCTCATCT | 10020 |
| TCTGAAAACA | AAATAAATTT | ATAATTTTA | TATTACATAA | ATATTTTTT | CCCGCTAAAT | 10080 |
| TCAAAGTAGT | CAAACATTCA | AAAATATTTA | AACTGATAAT | CAGAGCTCAA | GTCACCTTTT | 10140 |
| CATTTATACT | ATTATTATAT | TTTTTAATA | TTAGAGACAA | AAAAGAAAAG | CTCTCATATT | 10200 |
| AAATAATAAA | ATATATAGAA | TTGACAGAAC | CATTGACCA | TTCTTCTCAT | AGTTAAAATA | 10260 |
| GTATATAATT | GGGCTCGACT | TTATATAAAA | TTCTGATATA | TTATTTAATA | TTCTTCTTTG | 10320 |
| CTTTTCCTTT | TCTGCATTAC | TTTTTTTTC | CATTTAAATA | ATAATACAGG | TTTATGGGTA | 10380 |
| TTATAAAACG | GATCC | | | | | 10395 |

( 2 ) INFORMATION FOR SEQ ID NO:4:

( i ) SEQUENCE CHARACTERISTICS:
( A ) LENGTH: 4032 base pairs
( B ) TYPE: nucleic acid
( C ) STRANDEDNESS: double
( D ) TOPOLOGY: unknown ( i i ) MOLECULE TYPE: DNA (genomic)

( v i ) ORIGINAL SOURCE:
( A ) ORGANISM: Lycopersicon esculentum ( i x ) FEATURE:
( A ) NAME/KEY: prim_transcript
( B ) LOCATION: 889

( x i ) SEQUENCE DESCRIPTION: SEQ ID NO:4:

| | | | | | |
|---|---|---|---|---|---|
| GATCAAATTT | AGTTTTGACA | TCTTCTTCAC | ATTTCAAGCA | TTAAAACCAA | TTAACACTGT | 60 |
| TTATTATTA | TTATTATATT | AATTTAAATT | TTCTGAGTTT | AATTTTATTA | TTCTAACATT | 120 |
| ATTTTATATA | CTTTTCATTG | AAAAATTGCA | TTGTTTATAT | TCTTACTTCA | TAATGTACGT | 180 |
| ATATAACATT | CTTTGCAGAC | TTCATTTATG | AAATTACACT | ATAGAATAAT | AATTTGATTT | 240 |
| ATATGTACTT | CCTTCCTTTC | AAATTGATTA | AATTGTTAAG | GTGTTTCACA | CATTTAAAAT | 300 |
| AAATTAAGTC | ACATATTAAG | CATAACTTTA | AATTTTTACA | AAATAAGAG | CTCTCTATAA | 360 |
| AGTTTGACTT | TAAGTCTCCA | AATTTGTTAA | TACAGACCTG | AAAGAGTGTA | GGAGCTAACA | 420 |
| AAACAAATAG | TTATAAAAAG | TAATTTTATT | CAATTTTATA | GAATTAAAAG | CTATATGTGC | 480 |
| ATACACCAAA | ATTTACATC | CTTTATCATA | GCAAAATTTA | TAGAAAATAA | AATAAATTT | 540 |
| GTAACTAATG | TTTTTTTTTT | CAAACACTGT | AAAACACGAA | AAAATTGCT | AATGTGTAAG | 600 |
| AAAACATGTG | TAATATAAAA | CAAATATAAA | AGAGTCCACG | TGCATCGCAT | GAGTACCTAT | 660 |
| ATTAATTTTA | GCTTGAAAAT | AAAAATTAAT | ATTTTTTTAT | TTCAAACACT | ACCAATTATT | 720 |

```
ATAAAACTAT TTAACTTAAT TGGATGCACC AACTTTGACA GGTGTTAATT CACTTCAATA    780
TTCAACCAAA AAAAAAAGA AGGTTAAAAC GCAAAGCAAC TTAATTCATT TGTTATAAAT    840
TGGAGGAGCC AAAGATAGTG AGATTCACAA AACTTTATAT CTCTAAGAAT GGAAATTCAA    900
AAGGTATCAT AGTTTCTAAT ATTTTTTTA ATTATATATG TCTATCTTAA GTTTCATTCA    960
TATACTCATG ATTAATTTAT TGATCATTTT AAACAATGAA ACATATCTTA GATTTAATTT   1020
TATTTATTTA TTTTTATAAC ATAGGAGTTT GATTTAACGA TAGTTCCAAC AGAAGGTGAA   1080
ATTGATGCAC CATCATCGCC AAGGAAGAAT TTATGTCTCA GTGTGATGGA ATCTGATATT   1140
AAAAATGAAA CGTCTTTTCA GAACTCGAC ATGATTTGA CTCAATATTT AGAGACATTG    1200
TCCGAGCGAA AAAGTATCA TATAGGTAAG GATATACATA TGTATAGTCT TTCCATACAA    1260
ACATAGTTAC TTTTTACTCA ACGAAATTAT ACAAGCATTT TAGTGATCGA GGTAATTTAA   1320
TCTCAATTTT ATTAAATAA ATACATTTTC ATTTATTTTT ACGTGTGTAA TAAACATAAA   1380
AGTATTTATA AGAAAAATTA ATCAAAAGTT ATTCATTAAT AAATCATCCC TAACTTTATT   1440
TTTACATATC TTTTAAGTAT TTTTGATTTG GCCAAATAAT ATTTACGAT TTATTCATA    1500
ATTATATCTT TGGTTATTTA ATTTACAGGT TATCCAATTA ACATGTGTTA CGAACATCAT   1560
GCCACTTTAG CCCCACTTTT GCAATTTCAT TTGAACAATT GTGGAGATCC CTTTACTCAG   1620
CACCCTACAG ATTTCCATTC AAAAGATTTT GAAGTGGCTG TTTTAGATTG GTTTGCACAA   1680
CTCTGGGAAA TAGAGAAAGA TGAATATTGG GGNTACATTA CTAGTGGTGG CACTNAGGGC   1740
AATCTCCATG GCCTTTTGGT TGGGCAGGTA TCATTTTCAA GAAAGGGGGT GGGGGGAGAG   1800
GTGGTAGTTT TTGAATCATA TGAAAAATCA AAAATTAAA TGGCGTAATC AGCCATTGTC   1860
ATGGTCAAAA TCATTACGAG CAAGACGTCT TACTTTACTT TTGTTGTACC ATAGGTACAC   1920
AATCAATGAC AAATTTGTAT TGCCACACAA TAATGACCAC AATCCTTCTA TGCAAGAGCT   1980
ATTTCTTTCT TTTTCCCTTT GCGGTAGTTC ACAATAAACA TACCATAGTG ACGCATAAAC   2040
ATACAGTACG ATTAGCCATT TTTGCCAAAT AAAATTTATT TTCTCTCAAA CCTCCCGTAG   2100
AGGTGAGTTT TGACATATAT TATTTTTTCT CAAACCTCCT ATAGAGGTGA GTTGAGACAT   2160
ATATTCAATC CATAATGATT TTATCATATC TTGACCCATT CTCTTATAGA ATGGTCGAGC   2220
ATTCATAATA CTCATCACAA GTCACATTCT CTTCAAGGAA TTCATAAATT TGTATTATAA   2280
GTACATTGTC ATGGTTCTAA AATTCATTAT ATTTCCATGA CACACCTCAA CATCACTTTG   2340
AAAGATCAAG TGTACCATCA CTTTATCTTC TTGTCTCATG ATAGAGGATT TATAAAGTTG   2400
TCAAATTGGG TCGACAACAT TCAGAAGTCC AATGACCTTT CATACCATTT TATAATAAAA   2460
ATTCTCTTCA CATTTTGAAG GACTATTTGG AGAACCCATA GTGTTCTTCC TTTTATAATT   2520
ATCACAATGA TGACTATTAT AATTTCGTCC CTTCACGCCC TTATTCATAT CATTAATTAT   2580
TTGTCATCTT TCAGACGAAT TATTTGTTGC TACTACATTC ATATAATTGA ATGGAGCAAG   2640
TCAACAGATG GATTTCAAAG TTATCACATG TTGCTTCCAT ATTCTTTTCA AGGAATGGAG   2700
CAAATTTAAT ATGATGAATT TCAATACTTT TCATCAAAAA TATATTATTT TGCCTCAGTC   2760
ATCATCTTAT CATCAATTTG GTGCATGGAG ACTCAAACTC AATGTCTTAT CCATACAAGG   2820
CACATTAGGC CATAATTCTA TGGGACTTGA ACCCAATACC TTATCATTAT GGTGCATCAA   2880
AACTCGAATT GATGTCTTAC CCTCTTGGTG CGATAGAACT TGAATCTACC GTCTTACCCT   2940
CAAATATTTT TCATAATGAA TGACATAAAT GAGTCTTTTT TAAACAAATT TGATAACATA   3000
TTTGAGTTTT TTTCTTATGG TTAAATGATG CAAGTGCTTC ATCACTTTCA TAAAGCATTT   3060
GAACAATATT ATATATTTGT GCAGAAGAGA GCTACTTCCT AATGGATATT ATATGCATCA   3120
```

-continued

| | | | | | |
|---|---|---|---|---|---|
| AAAGATTCAC | ATTACTCGAT | TTTCAAAGCA | GCAAGAATGT | ATCGAATGGA | GCTACAAACT | 3180 |
| ATCAACACTT | TAGTTAATGG | GGAAATTGAT | TATGAAGATT | TACAATCAAA | GTTACTTGTC | 3240 |
| AACAAGAACA | AACCAGCTAT | CATCAATATC | AATATTGGTA | AAAATACATA | CATATATATT | 3300 |
| CTTACATCTT | ATAACATCAC | TTTTGGTAAA | TTAGTATATA | TGTGTTTATA | GGAACAACCT | 3360 |
| TCAAAGGAGC | TATTGATGAC | CTCGATTTCG | TCATACAAAC | ACTTGAAAAT | TGTGGTTATT | 3420 |
| CAAATGACAA | TTATTATATC | CATTGCGATG | CAGCATTATG | TGGGCTAATT | CTCCCATTTA | 3480 |
| TCAAACATGT | AAGCTTATTT | TTATTCAATT | TTCCTTCAAC | GCTCGATCGA | AGTTACAATG | 3540 |
| ACATAGTTTC | TTTCTATGGT | ATTTGACAAT | AGGCAAAAAA | AATTACCTTC | AAGAAACCAA | 3600 |
| TTGGAAGTAT | TTCAATTTCA | GGGCACAAAT | TCTTGGGATG | TCCAATGTCT | TGTGGCGTTC | 3660 |
| AGATAACAAG | GAGAAGTTAC | GTTAGCACCC | TCTCAAAAAT | TGAGTATATT | AATTCCGCAG | 3720 |
| ATGCTACAAT | TTCTGGTAGT | CGAAATGGAT | TTACACCAAT | ATTCTTATGG | TACTGTTTAA | 3780 |
| GCAAGAAAGG | ACATGCTAGA | TTGCAACAAG | ATTCCATAAC | ATGCATTGAA | AATGCTCGGT | 3840 |
| ATTTGAAAGA | TCGACTTCTT | GAAGCAGGAA | TTAGTGTTAT | GCTGAATGAT | TTTAGTATTA | 3900 |
| CTGTTGTTTT | TGAACGACCT | TGTGACCATA | AATTCATTCG | TCGTTGGAAC | TTGTGTTGCT | 3960 |
| TAAGAGGCAT | GGCACATGTT | GTAATTATGC | CAGGTATTAC | AAGAGAAACT | ATAGATAGTT | 4020 |
| TCTTCAAAGA | TC | | | | | 4032 |

( 2 ) INFORMATION FOR SEQ ID NO:5:

( i ) SEQUENCE CHARACTERISTICS:
        ( A ) LENGTH: 10396 base pairs
        ( B ) TYPE: nucleic acid
        ( C ) STRANDEDNESS: double
        ( D ) TOPOLOGY: unknown ( i i ) MOLECULE TYPE: DNA (genomic)

( v i ) ORIGINAL SOURCE:
        ( A ) ORGANISM: Lycopersicon pimpinellifolium ( i x ) FEATURE:
        ( A ) NAME/KEY: misc_feature
        ( B ) LOCATION: 2166
        ( D ) OTHER INFORMATION: /note= "N represents approximately
        0.2 kb of missing sequence in the repetitive DNA
        region."

( i x ) FEATURE:
        ( A ) NAME/KEY: prim_transcript
        ( B ) LOCATION: 3117..7043

( x i ) SEQUENCE DESCRIPTION: SEQ ID NO:5:

| | | | | | |
|---|---|---|---|---|---|
| GATCTCGATA | AGTTATGTCT | TGTTGGAATC | GATATCAAAT | AACCGTCGAC | GGTATCTTTG | 60 |
| ATATGAGGTA | GCGCTCAATG | ATATAAATTG | TGATGAGGAT | CTTGAATTCA | AATCTGTCAT | 120 |
| ATAGTGTGAA | CAGATAAATG | GTTGGCCAAG | TAAATGCAC | AATTCAAGTA | TATTTTGTTT | 180 |
| CACTTAGAAA | AGTGACATTT | TGGACTGGTA | GTCCATAAAT | CAAGGTATAA | TGTCAGTGGG | 240 |
| GTACAAATAA | ATTATTATGT | GATAGTATAA | CCGTAAGATA | TCAAATACGG | TTTGTGCCTT | 300 |
| GGGGCATAAA | AGTTTATCGC | AAAAATCCTG | ACATTATTGG | AGATGTTTTC | TCCTTTGGTG | 360 |
| GATGCAATGA | GGTTTGTTTT | GATCTGGCAA | CATATGAAAA | ACTTGAATGC | ATGTAATGAA | 420 |
| AAATTGTAAT | GAAGGTTATA | TGAAAATCCT | TGAAACAATC | CAGGTGTCTG | AAGCATATAA | 480 |
| AGGTTGAAAG | AAACTTATCC | AATAAAGCTT | CAAGAATCCT | TATATGGATT | GAAATAGTCA | 540 |
| AGGAAGAAAA | AGGGTACAAA | AGAATGACCC | TAATTGTCCT | TGTATTTTA | TGAAAAGGTC | 600 |
| TTGGTAAGAC | AAAATTTTGT | CTTGACCTAC | AGATTGTTAA | TTTGACAAAT | AAAATATTTG | 660 |

| | | | | | |
|---|---|---|---|---|---|
| TCTAACAGAC | AACAGTGCAC | ATACACTGAA | AAATTTTGAT | GCAATTTTAT | GTGGATATAT | 720 |
| CGCATTCATT | GAGTACCCCA | ATGATTATGA | GATCACTTGA | CATAAATGAT | GATTCAGTTT | 780 |
| GATCTCAAAA | GAAGGATAAG | AGTTTCTTGG | TGATGAAACT | CTATCTTGGT | GCAATGAGGG | 840 |
| CACTAGTGCA | TCTTACTAAC | AATATTTGAC | TAGATATTTG | TTTTGCAGTA | AATTTACTGG | 900 |
| CAAGATTCAG | TTTCTCCCCG | ATAAAAGGAC | ATTGAAATGG | TGTTGAGCAC | ATGAATGAAT | 960 |
| ATCCTCAAAG | GACCATAGTT | ATGGGTTTAT | TCTATCCCGA | GGAATCCAAG | ACAAAATTGA | 1020 |
| TTGATTACGC | AGATGCAGAA | TATTTATCTG | ATCCGCATAA | AGCTCTATCT | CAAGCACGCT | 1080 |
| ATGTGTTTGC | ATGTGGAGGC | ACAATAATAT | CCTGGGGATC | AATGAAGCAA | ATGTTGCTCT | 1140 |
| GCAGAAATAA | AAGTCCTCCA | TGAAGCAAGT | CAAAAGTGCG | TCTGGTTGAG | ATAAATGACA | 1200 |
| CACCATATTC | AAGAAATGTG | TGGTTTTCT | TTAAAAAAG | AATATACCAA | CCACAATGTA | 1260 |
| CAAAGATTGG | AGACATCATC | ACAAGAAATC | AAGTGATGTT | TAATCAGGG | GGAGTACAAT | 1320 |
| ACGCGTTGCA | CTCTTTTTCC | CTTGATCGAG | GTTTTTTCC | CACTGGATTT | TCCTGACAAG | 1380 |
| GTTTTAATG | AGGCAACAAA | TGGTGCGTAT | CAAAAGATAT | GTGTACTCTT | TTTCCTTCAC | 1440 |
| TAGAATTTTT | TCCCACAGGG | TTTTTCCTAG | TAAGGTTTTA | ACGAGGCACA | TTATCTATGG | 1500 |
| ACATCCAAGG | GGGGGTGTTA | TAAATACATT | GAATTAAGTG | GATAGTCCAT | AAGGTTGGCA | 1560 |
| CATGAACAAC | CATTCATATT | CACTAGGTGA | CATGAACCTT | TTTGGATAAG | AATGTATCTA | 1620 |
| TTTATTATGA | TACTTAATAT | GGTAATCTTT | GGAGTGATTT | CTCACTCTAT | AAATAGAGTT | 1680 |
| GTTCATTCAC | TATTGTAATA | TATACATATG | AGACTTGAAT | ACACTTGAAT | ACGAAGAAAG | 1740 |
| TCTTATCTTC | CATCTTACTT | CTCTTGTCTT | CTCTCTTTAT | GATTATATTC | TTATGAGCTT | 1800 |
| GATTTTATAA | CACGAATCTC | ATTATACGAA | AAGTTTTACT | ATTTATATTT | AATTAATAGA | 1860 |
| GGATTTAAAC | TTTTTAAATT | TCTGTCTTTA | TAGATGAGAA | CTTGTCTTTT | TGTTGAATCC | 1920 |
| AACTAAACAT | TCAATGAAGA | CAAATCAACC | TGTAAATCCC | TTTCAAGTAG | GATTTATTCG | 1980 |
| AATCTCATTA | TACGAAAAGT | TTACTATTT | ATATTAATT | AATAGAGGAT | TTAAACTTTT | 2040 |
| TAAATTTCTG | TCTTTATAGT | AGAGAACTTG | TCTTTTGTT | GAATCCAACT | AAACATTCAA | 2100 |
| TGAAGACAAA | TCAACCTGTA | AATCCCTTTC | AAGTAGGATT | TATTCGAATC | TCATTATACG | 2160 |
| AAAAGNCTTT | TTGTTGAATC | CAACTAAACA | TTCAATGAAT | ACAAATCAAC | CTGTAAATCC | 2220 |
| CTTTCAAGTA | GGATTTATTC | GAATCTCATT | ATACGAAAAG | TTTACTATT | TATATTTAAT | 2280 |
| TAATAGAGAA | TTTAAACTTT | TTAAATTTCT | GTCTTTATAG | ATGAGAACTT | GTCTTTTGT | 2340 |
| TGAATCCAAC | TAAACATTCA | ATGAATACAA | ATCAACCTGT | AAATCCCTTT | CAAGTAGGAT | 2400 |
| TTATTCGAAT | CTCATTATAC | GAAAAGTTTT | ACTATTTATA | TTTAATTAAT | ATTCAAGTCT | 2460 |
| CAATTTTTTT | TTAAATATTT | ACATTCCACA | TTTTAATCTA | TAATGAAAGT | TACTAAAATA | 2520 |
| TACTATCAAG | GAGAAAATAT | ACAAAATGGC | CCATAACGAT | AGTCTTTAAT | ATATAATAAA | 2580 |
| TATGTTCATT | TGGATCCTTA | ATATATTTCA | CTTGATTAAA | ATAATAATAA | ATGTATAATA | 2640 |
| AAAAGTGGTC | ATTTTGGTCT | TTTGTCCTAA | ACATAGAGTT | TTTTTACCTT | CAAAGAAAAA | 2700 |
| TCTTCCATAA | AATCTAATAC | TATTTTTTT | TAATTCTCC | AACAAATTT | ATTATTTCT | 2760 |
| CTTTTAAATA | TTATTTTACT | GACCTAATAA | CAGTTTTTAT | TTTGAGCAAG | AAAAGTAGTA | 2820 |
| AATTTTGTTA | ATAAAGAAC | CAAATAAAT | CATTTTAATC | AAAGTAAAAT | ATAATAACGA | 2880 |
| TTAAAATAAA | GTATACATTA | AGTCATTTCA | ATGAAGTGAA | ATAAATGAAG | AAGTAAAATA | 2940 |
| AAAAAATTAA | CCAAACAGTA | AGCATAGTTT | TGGTCATTTT | CTCTAATCCC | AAGTGTACCT | 3000 |
| CAAATTATAA | AAGTCCTTTT | GTTACTCAAT | TTCGTTGGTC | CCAGTCATTT | TCTGTGTTCA | 3060 |

```
TCACCTATAT ATATAGCAGT AGACTAGTAG CTTCTCCCAT TCTTCTATCT TCTATTATGG    3120
CCACTCAGTG TTATGACCCC GAAAACTCCG CCTCTCGTTA CACATTACTC CCGGATCAAC    3180
CCGATTCCGG CCACCGGAAG TCCCTTAAAA TCATCTCCGG CATTTCCTC  TCCGTTTTCC    3240
TTTTGCTTTC TGTAGCCTTC TTTCCGATCC TCAACAACCA GTCACCGGAC TTGCAAATCG    3300
ACTCCCGTTC GCCGGCGCCG CCGTCAAGAG GTGTTCTCA  GGAGTCTCC  GATAAAACTT    3360
TTCGAGATGT AGCCGGTGCT AGTCACGTTT CTTATGCGTG GTCCAATGCT ATGCTTAGCT    3420
GGCAAAGAAC GGCTTACCAT TTTCAACCTC AAAAAAATTG GATGAACGGT AATTAACTTT    3480
CTTATTTTGA CTTTTCTTTA ATTTCTTTTT TATTTGATCT TAAAATTGAA ATTATTTATA    3540
AATACTTATA ACAGTTCTTT TTTTTCTCAA TGATATTTAT GGCTATTGAT CTGTTGGGGG    3600
TATCTTTTGG ATTCTGATTG GATGCTATTC TGCAGATCCT AATGGTGAGT TCAAAGTTAA    3660
TTATTATCAC TATTTCTGC  TAGTTTTTAA TTAATTATAT TCTTAAACTA TGATTATAAC    3720
TTTTAAAGCA ATCTCATGAA TGAGCAAATC ATTAATTCGG GTGCTTATGT ATATCATCTC    3780
GGTTAATCCT TTTACCTTAT ACTCAAAAAC AAATATTACT CCCTTCAAAA TAATTGATGT    3840
TTGACATAAT CAATGTGATG TTTAATTTTT TTTTCTTTCA AATTTGCCCT TCCTAACCCC    3900
TATAATGATT ATGTCAAATC CAAAGTGAAA AGACTATCAT AATTACATAT GCTTTAGTCA    3960
CAATTAATTC ATGTTAAATC ATCAATAGTT TTGGATTGGA GGGAGTACTC ATTAGGAAAA    4020
ATAATTAAGC TAAATCATTC TTATTTTCAC TGTACATTAT TTAGATTAAG GGTGAAATAG    4080
GGGAGGAATC AATTATCTTA TTTTTCTAAA TGGACAAGTA TTTTGAAATA ACAAATTTTA    4140
AGAAAACACG TCAAGTCAAA TAGAGTAGGA TGGATGGAGT AAATTCTAAC CTTTCTAGAT    4200
ATTCATAAAA ATTAGTTGAA CAGACATTTT AATAAGACC  ACAAGTTGAT GAATTAAGCT    4260
TGTTGTTCCA ATATAATTGG GATTAACATG AGATCTTGTG GCAGTAATGT TTTTTGCTTT    4320
TGTGCAATTT TCCAATAAAA AGAAAACACT TGATTGGGTC AGTATTATAC AAGTTTGGAA    4380
ACCAATCACG TTATGTGGGT CATACTTTTT TGTAGTAATG TAATAATACC AATAGTTGGG    4440
CCCCCACTCA AAGTAATCCA TCTTCCACTT GATTTTTTA  TTTTTTTTT  GAAATGGAGT    4500
AGGTTATCTT GGCCGCTTAG CAATTACTAT TATCATGAGT AAATGACGGA AATTATAAAT    4560
TTTTAAGATA AAATTATTAT TAATCTTTTA TAATTTTATG GTTATAAAAG TCTCTCAAAC    4620
TAATACAATA ATATAAGCGC TGATACATGA GTCTGATGTG CGAGATACAT TAATCTGATA    4680
GGTAAAAATG AGGAACTAGA AATTTATAAA ACTAATATGA ATAATGATAA TAAGATAACT    4740
TAAATGTGAA ATTTCTATCA TTTCTCCTAA CATACCACTA GTGAAATTTG TTTACGTATC    4800
TTGTTGAAGA AAATCTTATC CAAAAGTCAA AAATAAAAAC TCGTGGCCAA ATTTTCAAAA    4860
AAAAAGAAG  GCTATCTTTT TGCCGCAAAA AGCATAGCAA TTTTGGTACG GAACGTATTG    4920
AGATTTGTA  GAGTATTTTA TAATTCAAAT TGCATAGAAA AGTCTTACCT ATACAAGTAA    4980
AAACTTTGAA ATTTCTATTA ACGTGAATAA ATTGGTTAAC AGGACCATTG TATCACAAGG    5040
GATGGTACCA CCTTTTTTAT CAATACAATC CAGATTCAGC TATTTGGGGA AATATCACAT    5100
GGGGCCATGC TGTATCCAAG GACTTGATCC ACTGGCTCTA CTTGCCTTTT GCCATGGTTC    5160
CTGATCAATG GTATGATATT AACGGTGTCT GGACAGGGTC CGCTACCATC CTACCCGATG    5220
GTCAGATCAT GATGCTTTAT ACCGGTGACA CTGATGATTA TGTGCAAGTG CAAAATCTTG    5280
CGTACCCCGC CAACTTATCT GATCCTCTCC TTCTAGACTG GGTCAAGTTC AAAGGCAACC    5340
CGGTTCTGGT TCCTCCACCC GGCATTGGTG TCAAGGACTT TAGAGACCCG ACTACTGCTT    5400
GGACCGGACC ACAAAATGGG CAATGGCTGT TAACAATCGG GTCTAAGATT GGTAAAACGG    5460
```

```
GTGTTGCACT TGTTTATGAA ACTTCCAACT TCACAAGCTT TAAGCTATTG GATGGAGTGC    5520
TGCATGCGGT TCCGGGTACG GGTATGTGGG AGTGTGTGGA CTTTTACCCG GTATCTACTA    5580
AAAAAACAAA CGGGTTGGAC ACATCATATA ACGGGCCGGG TGTAAAGCAT GTGTTAAAAG    5640
CAAGTTTAGA TGACAATAAG CAAGATCATT ATGCTATTGG TACGTATGAC TTGGGAAAGA    5700
ACAAATGGAC ACCCGATAAC CCGGAATTGG ATTGTGGAAT TGGGTTGAGA CTAGACTATG    5760
GGAAATATTA TGCATCAAAG ACTTTTTATG ACCCGAAGAA AGAACGAAGA GTACTGTGGG    5820
GATGGATTGG GGAAACTGAC AGTGAATCTG CTGACCTGCA GAAGGGATGG GCATCTGTAC    5880
AGGTATGGAC TTGGATGAAC ACATTGTTTT GTTATTTTAC TTTGCACCAT ACACAGCGTC    5940
TAGTTGTATC GTAATAATCA TGGTAGGGAA ATTTCTTATT TAGAGAAAGT TGTTATAATC    6000
AATGCATTTG TAGGTGAAGT AAATTCTGAA TTGTATATGA AACGTGTCTA ATAGTGTTTC    6060
GAAATAACAG AGTATTCCAA GGACAGTGCT TTACGACAAG AAGACAGGGA CACATCTACT    6120
TCAGTGGCCA GTGGAAGAAA TTGAAAGCTT AAGAGTGGGT GATCCTACTG TTAAGCAAGT    6180
CGATCTTCAA CCAGGCTCAA TTGAGCTACT CCGTGTTGAC TCAGCTGCAG AGGTTTGTTG    6240
CGTTACTTTT GTTTAAATT ACAAACACGC GCTTAATCTG CAGTCCCAAA ACTTGTTTAG    6300
CTATTGTGCA GTTGGATATA GAAGCCTCAT TTGAAGTGGA CAAAGTCGCG CTTCAGGGAA    6360
TAATTGAAGC AGATCATGTA GGTTTCAGTT GCTCTACTAG TGGAGGTGCT GCTAGCAGAG    6420
GCATTTGGG ACCATTTGGT GTCATAGTAA TTGCTGATCA ACGCTATCT GAGCTAACGC    6480
CAGTTACTT TTACATTTCT AAAGGAGCTG ATGGTCGTGC AGAGACTCAC TTCTGTGCTG    6540
ATCAAACTAG GTTGCTTTT CTATCTGGCA CAATTAATTT GTCCTTGTAA AATGGAGATG    6600
GATAAAAGTA GCGGGTTGTT GATCTGATAT ATGCAGATCC TCTGAGGCTC CGGGAGTTGG    6660
TAAACAAGTT TATGGTAGTT CAGTACCTGT GTTGGACGGT GAAAACATT CAATGAGATT    6720
ATTGGTAAGT GATAATGATT CCCTTATTTT ACCTTGATTT TATTCCATTT CTTCACTTCA    6780
CAATAATTAA AGTACTTGGC AGTTGCATTT GAGTAAAAGG TTTTTATAA ACTGAATTTT    6840
AGGTGGATCA CTCAATTGTG GAGAGCTTTG CTCAAGGAGG AAGAACAGTC ATAACATCGC    6900
GAATTTACCC AACAAAGGCA GTAAATGGAG CAGCACGACT CTTTGTTTTC AACAATGCCA    6960
CAGGGGCTAG CGTTACTGCC TCCGTCAAGA TTTGGTCACT TGAGTCAGCT AATATTCAAT    7020
CCTTCCCTTT GCAAGACTTG TAATCTTCTT TATTTCGTTT TTTTTTCTT TTTCATTTGA    7080
AGGTTATTTC ACCGACGTCC CATCAAGAAA GGGAAGAGGG AGATCAATAT ATGTAGTGTT    7140
ATTCGCCCTA CCTTAGGATT AGATGTCATC TAGCAATGTC AAATCTAGTA GAGTATACAA    7200
TGTATGGGTT CCTGGAAACC GAGTAGAGCT TACCTGGATT CTATGTAAAC TAAGAAAGCT    7260
CAGCAAATAT ATGTACAAAT AATTTACAGA AACAACTTGG GAATGTTGAC AAACTTGATT    7320
ATTTTTTCTT TTATATAACT AGTAATAACG GAAAGCTCTC CGCAATCTCG TTGAGCAAAA    7380
GTATAAATGG TTACGAGCCA CCTAAATATT TTTGTTCAAC GAGATTGGAA TTGGAGCTTA    7440
TTATACACAA CATATACAAC AATGATTCAT CTTCTAACTC ATACAATTCT ATACGTAAGG    7500
TCGAAGTTAG GAGGGAGTGA GCAACTTGGT AAAAAGTATA TGGTATAAGT AAGATATTTT    7560
TAAATGTATT ATGTATCAGT TGTACTCAAT CAAAGAGCGG ATAAATACAA TTGATACAAT    7620
ATACAAAATA GTTATGCACT AAATAATAAA TAGAGGATAA AATGTAAAAT AAATACAAAA    7680
TATAATTCTC TCGATCTCGC TCCCGTCTCT CCTCTCTCGA TCTCACTCAT CTCTCTTCTC    7740
TTAATATGTA TTCATTTTAA TACAAATTAG TTTCTATTTG TATTTTTCT TCAAAATTCA    7800
CGAAAAAAAA TATATATAAA TATAAATGCA TAGCGAACAA GAATATTATT ATGAATCATA    7860
```

```
AATAATGAAA CTGTAGTTAT GGAATACTTT TAAGGGTTAA TGTTTGTTGT TTTTGAAATT    7920
TCCCCTCTTG AAGCCCTTAA GTGCAAATCT TGAATCCACT ATGAATATGA TTCATTCTTT    7980
ATACATATAC AATAATAATG ATACATTTCT ATTTACGAAT GATATAATTC CCGTACAAAT    8040
AAATTTAGAG TTACAAAAGA AGATCAGCCC AGCCCATCTA ATTCAAGCCT CGTGGGCCAA    8100
GAAATTTAAT GAGCTAAGGA AGGTTGGCCC TTTATTTGAA AGTGCCTAAA TTGTTCAACT    8160
CAACCTAATT TTAGAAGGGC CACAAACTGG GGGGTTAGCA TTTTTTTCCT TTTTAAACTT    8220
AAAGCTCTAT ACCATCAAGT AAATGAGACT ATTTTCAAAT CAAATATGGT AACAATGGTG    8280
TTTTTTCAAT AACACTAACA AAAATTTGT ATGATTAACA TGTACCTTGG ATACTACATG     8340
CCCAAGCTAC ATGTATATGT TGTGATGCAT TCCAAATATG CAAGCGAGAT AAGAGCGACC    8400
AAGATGGGTG GGAGGCGAGG GCTTGGAATT TGTTTATATA TCCTAGATAC ATGCGAATCC    8460
ATTTGAATGA AGTCCTTCTA GAATAAATAG ACGTATCGAA ATGCACCAAA ATCTAGTAAG    8520
ATTTGTAATG TTACAGCATA ACGTGCATCT AAGTAATTAG CTAGCTCATA CACTAGTGAG    8580
ATCCTTTTAG TTACCGTATA TAAATAGTTT TGACCCATGG GACGATCCTA ACCTGTTCCC    8640
GATCAAGACT CAAGGGCTTA TAAGTCCTAA TGTTGAATGG TCTTGTAAAT CCTATCACAA    8700
CCATACCCCA ATACCGAGTT GGGTTGGACC GGCTCCATGG GCTTAGCAAA CTTGACATA     8760
TCTACACATA ATGGAACAAA TGAAAAAAAA AATACGAAAT GAAATTATTT TTAAAACAAT    8820
AAAGACAATA TTTTTTAGA GAAAGTTACA AAATTATATA CAACTTAATA TTATTATATC     8880
CTCTAAAAAT TCCTATCTTT GAATTAAATA CAAAAATTTC CTTTTCCTT CTCTCTCTTT     8940
TTTCATCCGG ATACATCACT CGACCTCTAT GAAATACACC ACAATTTGT TTGTGTATAC     9000
TAATATGGTA GAAATATTAT TACCGATACA TAACCCCAAT TATTTCAAAT ATAATTATAT    9060
TAGTGATACA CAACTTGTTT ATTGTTTGTT ATATATATAG AGCGAATGAG CAATGTATCC    9120
ACAAGTTTTG AAAAATCCAA AATCATTTAT TTAAAAAACT TTTAAGATAA TGTGTAATTA    9180
ACGCCTAAAA ACTATTGAGG TTTCTGTATT TTGTATTGTA TTCCTTTTAA GGAAAAATAT    9240
ATAATAACAA ACTATTAATT CAAATTAAAT GTTATATACA CAATTTGATT TAACCTGTAG    9300
CAAAATATTT TCATTCGCCT CTCTCCCTAG GTTTCTCACT CGCCACTCTC GCTTTTATAC    9360
AAACACAAAT GTATAAAATG TGTTTGTGTT TGTATAAAGC GAGAGAAAAT GTATATACAA    9420
ATATGAATAC ATATATTTTC GTCCTATATA CTTATAATGA TACAAATACA GATCTTTTCC    9480
TATCCAGTTC ACTTTTGTCT TTCTCACTTT ATACAAACAC AAATTATACA AATTACAATG    9540
TATAATTATT GTTGCATAAA GCGAGAGAGA GATTCGATAT ACAAATAGTT TATTTCGATT    9600
CAATTATATA TAAATTCAAA TTTTATGCAG ATATGCAAAC AAATAAAATA AAATTTGAGA    9660
GGCTGTCAGC GATTTATGCC AACGATTTAT ACAAATGACC TACCACGAA ATTATACAAA     9720
TCTGAAGCAT TGCCAGCGAG CTATACAATC TGATGCTCCA TAACAAACAT AAAATTTATC    9780
ATGGAACGTA AATATACAAA CTATAACTAT AACATTCAAA TATAATTTTT ATGTTTGCCA    9840
TATATAAAAA TTGATCTAAG CCTTTTGAAC TATCCGATGT CAATAGTTTC ACCCAGATAG    9900
CCATTAATAT CAAAGTTCAG GCCCAGATCA TTGGGATGAA TTTGGGCCTA TATTGTGGAC    9960
CGTGACTCGA AAAACACCTA ATGCTACAGG CTACACCAAA TTGATTAATG ATTTCTCATC   10020
TTCTGAAAAC AAAATAAATT TATAATTTTT ATATTACATA AATATTTTTT TCCCGCTAAA   10080
TTCAAAGTAG TCAAACATTC AAAAATATTT AAACTGATGA TCAGAGCTCA AGTCACCTTT   10140
TCATTTATAC TATTATTATA TTTTTTTAAT ATTAGAGACA AAAAGAAAA GCTCTCATAT    10200
TAAATAATAA AATATATAGA ATTGACAGAA CCATTGACC ATTCTTCTCA TAGTTAAAAT    10260
```

```
AGTATATAAT TGGGCTCGAC TTTATATAAA ATTCTGATAT ATTATTTAAT ATTCTTCTTT    10320

GCTTTTCCTT TTCTGCATTA CTTTTTTTTT CCATTTAAAT AATAATACAG GTTTATGGGT    10380

ATTATAAAAC GGATCC                                                    10396
```

( 2 ) INFORMATION FOR SEQ ID NO:6:

( i ) SEQUENCE CHARACTERISTICS:
            ( A ) LENGTH: 22 amino acids
            ( B ) TYPE: amino acid
            ( C ) STRANDEDNESS: single
            ( D ) TOPOLOGY: linear ( i i ) MOLECULE TYPE: protein ( v ) FRAGMENT TYPE: N-terminal ( v i ) ORIGINAL SOURCE:
           ( A ) ORGANISM: Lycopersicon esculentum ( x i ) SEQUENCE DESCRIPTION: SEQ ID NO:6:

```
Tyr Ala Trp Ser Asn Ala Met Leu Ser Trp Gln Xaa Thr Ala Tyr Xaa
1               5                   10                  15

Phe Gln Pro Gln Lys Asn
            20
```

( 2 ) INFORMATION FOR SEQ ID NO:7:

( i ) SEQUENCE CHARACTERISTICS:
            ( A ) LENGTH: 22 amino acids
            ( B ) TYPE: amino acid
            ( C ) STRANDEDNESS: single
            ( D ) TOPOLOGY: linear ( i i ) MOLECULE TYPE: protein ( v ) FRAGMENT TYPE: internal ( v i ) ORIGINAL SOURCE:
           ( A ) ORGANISM: Lycopersicon esculentum ( x i ) SEQUENCE DESCRIPTION: SEQ ID NO:7:

```
Gly Gln Trp Leu Leu Thr Ile Xaa Ser Lys Ile Gly Lys Thr Gly Val
1               5                   10                  15

Ala Leu Val Tyr Glu Thr
            20
```

( 2 ) INFORMATION FOR SEQ ID NO:8:

( i ) SEQUENCE CHARACTERISTICS:
            ( A ) LENGTH: 13 amino acids
            ( B ) TYPE: amino acid
            ( C ) STRANDEDNESS: single
            ( D ) TOPOLOGY: linear ( i i ) MOLECULE TYPE: protein ( v ) FRAGMENT TYPE: internal ( v i ) ORIGINAL SOURCE:
           ( A ) ORGANISM: Lycopersicon esculentum ( x i ) SEQUENCE DESCRIPTION: SEQ ID NO:8:

```
Met Xaa Xaa Xaa Val Asp Phe Tyr Pro Val Ser Thr Lys
1               5                   10
```

( 2 ) INFORMATION FOR SEQ ID NO:9:

( i ) SEQUENCE CHARACTERISTICS:

(A) LENGTH: 17 amino acids
(B) TYPE: amino acid
(C) STRANDEDNESS: single
(D) TOPOLOGY: linear (ii) MOLECULE TYPE: protein (v) FRAGMENT TYPE: internal (vi) ORIGINAL SOURCE:
(A) ORGANISM: Lycopersicon esculentum (xi) SEQUENCE DESCRIPTION: SEQ ID NO:9:

```
Met Leu Tyr Thr Gly Asp Thr Xaa Xaa Xaa Val Gln Val Gln Asn Leu
 1               5                  10                  15
Ala
```

(2) INFORMATION FOR SEQ ID NO:10:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: protein (v) FRAGMENT TYPE: internal (vi) ORIGINAL SOURCE:
(A) ORGANISM: Lycopersicon esculentum (xi) SEQUENCE DESCRIPTION: SEQ ID NO:10:

```
Met Asn Asp Pro Asn Gly Pro Leu Tyr
 1               5
```

(2) INFORMATION FOR SEQ ID NO:11:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:11:

GCTCGAGTGT ACGTACCG                                              18

(2) INFORMATION FOR SEQ ID NO:12:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:12:

AATTCGGTAC GTACACTCGA GC                                         22

(2) INFORMATION FOR SEQ ID NO:13:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

( x i ) SEQUENCE DESCRIPTION: SEQ ID NO:13:

CATTCTAGAA GATAGAGGAA TG　　　　　　　　　　　　　　　　　　　　　　　　　　　22

( 2 ) INFORMATION FOR SEQ ID NO:14:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

TGAAGCTTAA TCAACCTGTA AATCCC　　　　　　　　　　　　　　　　　　　　　26

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

GAGCATGCTC CGTCCTGTAG　　　　　　　　　　　　　　　　　　　　　　　　　20

( 2 ) INFORMATION FOR SEQ ID NO:16:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

TTGCATGCCT GCAGTTGTTT GCCTCCCTGC TG　　　　　　　　　　　　　　　32

( 2 ) INFORMATION FOR SEQ ID NO:17:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

AACTGCAGAA TGGAGCAGCA CGACTC　　　　　　　　　　　　　　　　　　26

1

INVERTASE GENES AND USES THEREOF

This is a continuation of application Ser. No. 07/771,331, filed Oct. 4, 1991, now abandoned, which is a continuation-in-part of U.S. patent application Ser. No. 07/660,344 to Fitzmaurice et al., filed Feb. 22, 1991, now abandoned, "NOVEL INVERTASE GENE(S) AND USES THEREOF". The subject matter of U.S. patent application Ser. No. 07/660,344 is incorporated herein in its entirety by reference thereto.

FIELD OF THE INVENTION

The present invention is related to methods for improving the value of commercial varieties of plants by altering the phenotype of the plants and is related to the plants that exhibit the altered phenotype. In particular, this invention is related to transgenic plants that have been genetically engineered to express heterologous DNA by operatively linking such DNA to regulatable promoters. This invention provides promoters for achieving such regulated expression in plants.

This invention is also related to transgenic tomato plants that have been genetically engineered to produce tomatoes that exhibit an altered solids content and an altered ratio of soluble solids to insoluble solids. Specifically, the solids content of the tomato fruit is altered by modifying the timing and level expression of vacuolar invertase in ripening tomato fruit.

BACKGROUND OF THE INVENTION

The solids content and ratio of soluble to insoluble solids is a major factor affecting the profitability of commercial tomato processing operations. The solids content is also important in determining the flavor and marketability of fresh market tomatoes.

Tomato solids include a water-soluble and a water-insoluble fraction. The insoluble solids in tomato fruit are primarily components of the cell wall and are responsible for the viscosity of processed tomato pulp. The water-soluble fraction contains the hexoses, glucose and fructose, which constitute more than 90% of this fraction. Measurement of the content of these two sugars in a given fruit defines the "soluble solids content" of that fruit for commercial cultivars.

The hexoses in ripened tomato fruit are produced by hydrolysis of sucrose that is transported from the leaves and by hydrolysis of accumulated starch, which is also derived from sucrose transported into the fruit during fruit development. The enzyme which catalyzes the conversion of sucrose to the hexoses glucose and fructose, is beta-fructofuranosidase, commonly called invertase. Plants, including tomato, have at least two invertase activities, a soluble invertase located in the vacuole and an insoluble invertase activity bound to the cell wall.

There are characteristic differences in the distribution of sugars and the activity of invertase in plant tissues and in the fruit at different stages of ripeness. Invertase activity increases in tomato fruit during ripening. There are also differences in the activity profile of invertase and in the solids content among the fruits of different tomato species. For example, the fruit of *Lycopersicon pimpinellifolium*, which is a wild tomato species, is richer in invertase and expresses it earlier during ripening than the cultivated tomato species, *Lycopersicon esculentum*.

Tomato growers and processors strive to attain a tomato fruit that reflects the specific balance of soluble solids content and insoluble solids content desired for a particular tomato product. Traditionally, efforts to improve or alter this balance have focussed on the development of hybrid plants by crossing species of cultivated tomatoes with wild tomato species that produce fruit with a higher soluble solids content than the cultivated varieties. The hybrids, however, also tend to possess undesirable traits of the wild species.

There is a need, therefore, to produce improved versions of cultivated species of tomato, such as *L. esculentum*, that exhibit desirable traits of the wild species, such as a higher ratio of soluble solids to insoluble solids and a higher level of soluble solids, but that do not also have the undesirable traits of the wild species. It would also be desirable to have the ability to produce cultivated plants that have a selected specific level of soluble solids content and ratio of soluble to insoluble solids content desired for a particular tomato product.

Therefore, it is an object of this invention to provide transgenic tomato plants that express invertase earlier during ripening and express higher levels of invertase during fruit ripening than cultivated non-transgenic plants.

It is also an object of this invention to provide a means for regulating and altering the levels and ratios of soluble to insoluble solids in the fruit of cultivated tomato plants in order to select a specific level of soluble solids content and ratio of soluble to insoluble solids content desired for a particular tomato product.

SUMMARY OF THE INVENTION

Transgenic tomato plants that have fruits with solids contents and ratios of soluble to insoluble solids that differ from non-transgenic plants of the same species are provided. In particular, transgenic tomato plants that produce fruits that have improved taste and processing properties are provided.

Methods for increasing the soluble solids content of tomato fruit produced by a tomato plant by introducing DNA constructs that contain DNA encoding an invertase are provided. In accordance with the methods, tomato plants are transformed with the constructs by techniques well-known in the art and result in transgenic plants that express different levels of invertase from the non-transgenic plant and produce fruits with altered solids contents.

In particular, a DNA construct encoding tomato fruit invertase under the control of a promoter that is functional in plants is introduced into cells of a tomato plant, the cells containing the construct are cultured under conditions that result in the development of transgenic tomato plantlets, and the plantlets are grown into tomato plants under conditions such that the DNA encoding tomato fruit invertase is expressed. The resulting transgenic plants produce fruit that has a soluble solids content and ratio of soluble solids to insoluble solids that differ from the non-transgenic plant. The soluble solids content and ratio of soluble to insoluble solids in tomato fruit is achieved by altering the timing of expression of an invertase and level of such invertase in the vacuoles. The level of and timing of expression of vacuolar invertase in the plants is altered by increasing or decreasing expression of the gene encoding the invertase and by changing the time during the development of the plant, particularly the fruit, that the invertase is expressed.

In certain preferred embodiments, DNA encoding an invertase that is secreted and transported to the vacuole is introduced into tomato plants. The DNA encoding the invertase is operatively linked to a promoter recognized by the plant RNA polymerase II, and, if the DNA encodes an invertase that is not a vacuolar invertase. DNA encoding the invertase is operatively linked to DNA that encodes vacuolar targeting sequences.

Promoters for achieving regulated expression of heterologous DNA in plants and transgenic plants that express such heterologous DNA are provided. The promoter is preferably a promoter, such as a native Lycopersicon invertase promoter, a constitutive promoter, such as the CaMV 35S promoter, or a developmentally regulated promoter, that confers fruit specificity and appropriate temporal control on the expression of the DNA encoding the invertase.

Transgenic tomato plants that contain tomato fruit invertase under the transcriptional regulation of native regulatory sequences express higher levels of invertase than the non-transgenic plant, by virtue of the additional copy of the gene. When recombinant tomato plants containing tomato fruit invertase under the transcriptional regulation of heterologous control sequences are grown, both the quantity and the timing of tomato fruit invertase production can be altered. The manner in which invertase expression is altered is a function of the regulatory sequences to which the invertase-encoding DNA is operably linked. In preferred embodiments, the regulatory sequences, particularly the promoter, are selected such that the onset of expression of recombinant tomato fruit invertase commences at an earlier stage of development of the tomato fruit than would otherwise occur when the same plant does not express the recombinant invertase.

In preferred embodiments, DNA encoding regulatory regions upstream from the translation start codon of the structural invertase genes in the genomic clones from L. esculentum and L. pimpinellifolium and from other developmentally regulated genes are provided. DNA constructs made by fusing tomato invertase gene sequences with homologous or heterologous regulatory sequences are also provided. These constructs may be used to produce L. esculentum transgenic plants, or other transgenic plants, that express heterologous genes in a developmentally regulated manner.

In particular, these constructs may be used to produce L. esculentum transgenic plants, or other transgenic plants, that express invertase under the control of the regulatory regions such that the levels of invertase expressed and the timing of expression of invertase differ from nontransgenic plants and the levels of soluble and insoluble solids in the transgenic tomato fruits differ from the fruits of nontransgenic plants.

In certain embodiments, DNA sequences which are fruit-specific developmentally controlled regulatory sequences, other than invertase regulatory sequences, are provided. DNA constructs in which these regulatory regions are operably linked to genomic or cDNA encoding invertase are also provided. In the most preferred embodiments, the regulatory regions are selected such that invertase is expressed to a greater extent and earlier during fruit ripening than in non-transgenic plants.

In preferred embodiments, the DNA encoding the invertase is operably linked to a developmentally regulated promoter selected so that the onset of expression of recombinant tomato fruit invertase begins at about the breaker stage of development of tomato fruit and continues until the tomato fruit has reached the red stage. The tomato fruit of such transgenic plants should have a soluble solids content higher than the soluble solids content of tomato fruit produced by equivalent non-recombinant tomato plants. Typically, the soluble solids content of the tomato fruit will be increased by at least about 0.5% compared to that produced by non-modified tomato plants. The preferred increase in soluble solids content will be about 1% or more.

In most preferred embodiments, DNA constructs containing the DNA encoding invertase from L. esculentum or L. pimpinellifolium operatively linked to DNA encoding the regulatory region of invertase gene from L. pimpinellifolium or from other developmentally regulated genes that are expressed early during fruit ripening are introduced into a cultivated tomato species, such as L. esculentum, to produce transgenic plants that have an altered phenotype manifested as increased production of invertase earlier in fruit development than in the non-transgenic plants. Such transgenic tomato plants can also be used as a source for the production of substantially pure tomato fruit invertase.

In other embodiments, transgenic tomato plants in which the DNA encoding a mature invertase is operably linked to vacuolar targeting signals and to developmentally regulated promoter regions isolated from plants of the genus Lycopersicon, and constructs made from these sequences and heterologous DNA sequences for the purpose of producing transgenic tomato plants are provided.

In accordance with other embodiments, transgenic plants that express lower levels of soluble solids than the non-transgenic plant and methods for decreasing the soluble solids content of tomato fruit are provided. Production of tomato fruits that have decreased soluble solids content is desirable when one seeks to obtain tomato fruit having increased insoluble solids content. Cultivars capable of producing fruit with an increased insoluble solids content are of commercial value for the production of tomato products with high viscosity, such as tomato paste.

In order to effect such reduction in soluble solids, transgenic plants that contain DNA constructs encoding an invertase operatively linked to a promoter such that anti-sense tomato fruit invertase mRNA or a truncated form of tomato fruit invertase is expressed are provided. Plants that express anti-sense invertase mRNA or truncated forms of the protein, should produce plants in which invertase produced in the plant, particularly during fruit development, is substantially less than the amount of invertase produced when the plant does not express anti-sense invertase mRNA or truncated form of invertase. The resulting fruit should have reduced levels of soluble solids.

In preferred embodiments, the level of soluble solids in the fruit is reduced by preparing transgenic plants that express anti-sense invertase mRNA. Anti-sense RNA forms double-stranded RNA with the mRNA produced from the endogenous gene, thereby interfering with translation of the endogenous mRNA (see, e.g., Lichtenstein (1988) *Nature* 333:801–802). To inhibit expression of the targeted gene, the anti-sense RNA can be less than full-length copy of the targeted mRNA (see, e.g., Grum et al. (1988) *Nuc. Acids Res.* 16:4569–4581 and references cited therein).

Decreased levels of soluble solids in tomato fruit, can be achieved by expressing, starting at the breaker stage and continuing through the ripe stage of fruit development, an anti-sense copy of part, or all, of the tomato fruit invertase mRNA in tomato fruit. As a result, reduced amounts of invertase are produced, and sucrose, which ordinarily would have been converted to glucose and fructose, is converted into cell wall components.

In accordance with yet another embodiment, a tomato fruit produced by a transgenic tomato plant of the genus Lycopersicon, which is derived from a transgenic tomato plantlet which contains a recombinant construct encoding anti-sense tomato fruit invertase mRNA, such that the total soluble solids content of said fruit is at least about 0.5% lower than the soluble solids content of fruit produced by a tomato plant which does not contain said recombinant construct, and such that the total insoluble solids content of said fruit is at least 0.5% higher than the insoluble solids content of fruit produced by a tomato plant which does not contain the recombinant construct is provided.

In other embodiments, DNA encoding proteins and sequences that direct such proteins to the vacuoles are also provided. Such DNA encodes proteins that include signal sequences and specific C-terminal precursor peptide sequences, which target or sort proteins to the vacuole. In preferred embodiments, such proteins include the tomato fruit invertase signal sequence, which includes amino acids 1–30 of Sequence ID No. 1, and an invertase carboxyl-terminal precursor or propeptide sequence, that includes residues 606–612 of Sequence ID no. 2, which are required for vacuolar targeting.

In accordance with a still further embodiment, methods for identifying the presence of invertase-encoding nucleic acid sequences by contacting a sample containing RNA or single-stranded DNA with a probe containing at least a portion of the nucleic acid sequence set forth in Sequence ID No. 2 are provided. The probe is hybridized to the DNA or RNA sample under conditions which are selected to provide a low background level of hybridization and a high level of specific hybridization. Hybridizing sequences, which exhibit substantial homology to the probe, encode all or a portion of a protein that has homology to Lycopersicon invertase. DNA that encodes proteins that also exhibit invertase activity are, for purposes herein, invertase.

In preferred embodiments, isolated, substantially pure DNA encoding vacuolar invertase that have amino acid sequences substantially identical to the vacuolar invertases of the commercial tomato species, L. esculentum, and the wild tomato species L. pimpinellifolium, are provided. Genomic and cDNA clones that encode the vacuolar invertase from each species are provided.

In accordance with other embodiments, antibodies that specifically react with tomato fruit invertase epitopes are provided. Methods for measuring the tomato fruit invertase content of a given sample by contacting the sample with the antibodies are provided.

In accordance with still further embodiments, methods for determining the tomato fruit invertase content of a sample; methods for identifying the presence of invertase-encoding sequences in a cDNA expression library; methods for the recombinant production of tomato fruit invertase; methods for modulating the expression of tomato fruit invertase in solanaceous plant species; and methods for targeting protein product(s) expressed from heterologous genes by recombinant plants to the vacuoles are provided.

BRIEF DESCRIPTION OF THE FIGURES

FIG. 1 presents aligned restriction enzyme maps of the inserts of L. escultentum genomic clones λEL1, λEL2, and λEL3, and L. pimpinellifolium genomic clones λPI.1, λPI.3, and λPL6. Dotted lines indicate the regions from which SEQ. I.D. No. 3 and No. 5 were determined.

FIG. 2 presents schematic diagrams of the L. pimpinellifolium and L. esculentum fruit vacuolar invertase genomic sequences (SEQ. I.D. Nos. 3 and 5). The dotted lines indicate unsequenced regions. The nucleotide positions at which the TATA box, transcription start site (ATG), and translation stop site (TAA) begin are indicated above each diagram. The arrows at the bottom of the figure indicate the locations at which the sequences from the two species differ, and the position of the TCT insertion found in only some of the genomic and cDNA clones.

FIGS. 6A and B present diagrams illustrating the composition of constructs HDC/GUS.1 and HDC/GUS.2.

FIGS. 8A–C present diagrams illustrating the composition of constructs 35S/3-L1, 35S/3-L1(−), and 35S/3-L1(P).

DESCRIPTION OF THE PREFERRED EMBODIMENTS

Definitions

Figure 3A:
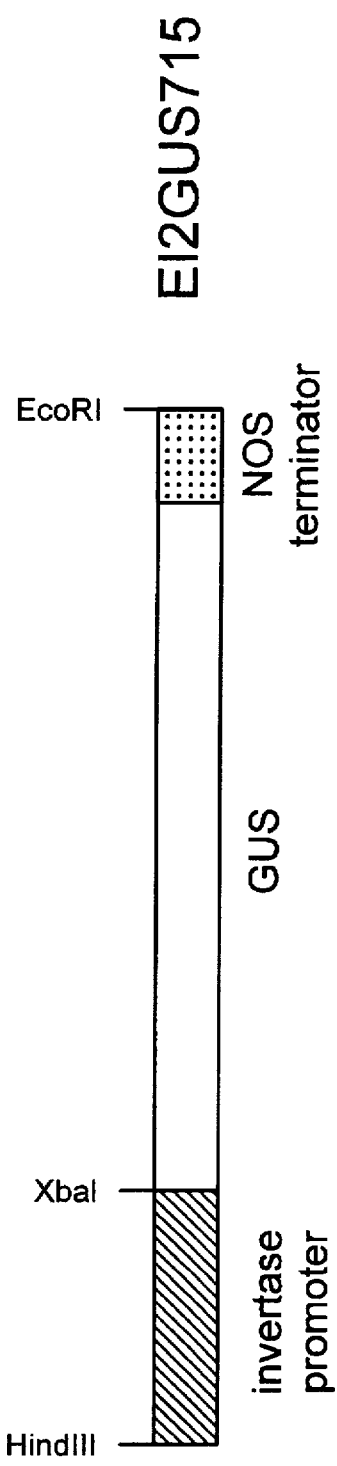
FIGS. 3A and 3B present diagrams illustrating the composition of constructs EI2GUS715 and EI2GUS1100.

Unless defined otherwise, all technical and scientific terms used herein have the same meaning as is commonly understood by one of skill in the art. All publications mentioned herein are incorporated by reference thereto. All U.S. patents and publications cited herein are incorporated in their entirety by reference thereto.

The amino acids, which occur in the various amino acid sequences appearing herein, are identified according to their well-known three-letter or one-letter abbreviations. The nucleotides, which occur in the various DNA fragments described are designated using the standard single-letter designations used routinely in the art.

As used herein, breaker stage refers to the stage in fruit ripening at which the color of the fruit exhibits a definite break in color from green to tannish-yellow, pink or red, on not more than about 10% of the surface of the tomato fruit. Commercial tomato fruit passes through several well-defined stages of development. Early in the maturation process, when substantially the entire surface of the tomato fruit is green, the tomato fruit is in the "green" stage of development. This is followed by the "breaker" stage of development. Then, when more than 10%, but less than about 30% of the fruit surface, in the aggregate, shows a definite change in color from green to tannish-yellow, pink, red, or a combination thereof, the fruit is said to be at the "turning" stage. When more than 30%, but less than about 60% of the fruit surface, in the aggregate, is pink or red, the fruit is said to be at the "pink" stage, which is also the 3-inch intermediate stage, of development. When more than 60%, but less than about 90% of the fruit surface, in the aggregate, is pinkish-red or red, the fruit is said to be at the "light red" stage of development. Finally, when more than 90% of the fruit surface in the aggregate is red, the fruit is said to be in the "red" stage of development.

As used herein, invertase refers to an enzyme that hydrolyses sucrose to fructose and glucose and encompasses any protein that exhibits this activity in plants. The biological activity of invertase may be measured by one of several bioassays well-known in the art, such as that of Nelson, J. Biol. Chem. 153:375–380 (1944), in which the sugars liberated by invertase activity are chemically quantified. Preferred invertases are those that, upon expression in a tomato plant, are transported through the processing pathway of the plant and targeted to the vacuoles. Tomato fruit vacuolar invertase is among those preferred herein.

As used herein, mature protein, such as mature invertase, refers to processed protein from which the signal and processing sequences have been cleaved. As used herein, mature invertase refers to invertase that has been processed.

As used herein, a precursor protein or peptide refers to a protein that includes a leader or signal sequence that effects transport of the protein through plant processing pathways to yield mature protein.

As used herein, a signal or leader sequence, which expressions are used interchangeably, refers to a sequence of amino acids that directs transport of the translation product through the processing pathway of the host and results in the generation of a mature protein. A signal sequence refers to a sequence of hydrophobic amino acids at the amino terminus of the protein to which it is linked. DNA encoding a signal Sequence is located downstream (3' in the direction of transcription) from the ATG start codon and upstream (5') from the DNA that encodes the structural gene. In addition, the signal sequence includes one or a sequence of amino acids that is recognized by one or more host cell proteases. Such sequences-may be interposed between the signal sequence and the protein, whereby, upon recognition of the processing site by the appropriate host cell protease, removal of the signal sequence may be effected. The signal sequence, processing sites and protein are referred to as a precursor protein, and the processed protein is referred to as the mature protein.

As used herein, processing signals also include sequences that are required for targeting proteins to selected plant organs, such as the vacuoles.

As used herein, a vacuolar targeting sequence effects transport of the protein to which it is linked to the vacuoles. If such sequence is absent and no other targeting sequence is present, the protein is directed to the default pathway and ultimately to the cell wall.

The processing sequences, signal sequences and targeting sequences for use herein are those that are sufficient for directing invertase encoded by the DNA to which such sequences are linked to the vacuoles of the plant host in which the invertase is expressed. Any peptide or DNA encoding such peptide that effects proper processing and vacuolar targeting in plant hosts is contemplated for use herein. The preferred processing and targeting sequences for use herein are those that effect proper secretion, processing and targeting of the *L. esculentum* vacuolar invertase.

As used herein, precursor invertase refers to unprocessed invertase that includes sequences that direct the protein through the processing pathways of the plant. Such invertase includes the signal sequences and vacuolar targeting or sorting sequences. In the plant, signal sequences promote uptake of the protein into the endoplasmic reticulum (ER), of the plant cells. The enzymes are synthesized on the rough endoplasmic reticulum (ER) and their transport is mediated by the Golgi complex. In the absence of a targeting or sorting sequence in the protein, the proteins are secreted by default. In the presence of a targeting or sorting signal, such as the vacuolar targeting sequence present at the C-terminus of vacuolar invertase, the invertase is secreted to the vacuole. Preferred signal Sequences and targeting sequences include, but are not limited to the vacuolar invertase signal sequence and carboxyl-terminal peptide. Other such sequences that are active in plants, such as the carboxyl-terminal propeptide (CTPP) of the barley lectin proprotein, the β-1,3-glucanase CTPPs of *Nicotiana tabacum* and *N. plumbaginifolia*, may also be used.

As used herein, exogenous invertase refers to invertase that is encoded by DNA that is introduced into the plant and is expressed in the plant in addition to endogenous invertase.

As used herein, heterologous or foreign DNA and RNA are used interchangeably and refer to DNA or RNA that does not occur naturally as part of the genome in which it is present or which is found in a location or locations in the genome that differ from that in which it occurs in nature. Heterologous nucleic acid is generally not endogenous to the cell into which it is introduced, but has been obtained from another cell or prepared synthetically. Generally, although not necessarily, such nucleic acid encodes RNA and proteins that are not normally produced by the cell in which it is expressed. Any DNA or RNA that one of skill in the art would recognize or consider as heterologous or foreign to the cell in which it is expressed is herein encompassed by heterologous DNA. Examples of heterologous DNA include, but are not limited to, DNA that encodes exogenous invertase. Heterologous DNA and RNA may also encode RNA or proteins that mediate or alter expression of endogenous DNA by affecting transcription, translation, or other regulatable biochemical processes.

As used herein, operative linkage of heterologous DNA to regulatory and effector sequences of nucleotides, such as promoters, enhancers, transcriptional and translational stop sites, and other signal sequences refers to the relationship between such DNA and such sequences of nucleotides. For example, operative linkage of heterologous DNA to a promoter refers to the physical relationship between the DNA and the promoter such that the transcription of such DNA is initiated from the promoter by an RNA polymerase that specifically recognizes, binds to and transcribes the DNA in reading frame.

As used herein, isolated, substantially pure DNA refers to DNA fragments purified according to standard techniques employed by those skilled in the art, such as that found in Maniatis et al. ((1982) *Molecular Cloning: A Laboratory Manual*, Cold Spring Harbor Laboratory Press, Cold Spring Harbor, N.Y.).

As used herein, expression refers to the process by which nucleic acid is transcribed into mRNA and translated into peptides, polypeptides, or proteins. If the nucleic acid is derived from genomic DNA, expression may, if an appropriate eukaryotic host cell or organism is selected, include splicing of the mRNA.

As used herein, vector or plasmid refers to discrete elements that are used to introduce heterologous DNA into cells for either expression of the heterologous DNA or for replication of the cloned heterologous DNA. Generally, if such vectors and plasmids include origins of replication that function in the particular host cell into which the vector or plasmid is introduced, the vector, or plasmid, remains episomal. Other vectors, such as those derived from retroviruses and those derived from the Agrobacterium Ti plasmid, when introduced into an appropriate host cell, integrate into the host cell DNA. In addition, other vectors, such as the RNA virus satellite tobacco mosaic virus (STMV), remain episomal.

As used herein, expression vector includes vectors capable of expressing DNA fragments that are in operative linkage with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA.

As used herein, a promoter region refers to the portion of DNA of a gene that controls expression of DNA to which it is operatively linked. The promoter region includes specific sequences of DNA that are sufficient for RNA polymerase recognition, binding and transcription initiation. This portion of the promoter region is referred to as the promoter. In addition, the promoter region includes sequences that modulate this recognition, binding and transcription initiation activity of the RNA polymerass. These sequences may be cis acting or may be responsive to trans acting factors. Promoters, depending upon the nature of the regulation, may be constitutive or regulated. A constitutive promoter is always turned on. A regulatable promoter requires specific signals to be turned on or off. A developmentally regulated promoter is one that is turned on or off as a function of development.

Appropriate expression vectors are well known to those of skill in the art and include those that are replicable in eukaryotic cells and/or prokaryotic cells. Such expression vectors may remain episomal or may integrate into the host cell genome. Expression vectors suitable for introducing heterologous DNA into plants and into host cells in culture, such as mammalian cells and methylotrophic yeast host cells, are known to those of skill in the art. It should be noted that, because the functions of plasmids, vectors and expression vectors overlap, those of skill in the art use these terms, plasmid, vector, and expression vector, interchangeably. Those of skill in the art, however, recognize what is intended from the purpose for which the vector, plasmid or expression vector is used.

As used herein, expression cassette refers to a DNA construct that includes sequences functional for the expression, and, if desired, processing and secretion of a mature protein in a selected host. Since such fragments are designed to be moved from vector to vector and into the host cell for both replication and expression, they are often referred to by those of skill in the art as "expression cassettes". Accordingly an expression cassette includes DNA encoding a promoter region, a transcription terminator region, and sequences sufficient for translation, as well as any other regulatory signals, such as those that effect proper processing of the expressed protein or peptide.

As used herein, the term DNA construct embraces expression cassettes and also includes DNA fragments that include more than one expression cassette.

As used herein, portions or fragments of the DNA constructs and expression cassettes are said to be operationally associated or operably linked when protein-encoding portions and regulatory regions are positioned such that expression, including transcription, translation and processing, of the protein-encoding regions is regulated by the DNA that encodes regulatory regions.

As used herein, reference to "downstream" and "upstream" refers to location with respect to the direction of transcription from the promoter which regulates transcription of the invertase-encoding fragment.

As used herein, transgenic plants refer to plants in which heterologous or foreign DNA is expressed or in which the expression of a gene naturally present in the plant has been altered. Such DNA is said to be in operative linkage with plant biochemical regulatory signals and sequences. Expression may be constitutive or may be regulatable. The DNA may be integrated into a chromosome or integrated into an episomal element, such as the chloroplast, or may remain as an episomal element. In addition, any method for introduction of such DNA known to those of skill in the art may be employed.

As used herein, wild type plant refers to plants that are of the same species or are identical to the transgenic plants, but do not contain DNA or RNA that encodes the heterologous gene that is expressed by the transgenic plant.

As used herein, a substantially homologous protein refers to a protein that is sufficiently similar to tomato vacuolar invertase to catalyze the hydrolysis of sucrose to glucose and fructose and to do so in the tomato plant.

As used herein, substantially homologous DNA refers to DNA that includes a sequence of nucleotides that is sufficiently similar to another such sequence to form stable hybrids under specified conditions.

It is well known to those of skill in this art, that nucleic acid fragments with different sequences may, under the same conditions, hybridize detectably to the same "target" nucleic acid. Two nucleic acid fragments hybridize detectably, under stringent conditions over a sufficiently long hybridization period, because one fragment contains a segment of at least about 14 nucleotides in a sequence which is complementary (or nearly complementary) to the sequence of at least one segment in the other nucleic acid fragment. If the time during which hybridization is allowed to occur is held constant, at a value during which, under preselected stringency conditions, two nucleic acid fragments with exactly complementary base-pairing segments hybridize detectably to each other, departures from exact complementarity can be introduced into the base-pairing segments, and base-pairing will nonetheless occur to an extent sufficient to make hybridization detectable. As the departure from complementarity between the base-pairing segments of two nucleic acids becomes larger, and as conditions of the hybridization become more stringent, the probability decreases that the two segments will hybridize detectably to each other.

Two single-stranded nucleic acid segments have "substantially the same sequence," within the meaning of the present specification, if (a) both form a base-paired duplex with the same segment, and (b) the melting temperatures of said two duplexes in a solution of 0.5 X SSPE differ by less than 10° C. If the segments being compared have the same number of bases, then to have "substantially the same sequence", they will typically differ in their sequences at fewer than 1 base in 10.

Methods for determining melting temperatures of nucleic acid duplexes are well known. See, e.g., Meinkoth and Wahl (1984) *Anal. Biochem.* 138:267–284 and references cited therein.

As used herein, a nucleic acid probe is a DNA or RNA fragment that includes a sufficient number of nucleotides to specifically hybridize to DNA or RNA that includes identical or closely related sequences of nucleotides. A probe may contain any number of nucleotides, from as few as about 10 to as many as hundreds of thousands of nucleotides. The conditions and protocols for such hybridization reactions are well known to those of skill in the art as are the effects of probe size, temperature, degree of mismatch, salt concentration and other parameters on the hybridization reaction. For example, the lower the temperature and higher the salt concentration at which the hybridization reaction is carried out, the greater the degree of mismatch that may be present in the hybrid molecules.

To be used as an hybridization probe, the nucleic acid is generally rendered detectable by labelling it, with a detectable moiety or label, such as $^{32}P$, $^{3}H$ and $^{14}C$, or by other means, including chemical labelling, such as by nick-translation in the presence of deoxyuridylate biotinylated at the 5'-position of the uracil moiety. The resulting probe includes the biotinylated uridylate in place of thymidylate residues and can be detected (via the biotin moieties) by any of a number of commercially available detection systems based on binding of streptavidin to the biotin. Such commercially available detection systems can be obtained, for example, from Enzo Biochemicals, Inc. (New York, N.Y.). Any other label known to those of skill in the art, including non-radioactive labels, may be used as long as it renders the probes sufficiently detectable, which is a function of the sensitivity of the assay, the time available (for culturing cells, extracting DNA, and hybridization assays), the quantity of DNA or RNA available as a source of the probe, the particular label and the means used to detect the label.

Once sequences with a sufficiently high degree of homology to the probe are identified, they can readily be isolated by standard techniques, which are described, for example, by Maniatis et al. ((1982) *Molecular Cloning: A Laboratory Manual*, Cold Spring Harbor Laboratory Press, Cold Spring Harbor, N.Y.).

As used herein, conditions under which DNA molecules form stable hybrids and are considered substantially homologous are such that the DNA molecules with at least about 60% complementarity form stable hybrids. Such DNA fragments are herein considered to be "substantially homologous". In particular DNA that encodes invertase is substantially homologous to another DNA fragment if the DNA forms stable hybrids such that the sequences of the fragments are at least about 60% complementary and if a protein encoded by the DNA is invertase, i.e., catalyzes the conversion of sucrose into the hexoses, glucose and fructose. Thus, any nucleic acid molecule that encodes invertase and hybridizes with nucleic acid that encodes all or sufficient portion of invertase to be used as a probe is contemplated for use in preparing DNA constructs and transgenic tomato plants as described herein As used herein, all assays and procedures, such as hybridization reactions and antibody-antigen reactions, unless otherwise specified, are conducted under conditions recognized by those of skill in the art as standard conditions.

Preparation of transgenic tomato plants that express altered levels of invertase and produce fruits that exhibit altered solids content compared to non-transgenic plants.

The transgenic plants contemplated for use herein are those in which a heterologous or foreign gene encoding invertase has been inserted into the genome or into an episomal element, whereby the plant is engineered to express a desired phenotype, such as altered soluble or insoluble solids content in the fruit, or to produce a protein, which can then be isolated upon harvesting the plant.

The preferred transgenic plants provided herein are transgenic tomato plants that express DNA encoding invertase under the control of either a constitutive or a developmentally regulated promoter region that is recognized by the tomato plant transcriptional machinery, including trans acting regulatory factors and RNA polymerase II.

In addition, the invertase that is expressed in transgenic tomato plants should be processed through the plant processing pathway that directs it to the vacuoles. Invertase that is not directed to the vacuoles accumulates in the cell wall via the default pathway and results in plants that do not produce fruit of the desired phenotype and possibly in plants that are unhealthy and exhibit symptoms, such as stunted growth and impaired root formation. Consequently, the DNA encoding the invertase must also encode the necessary regulatory signals, including a signal sequence and vacuolar targeting sequence to target the invertase to the vacuole. Such signals and targeting sequences may be part of the DNA encoding the invertase, if the invertase is a vacuolar invertase, or the DNA encoding the signals may be operatively linked to the DNA that encodes the invertase.

The transgenic plants that contain and express invertase that is targeted to the vacuoles can be propagated and grown to produce fruit that exhibits altered soluble solids content, compared to the soluble solids content of tomato fruit produced by unmodified tomato plants.

Transgenic tomato plantlets (*L. esculentum* cv. UC82) that contain DNA constructs encoding invertase in operative linkage with a promoter recognized by the plant RNA polymerase II have been regenerated in tissue culture. Such plantlets were produced by transformation of tomato with various DNA constructs prepared herein, including, constructs in which the HDC promoter, the *L. esculentum*, the *L. pimpinellifolium*, or the CaMV 35S promoter is fused to DNA encoding the *L. esculentum* tomato fruit vacuolar invertase.

Introduction of heterologous DNA into plants.

Numerous methods for producing or developing transgenic plants are available to those of skill in the art. The method used is primarily a function of the species of plant. These methods include, but are not limited to, the use of vectors, such as the modified Ti plasmid system of *Agrobacterium tumefaciens*, the Ri plasmid system of *Agrobacterium rhizogenes* and the RNA virus vector, satellite tobacco mosaic virus (STMV). Other methods include direct transfer of DNA by processes, such as PEG-induced DNA uptake, microinjection, electroporation, and microprojectile bombardment (see, e.g., in Uchimiya et al. (1989) *J. of Biotech.* 12:1–20 for a review of such procedures).

Plant species, including tobacco, rice, maize, rye, soybean, *Brassica napus*, cotton, lettuce, potato and tomato, have been used to produce transgenic plants. Tobacco and other species, such as petunias, often serve as experimental models in which the methods have been developed and the genes first introduced and expressed. Generally, the DNA encoding the gene of interest is cloned or synthesized and operatively linked to regulatory regions, such as a promoter recognized by the plant RNA polymerase II, and then introduced into and expressed in a model plant. Protocols are then modified or developed for introduction into and expression of the gene in other host plants.

Transformation of dicots

*Agrobacterium tumefaciens* is a ubiquitous soil bacterium, which infects a wide range of dicotyledonous plants, and produces crown gall tumors by introducing DNA into plant cells at wound sites. T-DNA, which causes crown galls, is integrated into the genome of the host plant. Foreign genes are inserted into T-DNA through Ti plasmids, which have been modified so that they do not cause disease, and are then co-transferred and integrated into the host genome. In order to effect integration, only the T-DNA borders and some flanking sequences are needed in cis.

Transformation of monocots

Since *A. tumefaciens* does not infect monocots, other methods have been developed for the introduction of heterologous DNA into monocots. Such methods include, but are not limited to, electroporation of rice, wheat and sorghum protoplasts and electroinjection through cell walls and membranes; and direct and chemical-induced introduction of DNA (see, e.g., Ou-Lee et al. (1986) *Botany* 83: 6815–6819; Fromm et al. (1985) *Proc. Natl. Acad. Sci. USA* 82: 2037–2042; Freeman et al. (1984) *Plant Cell Phys.*,25: 1353–1365; Lorz et al. (1985) *Mol. gen. Genet.* 199: 178–182; Krens et al. (1986) *Nature* 296: 72–74).

Methods for introducing heterologous DNA into plants and plant cells

DNA uptake can be accomplished by DNA alone or in the presence of polyethylene glycol (PEG), which is a fusion agent, with plant protoplasts or by any variations of such methods known to those of skill in the art (see, e.g., U.S. Pat. No. 4,684,611 to Schilperoot et al.). Electroporation, which involves high-voltage electrical pulses to a solution containing a mixture of protoplasts and foreign DNA to create reversible pores, has been used, for example, to successfully introduce foreign genes into rice and *Brassica napus*. Microinjection of DNA into plant cells, including cultured cells and cells in intact plant organs and embryoids in tissue culture and microprojectile bombardment (acceleration of small high density particles, which contain the DNA, to high velocity with a particle gun apparatus, which forces the particles to penetrate plant cell walls and membranes) have also been used.

The particular protocol and means for introduction of the DNA into the plant host must be adapted or refined to suit the particular plant species or cultivar.

Preparation of DNA constructs that encode invertase

The DNA constructs contain invertase-encoding sequences of nucleotides operably linked to genomic regulatory regions, including promoter regions. If the invertase encoded by the DNA is not directed to the vacuoles, DNA encoding appropriate regulatory and targeting signals, such as the invertase vacuolar sequences, can be operably linked to the invertase coding DNA.

The DNA constructs may contain sequences of nucleic acids which are native or homologous to the host plant into which it will be transferred and sequences which are foreign or heterologous to the host plant into which it will be transferred. These DNA constructs are alternatively referred to as recombinant DNA constructs, that is, fusions of various sequences produced using recombinant techniques well known in the art. The DNA constructs include regulatory regions including, promoters, transcription initiation sites, transcription termination sites, and, if necessary, vacuole sorting sequences including signal sequences and carboxyl-terminal propeptides may be included. Any or all of these component sequences may be homologous or heterolgous to the host plant cell. Additional heterologous sequences may also be included if need to facilitate transformation of the plant cell with the constructs.

Isolation of DNA encoding invertase

In plant cells enzyme activities are present in both the vacuole and cell walls of the cells. Cell wall enzymes differ from the vacuolar enzymes because they lack targeting signals that direct the enzymes to their subcellular compartments.

DNA encoding tomato fruit vacuolar invertase has been isolated herein using polyclonal antibodies that specifically bind to purified tomato fruit vacuolar invertase. These antibodies are specifically reactive with peptide sequences of tomato fruit invertase, but are substantially unreactive with other glycoproteins or glycan-containing groups. In addition, these antibodies can be employed in a variety of methods, including methods for determining the tomato fruit invertase content of a sample. Those of skill in the art can readily determine methodologies for using antibodies to measure the tomato fruit invertase content of a sample. See, for example, Clausen (1981) *Immunochemical Techniques for the Identification and Estimation of Macromolecules*, 2nd ed., Elsevier/North-Holland Biomedical Press, Amsterdam, the Netherlands.

The DNA encoding an invertase may be isolated by screening a cDNA library with such antibodies in order to detect translation products of cDNA clones that encode all or a part of a vacuolar invertase. Use of these antibodies to identify cDNAs may be accomplished using methods known to those of skill in the art (see e.g., Sambrook et al. (1989) *Molecular Cloning: A Laboratory Manual*, Vol. 2, Cold Spring Harbor Laboratory Press, Cold Spring Harbor, N.Y., pp. 12.1–12.44; Morton et al. (1987) *J. Biol. Chem.* 262: 11904–11907).

The antibodies have been used to screen a cDNA expression library and to identify DNA encoding tomato fruit vacuolar invertase. Expression libraries were prepared from poly(A)+ RNA isolated from the "pink" stage fruit of each tomato species. The libraries were screened with the antibodies made against purified tomato fruit vacuolar invertase.

DNA encoding an invertase may also be identified by any method known to those of skill in the art. For example, DNA encoding tomato vacuolar invertase proteins can be employed as probes for the identification and isolation of invertase-encoding sequences from a variety of appropriate cDNA or genomic libraries or other sample containing DNA and RNA from plant and animal species. Standard hybridization or other isolation techniques, as well known by those of skill in the art, can readily be employed for such purposes. Probes employed for such purpose typically have at least 14 nucleotides. Preferred probes employed for such purpose are those of at least about 50 nucleotides in length, and may include portions from the nucleotide sequence set forth in Sequence ID No. 2, or the various DNA molecules which encode the amino acid sequence set forth in Sequence ID No. 1; with nucleotide sequences of about 100 nucleotides or greater being especially preferred. Examples of such especially preferred sequences are those that have sequences set forth in Seq. ID No. 2, particularly those from the 5' coding region and the sequences encoding and surrounding what is believed to be the active site of invertase, as identified by nucleotide sequence comparisons with yeast invertase, *Bacillus subtilis* levanase and sucrase, and carrot tell wall invertase, (see Sturm and Chrispeels (1990) *The Plant Cell* 2:1107–1119 and references cited therein).

An exemplary 5' probe would be derived from the sequence of nucleotides 316–416 as set forth in Sequence ID No. 2; while an exemplary "active site" probe would be derived from the sequence of nucleotides 880–980 as set forth in Sequence ID No. 2. For ease of detection, such probes can be labeled with radioactive, chemiluminescent, or the like, labels.

Selected clones may then, if necessary, be used to obtain full-length clones. The clones may then be tested by any manner known to those of skill in the art in order to ascertain whether the invertase includes sequences sufficient to direct it to the vacuoles. If such sequences are absent, DNA encoding targeting sequences may be operatively linked to the clone.

Any clone that encodes or has been modified to encode a protein that has invertase activity as defined herein may be used for preparing. DNA constructs and for transferring into an appropriate host plant.

In preferred embodiments, DNA constructs that contain DNA encoding at least residues 1–635 of a tomato fruit invertase preprotein having the amino acid sequences set forth in Sequence ID No 1 are provided.

The optional presence of a third leucine after amino acid 215 (Pro) is also contemplated, in which case the subsequent sequences encoding Asp-Trp-Val . . . would correspond to amino acids 219, 220, 221, etc., and the resulting full length protein would be 636 amino acids long.

Those of skill in the art recognize that, by virtue of the degeneracy of the genetic code, numerous DNA molecules have nucleic acid sequences that encode the amino acid sequence set forth in Sequence ID No. 1 For example, a presently preferred nucleic acid sequence is set forth in Sequence ID No. 2, corresponding to the native nucleotide sequence encoding tomato fruit invertase from *L. esculentum*. Other sequences of nucleotides that encode this invertase or an invertase that functions equivalently may be obtained by methods known to those of skill in the art, including chemical synthesis and isolation of other invertase-encoding genes. Such invertases are limited to those that function in tomatoes and catalyze the hydrolysis of sucrose to fructose and glucose. If the invertase is not directed to the plant vacuole or is improperly processed in the tomato plant, DNA sequences encoding proper signal and vacuolar targeting sequences should be operatively linked to the invertase-encoding DNA.

Full-length cDNA and genomic clones that encode tomato fruit vacuolar invertase from both *L. esculentum* and *L. pimpinellifolium* have been isolated. The coding regions of both genes are identical with the exception of a three-nucleotide insertion in the *L. pimpinellifolium* gene.

Since invertase gene expression in *L. esculentum*, however, differs significantly from that in *L. pimpinellifolium*, the apparent differences in fruit solids content may result from differences in gene expression, due to cis-acting factors, including differences in nucleotide sequences of regulatory regions associated with the invertase genes, or regulatory factors acting in trans, such as factors which induce the earlier expression of the invertase gene in *L. pimpinellifolium*.

Genomic clones, including promoter regions of the invertase gene from *L. esculentum* and *L. pimpinellifolium* have been isolated. Analysis of total RNA isolated from various stages of fruit development revealed that, in *L. pimpinellifolium*, invertase mRNA appears in green fruit, and is present at high levels in pink and red fruit. In *L. esculentum* cv. Uc82, however, invertase mRNA does not appear until the pink stage of fruit development and is present at high levels only in red fruit.

The promoter region from *L. pimpinellifolium* can be fused to DNA encoding invertase and introduced into *L. esculentum* tomato plants in order produce *L. esculentum* plants in which invertase is expressed at an earlier stage in ripening than in the non-transgenic plants. Constructs in which the promoter region from *L. pimpinellifolium* is fused to the *L. esculentum* gene have been prepared as means for altering expression of the *L. esculentum* invertase gene and to thereby increase the soluble solids content of the fruit.

In addition, expression of the invertase gene in transgenic tomato plants may be accomplished, by operatively linking it to a developmentally regulated promoter. DNA encoding developmentally regulated promoter sequences obtained from the invertase structural gene and sequences that direct proper secretion and targeting of invertase have been identified and isolated, and DNA constructs containing DNA encoding invertase and fruit-specific genomic regulatory sequences are provided.

Selection of developmentally regulated promoters and other regulatory sequences

Identification and isolation of promoter regions.

To accomplish the modification of invertase gene expression in tomato plants by transformation of tomato tissue with invertase encoding sequences fused to developmentally responsive promoters, it is necessary to first clone and characterize promoter sequences capable of appropriately regulating the expression of invertase in fusion constructs. These promoter sequences must confer fruit specificity and an appropriate temporal control upon the expression of the coding sequences to which they are fused.

Preferred promoter regions and other regulatory sequences are those that are fruit specific and developmentally controlled. A preferred regulatory region is one which would promote expression of recombinant invertase at an earlier stage of tomato fruit development than occurs when the subject plant does not express recombinant invertase. Other embodiments include regulatory sequences that promote expression throughout fruit development.

Any developmentally regulated promoter region that, when linked to invertase and introduced into a tomato plant host, is not expressed until early in fruit ripening and is expressed at high levels early during fruit ripening, is preferred for use herein. Especially preferred regulatory sequences are those which promote expression at about the breaker stage of tomato fruit development, the stage at which the fruit begins to turn pink or red, with continued promotion of expression until the tomato fruit has reached the red stage.

More specifically, the regulatory regions have been isolated by screening a *L. pimpinellifolium* genomic DNA library with a probe containing cDNA encoding all or a portion of an invertase-encoding DNA sequence. A preferred subclone is one, which may be identified by restriction enzyme-mapping, that includes the 5' portion of an invertase-encoding sequence because there is a good chance that it will hybridize with the ATG start-site and upstream sequences of genomic clones.

For example, a 0.8-kb XhoI-HindIII 5'-end fragment of pTOM3-L1 was used as a cDNA probe and a plasmid containing an invertase-encoding fragment was isolated.

Selected positive clones may be plaque-purified and restriction enzyme-mapped. Restriction enzyme-mapped clones having inserts extending the furthest upstream of the translation start site are then selected for further characterization as the most likely to include the desired promoter sequences. For example, clones, λPI.6 and λPI.9, which are preferred clones described herein, include about 4 kb upstream of the translation start site.

Developmentally regulated promoter regions may also be isolated by any method known to those of skill in the art. For example, a method for isolating clones that encode a portion of a developmentally regulated gene is described in PCT Application WO 89/12230, which is based on U.S. Patent application Ser. No. 07/352,658 to Fitzmaurice et al., filed May 18, 1989, which is herein incorporated in its entirety by reference. The method provides a means to isolate promoter regions from genes that are, preferably, expressed in the tomato fruit prior to ripening, at the breaker stage. Briefly, plant tissues are collected from the particular plant species at different stages in development. Total RNA is extracted and poly $(A)^+$ mRNA isolated. The poly$(A)^+$ mRNA from each stage is translated and the products from each stage compared by any method, such as 2D gel electrophoresis, known to those of skill in the art. Translation products that correspond to mRNA that is abundant in some tissues, absent in others, abundant during certain stages of development and low or absent during others, and present during all stages, are identified. For example, a 38.5 kDa translation product of mRNA from tomato fruits increases in abundance as the fruit develops. Such a product can serve as a marker protein for proteins that are expressed during fruit ripening.

Total RNA is then prepared from early and late tissues, poly (A)⁺ RNA is prepared and each preparation is fractionated on sucrose gradients. RNA fractions are translated across the gradient to ascertain which are enriched in marker proteins, such as the 38.5 kDa marker, and the RNA enriched with the marker protein encoding mRNA is labeled. This RNA is used to probe a cDNA library prepared from poly (A)⁺ RNA isolated at an intermediate stage of development and clones that differentially hybridize to the different RNA preparations are selected. These clones can be further characterized by northern analysis to select those that hybridize to mRNAs abundant in the fractions selected for study. Those that hybridize to mRNA that exhibits the desired developmentally regulated expression are used as probes to screen genomic libraries in order to isolate the gene and regulatory sequences. The upstream portions can be sequenced and promoter regions identified and tested by fusing to reporter genes and looking for the appropriate regulation or pattern of expression in protoplasts.

In particular, one clone, that upon transcription in vitro results in an $\int$50 kDa translation product, exhibits such regulation. This clone has been used to screen a tomato genomic library and a clone has been isolated. The selected clone appears to have substantial homology with bacterial histidine decarboxylase and is herein referred to as the HDC gene. The portion of the clone upstream from the translation initiation site includes the promoter region, which appears to be developmentally regulated.

One such promoter region has-been selected, herein referred to as the HDC promoter region, is among those preferred for use herein (see Seq. ID No. 4 including nucleotides upstream from about 889). A portion of this promoter region which developmentally regulated, is operatively linked to DNA encoding invertase. Constructs including this promoter region in operative linkage with DNA encoding invertase have been prepared. The constructs, HDC/3-Li.1, HDC/3-L1.2 and HDC/3-L1.3, contain different portions of the upstream sequences and are used to prepare transgenic plants. Such transgenic plants should express developmentally regulated levels of invertase.

In other preferred embodiments, invertase regulatory sequences from *L. esculentum* and *L. pimpinellifolium* are provided. These have been obtained by constructing genomic libraries of each species and screening the with a probe made from an invertase-encoding clone, such as plasmid pTOM3-L1, selected from *L. esculentum* fruit cDNA library. The positive clones have been restriction enzyme-mapped and partially or completely sequenced. Thus characterized, these DNA fragments have then be used to make fusions with each other or with previously isolated invertase-encoding sequences. Thus *L. pimpinellifolium* promoter sequences can been fused to *L. esculentum* invertase-encoding regions.

Other developmentally regulated promoters may be identified and isolated by means known to those of skill in the art. Such promoters preferably confer fruit specificity and an appropriate temporal control upon the expression of the coding sequences to which they are fused. For example, U.S. Pat. No. 4,943,674 to Houck et al., describes methods and examples of suitable developmentally regulated promoter regions.

Preferred promoter regions are fruit-specific developmentally regulated promoter regions, including, but not limited to, the promoter regions from, *L. pimpinellifolium*, *L. esculentum*, the HDC promoter, the polygalacturonase promoter, and the 2ALL gene (see, U.S. Pat. No. 4,943,764 to Houck et al.). Most preferred promoter regions for use herein, include the HDC promoter region (SEQ ID No. 4) and the regulatory regions from the *L. pimpinefollium* genomic clone (SEQ ID NO. 5).

Regulatory sequences can also be used to control the expression of sense or anti-sense gene sequences in solanaceous plant species. This is accomplished by placing the gene sequence of interest under the control of appropriate regulatory sequences by inserting such sequences downstream of, and in open reading frame therewith. Since, by enhancing the expression of the sense gene, increased levels of the desired gene product are likely to be produced, expressing an anti-sense sequence derived from the gene of interest should result in reduced levels of the gene product in the cell. Anti-sense mRNA hybridizes with native mRNA, thereby preventing its translation into the product of interest. In this way, means to modulate the level of invertase gene product in a given host cell system are provided.

The regulatory regions, including the promoters, may be linked to other genes to achieve-regulated expression of such genes in plants. For example, constructs have been prepared in which different portions of the HDC promoter region and the Lycopersicon invertase promoter regions have been fused to the coding region of the *E. coli* β-glucuronidase (GUS) gene.

Identification and isolation of DNA encoding processing and targeting signals

The identification and isolation of regulatory elements associated with tomato fruit vacuolar invertase gene can be accomplished by use of a cDNA clone encoding invertase as a probe.

DNA encoding sequences of amino acids that direct targeting or sorting of the invertase protein, as well as other proteins, to the tomato fruit vacuoles, are provided. These include signal sequences, such as the invertase signal sequence, and carboxyl-terminal propeptide sequences. A 15 amino acid glycosylated carboxyl-terminal propeptide (CTPP) of the barley lectin proprotein is necessary for the efficient sorting of this protein to plant cell vacuoles (Bednarek et al. (1990) *The plant Cell* 2:1145–1155). In addition, it appears that the β-1,3-glucanase CTPPs of *Nicotiana tabacum* and *N. plumbaginifolia* may also be necessary for vacuolar sorting. Sequence comparison between the Nicotiana β-1,3-glucanase CTPPs and the carboxyl-terminal domain of the vacuolar tomato fruit invertase indicates 85% sequence similarity over a region of seven amino acids between residues 606 and 612 of tomato fruit invertase-encoding regions (see Sequence ID No. 1).

More specifically, DNA encoding what appear to be tomato fruit invertase signal sequences and other sequences that are removed during processing have also been provided. This region of the structural gene includes amino acids 1 through about 92 of the invertase-encoding sequence ID No. 1. This DNA, as well as DNA identified as the carboxyl-terminal sequences (residues 606–612 of Sequence ID No. 2) of the precursor protein described above, may also used to direct the targeting of homologous or heterologous peptides into vacuoles by host recombinant solanaceous plants. Expression of the desired homologous or heterologous peptides from DNA constructs that include the above-described signal sequences and carboxyl-terminal coding sequences upstream of, and downstream of, respectively, and in reading frame with, the peptide, should direct a substantial portion of the expressed protein into the vacuoles of the host plant. Thus, invertase encoding genes from sources other than tomato fruit, such as yeast, may be linked to DNA encoding the CTTP, including the signal sequence from tomato invertase, and thereby be directed to the vacuole. The DNA encoding invertase and constructs herein provided may also be introduced into a variety of hosts, such as, solanaceous plants, prokaryotic or eukaryotic hosts, and invertase encoded by such DNA may be expressed. Exemplary hosts include yeast, fungi, mammalian cells, insect cells, and bacterial cells. The use of such hosts for the recombinant production of heterologous genes is well known in the art. In preferred embodiments, the DNA constructs are introduced into tomato plants and expressed by transgenic tomato plants during fruit development.

The following examples are included for illustrative purposes only and are not intended to limit the scope of the invention.

EXAMPLE 1

Purification of invertase from *L. esculentum* fruit

All procedures employed in the purification of invertase were performed at 4° C. All centrifugations were at 27,500× g for 20 min, except as otherwise noted. The purification scheme was carried out as follows:

Nine kilograms of fresh, ripe *L. esculentum* fruit (fresh market tomatoes which are widely available for consumer purchase, e.g., at fruit and vegetable stands, grocery stores, etc.) were homogenized in an Osterizer blender for 30 seconds in 5 liters of 1M Tris-HCl, pH 7.6, containing 0.2% (v/v) β-mercaptoethanol, 2% (v/v) insoluble polyvinylpyrrolidone, 4 mM EDTA, 2 mM $MgCl_2$, 2 mM $MnCl_2$, and 4 mM EGTA. The homogenate was centrifuged at 9000× g for 20 minutes, and the supernatant was collected. Ammonium sulfate was added slowly (over a period of about 10 hours) to 80% of saturation, and the mixture was stirred for 0.5 hr. The precipitate was collected by centrifugation at 9000× g for 20 minutes and dissolved to a final volume of about 2 liters in 10 mM Tris phosphate, pH 6.7, containing 0.2% (v/v) β-mercaptoethanol. The solution was dialyzed (employing tubing have a MW cut-off of 12–14 kDa) against the same buffer, and then the dialysate was centrifuged at 20,000× g for 20 minutes. Final volume was 2850 ml.

Ammonium sulfate was then added to the supernatant to 10% of saturation and stirred for 1.5 hr. The precipitate was collected by centrifugation and discarded. Ammonium sulfate was added slowly (over a period of about 4 hours) to the supernatant to 80% of saturation and was stirred for about 1 hour. The precipitate was collected by centrifugation at 20,000× g for 20 min at 4° C., and was resuspended to a final volume of about 200 ml in 10 mM Tris phosphate, pH 6.7. This solution was dialyzed against the same buffer overnight at 4C.; the final volume of the dialyzed solution was 250 ml.

Following dialysis, the crude enzyme solution was loaded on a DEAE-cellulose column (Whatman DE52) which had been pre-equilibrated in 10 mM Tris phosphate, pH 6.7. The column was washed with 350 ml of 10 mM Tris phosphate, pH 6.7, and then eluted with 750 ml of a 0 to 0.5 M NaCl gradient in 10 mM Tris phosphate, pH 6.7. Five milliliter fractions were collected and assayed for invertase activity.

Invertase activity was assayed as follows. Fifty µl of sample was combined with 1.95 ml of a solution of 50 mM sucrose in 13.6 mM citric acid, 26.4 mM disodium phosphate, pH 4.8, at 30° C. After 10–20 min incubation at 30° C., the reaction was stopped by addition of 2 ml of alkaline copper reagent which was prepared the same day by mixing 25 parts of copper reagent A to 1 part of B. Copper reagent A was prepared by dissolving 25 g of anhydrous $Na_2O_3$, 25 g of Rochelle salt (sodium potassium tartrate), 20 g of $NaHCO_3$, and 200 g of anhydrous $Na_2SO_4$ in about 800 ml of water and diluting to one liter. The temperature of the solution was not allowed to fall below 20° C. Copper reagent B consisted of 15% $CuSO_4 \cdot 5H_2O$ containing 1 to 2 drops of concentrated $H_2SO_4$ per 100 ml.

Quantification of the reducing sugars liberated by invertase activity present in the sample was carried out by the procedure of Nelson [(1944) *J. Biol. Chem.* 153:375–380 (1944)] as follows: The samples were mixed thoroughly, and 400 µl were removed from each sample and heated for 20 minutes in a boiling water bath. After cooling, 200 µl of the arsenomolybdate reagent (preparation described below) were added. The samples were mixed thoroughly, diluted to 5 ml with $H_2O$, and held at room temperature for 20 minutes to permit the formation of a stable blue color. Samples were read at 660 nm.

The arsenomolybdate reagent was prepared as follows: 25 g of ammonium molybdate were dissolved in 450 ml distilled water, and 21 ml of concentrated $H_2SO_4$ were added with stirring. Three grams of $Na_2HAsO_4 \cdot 7H_2O$, dissolved in 25 ml of water, were added with mixing, and the solution was placed in an incubator at 37° C. for 24 hours. This reagent was stored in a glass-stoppered brown bottle.

Fractions containing invertase activity were pooled and concentrated by ultrafiltration (MW cut-off of 10 kDa) against 1M NaCl, 100 mM sodium acetate, pH 5.6. The final sample volume of 14 ml was applied to a Sephacryl S-200 column (2.5×75 cm) pre-equilibrated with the same buffer, which also was used as elution buffer. Five milliliter fractions were collected and assayed for invertase activity as described above. Fractions containing activity were pooled and concentrated by ultrafiltration as described above. The resulting sample was dialyzed against 20 mM Tris·HCl, pH 7.4, containing 0.15 M NaCl, 1 mM $MnCl_2$, 18 mM $MgCl_2$, 1 mM $CaCl_2$, and 0.1% Triton X-100, and was applied to a Concanavalin A-Sepharose column (6 ml bed volume; Pharmacia LKB Biotechnology, Piscataway, N.J.) pre-equilibrated with the same buffer. The column was washed with 60 ml of the above-described sample suspension buffer, followed by 30 ml of the same buffer containing 50 mM α-D-methyl-mannoside. Proteins were eluted with 30 ml of the sample suspension buffer containing 50 mM α-D-methyl-mannoside. The eluate was assayed for invertase activity as described above.

Fractions containing invertase activity were concentrated by ultrafiltration as described above and stored at 4° C.

EXAMPLE 2

CHARACTERIZATION OF INVERTASE PURIFIED FROM *L. ESCULENTUM* FRUIT

A. Specific activity

Table I provides specific activity values for invertase at each step in the purification process. The procedure of Example 1 resulted in an approximately 120-fold enrichment of invertase activity. The specific activity of the protein obtained in the final stage of purification was 1082 µmoles/min/mg protein.

TABLE I

Purification of Invertase from *L. esculentum* Fruit

| Purification | Protein (mg) | Activity (µmoles /min.) | Specific Activity (µmoles/ min/mg protein) | Yield % |
|---|---|---|---|---|
| Crude homogenate | 8012 | 71416 | 8.91 | 100 |
| Ammonium sulfate precipitation | 8175 | 61560 | 7.53 | 86.0 |
| DEAE-cellulose | 72.4 | 20272 | 280.0 | 28.4 |
| Sephacryl-200 | 20.9 | 17280 | 826.7 | 24.2 |
| Concanavalin-A Sepharose | 9.5 | 10280 | 1082 | 14.4 |

B. Gel Analysis

Samples of the material obtained after the first and second passage over the Sephacryl S-200 column and passage over the Concanavalin A-Sepharose column were evaluated by SDS-PAGE. The protein concentration of each sample was adjusted to 0.6 µg/lane, and each sample was heated at 95° C. in SDS loading buffer (62.5 mM Tris·HCl pH 6.8, 10% glycerol, 2% SDS, 5% β-mercaptoethanol, 0.1% bromphenol blue) for 4 min prior to loading on a 10% polyacrylamide gel containing 0.1% SDS. Following electrophoresis [Laemmli (1970) Nature 227:680–685], the proteins were detected by silver-staining [Morrissey (1981) Anal. Biochem. 117:307–310]. Molecular weight standards were purchased from Bio-Rad (low range markers).

Gel analysis revealed sequential enrichment, by the passages over Sephacryl S-200 and Concanavalin A-Sepharose columns, of a major protein having an apparent molecular weight of ~52 kDa, and two minor species of about 30 and 24 kDa.

C. Western Analysis

Polyclonal antisera reactive against carrot cell wall invertase were used to identify the ~52 kDa protein isolated from L. esculentum fruit as invertase. The antisera, described by Lauriere et al. [(1988) Biochimie 70:1483–1491], also reacted with the approximately 30 and 24 kDa proteins.

D. Substrate specificity

The substrate specificity of purified L. esculentum invertase was determined as follows. Ninety mg/ml of substrate (sucrose or raffinose), in 40 mM citric acid—NaHPO$_4$ buffer pH 4.8, were reacted at 30° C. for 30 minutes with 3.8 µg of protein obtained following Concanavlin A-Sepharose column chromatography. The products of these reactions were then analyzed by thin layer paper chromatography using isobutanol:pyridine:H$_2$O:acetic acid (12:6:4:1) as the solvent for ascending chromatography [Gordon et al. (1962) J. Chromatog. 8:44]. The positions of the carbohydrates were detected with alkaline silver nitrate [Chaplin (1986) "Monosaccharides", in Carbohydrate Analysis, A Practical Approach, Chaplin and Kennedy, eds; IRL Press, Washington, D.C., pp. 1–36]. The results showed that this protein hydrolyzed sucrose to glucose and fructose, and that it hydrolyzed raffinose to melibiose and fructose.

This characterization, in addition to the invertase activity assay results and the cross-reactivity to carrot invertase antibody, confirmed identification of the ~52 kDa protein as L. esculentum invertase.

E. Identification of ~52 kDa Protein as Vacuolar Invertase

To function in the desired manner, it is important that the invertase expressed in transgenic tomato be vacuolar invertase. It has been reported [Schaewen et al. (1990) EMBO J. 9:3033–2044); Dickinson et al. (1991) Plant Phys. 95: 420–425] that expression of yeast invertase in the cell wall or apoplastic space causes a slow-growth phenotype in tobacco, Arabidopsis, and tomato. This is an undesirable phenotype which results from improper targeting of invertase. Therefore, experiments were conducted to confirm that the ~52 kDa protein obtained in the practice of the present invention was vacuolar invertase.

Protoplasts are plant cells from which the cell wall has been removed; vacuoles are membrane-bound organelles within the cytoplasm of a plant cell. As neither protoplasts nor vacuoles have cell walls, neither source is likely to contain a significant amount of cell wall-associated invertase. Therefore, the presence of significant invertase activity in either of these sources would most probably be due to vacuolar invertase.

Protoplasts and vacuoles were purified from L. esculentum fruit tissue as follows.

Two ripened tomato fruit were squeezed into 35 ml of 25 mM Tris-MES [2-(N-morpholino)ethanesulfonic acid], pH 6.5, containing 0.7 M mannitol [Low pH Buffer; Boudet and Alibert, (1987) Methods in Enzymology, 148:74–81]. This suspension solution was filtered through two pieces of cheese cloth and stainless steel mesh (30 mesh). The filtrate was centrifuged at 100× g for 3 min to collect protoplasts. The protoplasts were then resuspended in the same buffer and collected by centrifugation at 100× g for 3 min.

Vacuolar fractionation was accomplished by a modification of the procedure described by Boudet and Alibert supra. This protoplast fraction was diluted 1:4 with 20% (w/v) Ficoll in Low pH Buffer, then overlaid with 5 ml of Low pH Buffer containing 6 mg/ml DEAE-dextran and 10% (v/v) Ficoll, 2 ml of 6 mg/ml dextran sulfate (potassium salt) and 5% (v/v) Ficoll in 25 mM Tris-MES, pH 8.0, containing 0.7 M mannitol (High pH Buffer), and 2 ml of 1.2 mg/ml dextran sulfate and 1% (v/v) Ficoll in High pH Buffer in a 15 ml glass centrifuge tube. This preparation was then centrifuged at 2000× g for 30 min. Vacuoles were recovered from the interface between the 5% and 1% Ficoll layers.

Protoplasts and vacuoles were lysed in the presence of invertase assay buffer (see Example 1), and analyzed for invertase activity as described in Example 1. The results of invertase assays of vacuolar and protoplast lysates revealed that the invertase activity in the vacuolar fraction was ~16-fold higher than the invertase activity in the protoplasts.

To determine if the vacuolar form of invertase was the form of invertase purified from L. esculentum fruit tissue, total proteins from the purified vacuoles were subjected to SDS-polyacrylamide gel electrophoresis and subsequent immunoblot analysis with the carrot cell wall invertase-specific antisera. The ~52 kDa, ~30 kDa, and ~24 kDa proteins detected in invertase purified from tomato fruit were also detected in vacuolar proteins.

F. Protein sequencing

A partially purified (after second gel filtration) tomato invertase preparation was separated on a 10% SDS-polyacrylamide gel and transferred to an Immobilon™ filter (Millipore Corporation, Bedford, Mass.) as described by Matsudaira [(1987) J. Biol. Chem. 262:10035–10038]. The filter was stained with Coomassie blue to identify the predominant ~52 kDa protein, which was excised from the Immobilon™ membrane and loaded directly into the protein sequencer.

An Applied Biosystems 470/120 Gas Phase Protein Sequencer was utilized to determine the N-terminal amino acid sequence of the sample by the method of Hunkapiller and Hood [(1983) Science 219:650–659].

The first 22 N-terminal residues of vacuolar invertase from L. esculentum were identified to be (SEQ ID NO 6): Tyr-Ala-Trp-Ser-Asn-Ala-Met-Leu-Ser-Trp-Gln-*-Thr-Ala-Tyr-*-Phe-Gln-Pro-Gln-Lys-Asn

*Amino acids at these positions could not be definitively determined.

The predominant ~52 kDa protein present in partially purified preparations of L. esculentum fruit vacuolar invertase, as well as the two minor additional proteins (~30 and ~24 kDa) detected in these preparations, were subjected to N-terminal protein sequence analysis. The ~52 kDa protein and the ~24 kDa protein contain identical residues at the N-terminus (22 residues); the ~30 kDa protein yielded a 22-amino acid sequence that was different from the sequence of N-terminal residues obtained from the ~52 and ~24 kDa proteins. Analysis of the amino acid sequence deduced from the full-length invertase cDNA clone pTOM3-L1 (Example 4) confirmed that the 22-residue sequence representing the N-terminus of the ~30 kDa protein is contained within the intact ~52 kDa protein.

In order to obtain additional sequence data from the partially purified L. esculentum fruit vacuolar invertase, which would be useful in identifying cDNA clones encoding this enzyme, the ~52 kDa protein was subjected to cyanogen bromide (CNBr) cleavage, and the resulting peptides were sequenced as follows. A partially purified preparation of L. esculentum fruit vacuolar invertase was separated by SDS- PAGE. The gel was stained with Coomassie blue to identify the predominant ~52 kDa protein, and the corresponding band was electroeluted and subjected to CNBr cleavage [Fogarty et al. (1974) *Br. J. Haematology* 26: 527–532]. The cleavage products were separated by SDS-PAGE (15% acrylamide gel) and transferred to an Immobilon filter. The filter was stained with Coomassie blue to identify six bands. Three of these six bands generated amino acid sequence data after being subjected to microsequence analysis. The sequences of these three fragments (CNBr-3, CNBr-4 and CNBr-6) are shown in Table II.

TABLE II

Partial Amino Acid Sequence of *L. esculentum* Fruit Vacuolar Invertase

Amino-terminal sequence of the ~52-kDa protein (SEQ ID NO 6):
Tyr—Ala—Trp—Ser—Asn—Ala—Met—Leu—Ser—Trp—Gln—*—Thr—Ala—Tyr—*—Phe—Gln—Pro—Gln—Lys—Asn Amino-terminal sequence of the ~30-kDa protein (SEQ ID NO 7):
Gly—Gln—Trp—Leu—Leu—Thr—Ile—*—Ser—Lys—Ile—Gly—Lys—Thr—Gly—Val—Ala—Leu—Val—Tyr—Glu—Thr Sequence of CNBr-3 (SEQ ID NO 8):
Met—*—*—*—Val—Asp—Phe—Tyr—Pro—Val—Ser—Thr—Lys Sequence of CNBR-4 (SEQ ID NO 9):
Met—Leu—Tyr—Thr—Gly—Asp—Thr—*—*—*—Val—Gln—Val—Gln—Asn—Leu—Ala Sequence of CNBR-6 (SEQ ID NO 10):
Met—Asn—Asp—Pro—Asn—Gly—Pro—Leu—Tyr

*Amino acid at this position could not be determined.

EXAMPLE 3

Production of polyclonal antisera to *L. esculentum* vacuolar invertase

Polyacrylamide gel-purified L. esculentum fruit invertase (approximately 52 kDa species obtained following separation on Concanavalin A-Sepharose) was excised from a gel, and 75 to 100 µg of protein were injected into rabbits, three times at intervals of two weeks, for the production of antibodies. The immunoglobulin fraction from immunized rabbits was subsequently purified from raw antiserum by Protein A-Sepharose affinity column chromatography. The antisera were centrifuged at 30,000× g for 20 min, and the lipid layer was discarded. The lower solution was loaded on a 6 ml Protein A-Sepharose column. The column was washed with 60 ml of 100 mM Tris·HCl (pH 8.0), followed by 60 ml of 10 mM Tris·HCl, pH 8.0. IgG was eluted with 100 mM glycine HCl (pH 3). Then, 0.8 ml of 1M Tris·HCl (pH 8.0) was added to 8 ml of antiserum. This purified immunoglobulin fraction was demonstrated by immunoblot analysis to react with many tomato fruit proteins present in the early purification fraction obtained after the first ammonium sulfate precipitation of the crude homogenate. This purified immunoglobulin fraction was also found to react with horseradish peroxidase, a heavily glycosylated plant protein. The nonspecific immunoreactivity of the antiserum probably resulted from the presence of antibodies directed against the glycan groups of tomato fruit invertase, which is heavily glycosylated.

To remove antibodies reactive with glycans, the immunoblobulin fraction of this antiserum was passed over a horseradish peroxidase-Sepharose column which was prepared by coupling horseradish peroxidase to CNBr-activated Sepharose 4B (Pharmacia LKB Biotechnology, Piscataway, N.J.). The antibodies reactive with tomato fruit invertase peptides did not bind to the column, whereas antibodies reacting with glycan groups were retained. The resulting "cleared" antibody fraction reacted specifically with tomato fruit invertase.

EXAMPLE 4

Isolation of a cDNA encoding *L. esculentum* vacuolar invertase

A. Library Construction

Poly(A)$^+$ RNA was isolated from fresh *L. esculentum* cv. UC82 (grown by SIBIA from seeds obtained from Dr. Charles Rick, University of California at Davis, Dept. of Vegetable Crops) 3-inch intermediate fruit (i.e., fruit at the "turning" to "pink" stage of development) with the mRNA purification kit from Pharmacia LKB Biotechnology (Piscataway, N.J.). The RNA was used to construct size-selected cDNA libraries (of ~0.6-2 kb and ~2 up to 4 kb and greater) in λgt11, using a modification of the protocol of Gubler and Hoffman [(1983) *Gene* 25:263–269] detailed below:

1. First strand synthesis a. A NotI-oligo(dT) primer-adapter (Promega Corporation, Madison, Wis.) was annealed to the tomato fruit poly(A)$^+$ RNA, by combining:

```
     5 µl poly(A)+ RNA (5 µg)
   1.5 µl primer-adapter (1.5 µg)
   1.5 µl dH2O (DEPC-treated)

8 µl (total volume)
``` b. The above combination was incubated for 5 minutes at 70° C., then cooled to room temperature, and finally the following components were added, and the resulting mixture was chilled on ice:

```
   5.5 µl dH2O (DEPC-treated)
    10 µl 5X reverse transcriptase (RT) buffer
     1 µl 0.5M DTT
     2 µl RNasin^R (24 U/µl; Promega Corporation, Madison, WI)
    10 µl 5X dNTPs 36.5 µl [total volume of (a) plus (b)]
``` c. The above combination was incubated for 5 minutes on ice, then the following components were added:

```
     6 µl actinomycin-D (400 µg/ml)
   2.5 µl α-32P-dCTP (3200 Ci/mmol)
     5 µl MMLV-RT (200 U/µl, BRL)

50 µl [total volume of (a) plus (b) plus (c)]
``` d. One µl of the above was immediately added to 1 µl of 50 mM EDTA in a microfuge tube and frozen at −20° C. as a t=0 aliquot; the remainder of the mixture was incubated for 60 min at 37° C., then the following components were added thereto:

```
     1 µl RNasin^R (24 U/µl, Promega Corporation, Madison, WI)
     3 µl MMLV-RT (200 U/µl)

53 µl [total volume of (a) plus (b) plus (c) plus (d)]
``` e. The above combination was incubated for 30 minutes at 37° C.; then the reaction was stopped with 2 µl of 0.5M EDTA, and 1 µl and 0.5 µl t=90 aliquots were taken for analysis.

f. The remainder of the reaction mixture was extracted with an equal volume of a 1:1 mixture of phenol and chloroform, then with an equal volume of chloroform alone.

g. The nucleic acids were precipitated with 0.2 volume of 10M ammonium acetate, plus 2 volumes of ethanol at −20° C. overnight.

h. Analysis: The 0.5 µl t=90 aliquot was saved to run on a gel alongside the 2nd strand reaction aliquot.

The 1 µl t=0 and t=90 aliquots were TCA-precipitated to determine % incorporation of label, as follows:

Fifteen µl of carrier DNA (5–10 mg/ml) and TE were added to each of the time aliquots, to provide a total solution for each of 100 µl. Ten µl of each solution were spotted on glass filters and set aside. Four hundred µl of 20% TCA were added to the remaining 90 µl. The resulting mixtures were incubated 10 min on ice, then transferred to glass filters with vacuum filtration apparatus, and washed with ~5 ml of 5% TCA. The filters were counted on a scintillation counter and the % incorporation was calculated as follows:

$$\% \text{ incorporation} = \left[ \frac{100 \times cpm \text{ on the } 90 \text{ µl } TCA \text{ precipitate filter}}{9 \times cpm \text{ on the } 10 \text{ µl aliquot filter}} \right]$$

net % incorporation =

[% incorporation at $t = 90$] − [% incorporation at $t = 0$]

µg ss cDNA = net % incorporation/1.4

2. Second strand synthesis a. The first strand cDNA precipitate was collected by centrifugation in a microfuge for 15 minutes at 4° C. The resulting pellet was washed in 80% ethanol (prepared with DEPC-treated water), dried in a Speed-Vac, resuspended in 68.85 µl of DEPC-treated, deionized water. To this solution were added the following components:

| |
|---|
| 20 µl 2nd strand buffer |
| 1.5 µl 10 mM β-NAD |
| 5 µl 4 mM dNTPs |
| 2.5 µl DNA polymerase I (10 U/µl) |
| 1 µl E. coli DNA ligase (4 U/µl) |
| 1.15 µl RNase H (2 U/µl) |
| 100 µl (total volume) |

This mixture was incubated for 60 minutes at 12° C.

b. Then the following components were added to the above mixture:

| |
|---|
| 1.5 µl DNA polymerase I (10 U/µl) |
| 0.75 µl E. coli DNA ligase (4 U/µl) |
| 102.25 µl [total volume of (a) plus (b)] |

This mixture was incubated for 60 minutes at 22° C., then the reaction was stopped by adding 4 µl of 0.5M EDTA. A 0.5 µl aliquot was taken to check by gel electrophoresis. The remainder of the mixture was extracted with an equal volume of a 1:1 mixture of phenol and chloroform, then with an equal volume of chloroform alone. The DNA was then precipitated with 0.2 volume of 10M ammonium acetate, plus 2 volumes of ethanol at −20° C. overnight.

c. The 0.5 µl aliquots of the first and second strand reactions were electrophoresed on an alkaline 1.4% agarose mini-gel with a size marker lane see [Maniatis et al., (1982) *Molecular Cloning: A Laboratory Manual*, Cold Spring Harbor Laboratory Press, Cold Spring Harbor, N.Y., pp. 171–172]. The marker lane was cut off, stained for 30 min in 1X neutralizing solution with 0.5 µg/ml ethidium bromide (EtBr), destained for 15 min in $H_2O$, and photographed. The remainder of the gel was incubated in two changes of 7% TCA for 30 minutes each, rinsed with $H_2O$, blotted dry, and exposed to autoradiographic film overnight at −70° C. with one intensification screen.

3. Blunt-ending a. The second strand precipitate was collected by centrifugation in a microfuge for 15 minutes at 4° C., washed with 80% ethanol, then dried in a Speed-Vac. The cpm present in the pellet was determined. Assuming the second strand reaction was 100% efficient and the cDNA mass is twice the mass of single-stranded cDNA calculated for the first strand reaction, the ratio of (µg cDNA)/cpm was calculated. This provided a conversion factor for use throughout the remaining steps (for the calculation of mass from cpm).

b. The pellet was resuspended in:

| |
|---|
| 5 µl 10X T4 polymerase buffer |
| 36.25 µl $dH_2O$ |
| 1.25 µl 4 mM dNTPs |
| 2.5 µl 10 mM DTT |
| 5 µl T4 DNA polymerase (1 U/µl) |
| 50 µl (total volume) |

This mixture was incubated for 20 minutes at 37° C., then the reaction was stopped with 2 µl 0.5M EDTA. The reaction mixture was extracted with one volume of a 1:1 mixture of phenol and chloroform, then with one volume of chloroform alone. The DNA was precipitated with 0.2 volumes of 10M ammonium acetate plus 2 volumes of ethanol at −20° C. overnight.

4. Preparation and addition of EcoRI adapters a. The 18-mer oligonucleotide (SEQ. ID NO 11) (GCTCGAGTGTACGTACCG) was phosphorylated by combining the following:

| |
|---|
| 3.0 µl 18-mer (450 pmol) |
| 3.8 µl $dH_2O$ |
| 1.2 µl 10X kinase buffer |
| 1.0 µl $\gamma$-$^{32}$P-ATP (7000 Ci/mmol) diluted 1:5 in $dH_2O$ |
| 1.0 µl T4 polynucleotide kinase (2 U/µl) |
| 10 µl (total volume) |

This mixture was incubated for 15 minutes at 37° C., then the following were added:

| |
|---|
| 1 µl 10 mM ATP |
| 1 µl T4 polynucleotide kinase (2 U/µl) |
| 12 µl (total volume of the final mixture) |

The resulting mixture was incubated for 30 minutes at 37° C., then boiled for 10 minutes to inactivate the enzyme.

b. The 22-mer oligonucleotide (SEQ. ID NO 12) (AATTCGGTACGTACACTCGAGC) was annealed to the phosphorylated 18-mer by adding 3 µl (450 pmol) of the 22-mer to the above mixture, bringing the final volume to 15 µl.

The resulting mixture was incubated for 5 minutes at 65° C., then cooled slowly to room temperature. The resulting EcoRI adapters were then ready to ligate at a concentration of 30 picomoles/µl.

c. The previously blunt-ended cDNA was collected by centrifugation in a microfuge for 15 minutes at 4° C., washed in 80% ethanol, and dried in a Speed-Vac. Approximate mass of the cDNA was estimated from the cpm of the resulting pellet, using the conversion factor from step 3(a).

d. The cDNA pellet was resuspended in: 7 µl EcoRI adapters (120 pmol; to yield a 50-fold molar excess of adapters)

```
    7 µl dH₂O
    4 µl 5X ligase buffer (BRL)
    2 µl T4 DNA ligase (2 U/µl)

20 µl (total volume)
```

5. Phosphorylation and digestion with NotI a. The ligation mixture was heated for 15 minutes at 72° C. to inactivate the ligase, then the following were added:

```
    22 µl dH₂O
    3 µl 10X NotI buffer (BRL ReAct 7, GIBCO BRL, Gaithersburg, MD)
    1 µl 10 mM ATP
    2 µl NotI (15 U/µl)
    2 µl T4 polynucleotide kinase (2 U/µl)

50 µl (total volume)
```

This mixture was incubated for 60 minutes at 37° C., then the reaction was stopped with 2 µl of 0.5M EDTA. The mixture was then extracted with an equal volume of a 1:1 mixture of phenol and chloroform, and finally with an equal volume of chloroform alone.

6. Purification and size-selection a. The NotI-digested DNAs were size-fractionated on a Sepharose CL-4B column equilibrated in TE. Approximately 1500 cpm of the selected cDNA fractions were electrophoresed on a 1% agarose gel with size markers, photographed, dried, and exposed to film overnight at −70° C. with 1 intensification screen.

b. The selected fractions (4–8) were electrophoresed on a 1% agarose gel in TAE, and the bands of the size ranges of interest, i.e., ~0.6–2 kb and 1.2 up to 4 kb or greater, were then cut out, and the cDNA was then electroeluted out of each slice of agarose. The cDNAs were precipitated with 0.2 volume of 10M ammonium acetate plus 2 volumes of ethanol at −20° C. overnight.

7. Ligation of cDNA to λgt11 vector

The cDNAs were collected by centrifugation in a microfuge for 15 minutes at 4° C., washed with ethanol, and dried. The pellet was counted in a scintillation counter and the cDNA mass was calculated, based on the cpm obtained. The pellet was resuspended in 23.2 µl of dilute TE to a concentration of ~6 ng/µl. Then the following were mixed:

```
    1.0 µl λgt11-Sfi/Not arms (0.5 µg; 0.035 picomoles;
          Promega Corporation, Madison, WI; catalog #T3230)
    6.5 µl cDNA insert (2–4 molar excess)
    1   µl 10 mM ATP
    1   µl 10X ligase buffer (Stratagene, La Jolla, CA)
    0.5 µl T4 DNA ligase (4 U/µl; Stratagene, La Jolla, CA)

10 µl (total volume)
```

The resulting mixture was incubated for 72 hours at 14°–16° C.

8. Packaging, titering, and amplification a. The cDNA-containing λgt11 vectors were packaged with the Gigapack Gold kit (Stratagene, La Jolla, Calif.), according to the directions provided.

b. The packaging reaction was titered on E. coli strain Y1088.

c. The percent recombinants was checked by blue-white color selection, plating on E. coli strain Y1090, and using plates containing X-gal plus IPTG. There were 100% recombinants in the present case; 3.5×10⁶ total recombinants.

9. The resulting λgt11 library was amplified as per the protocol described in the Stratagene Gigapack Gold packaging kit information packet.

10. The above-described protocol yielded ~150 ml of an amplified library at $7.7\times10^{10}$ p.f.u./ml.

| Reagent Solutions: | |
|---|---|
| 5X RT Buffer = | 5X dNTPs = |
| 250 mM TrisHCl, pH 7.4 | 5 mM dATP |
| 375 mM KCl | 3 mM dCTP |
| 15 mM MgCl₂ | 5 mM dGTP |
| 5X 2nd Strand Buffer = | 5 mM dTTP |
| 100 mM TrisHCl, pH 7.5 | 5X T4 Ligase Buffer (BRL) = |
| 500 mM KCl | 250 mM TrisHCl, pH 7.5 |
| 25 mM MgCl₂ | 50 mM MgCl₂ |
| 250 µg/ml BSA | 25% (w/v) PEG (MW 8000) |
| 50 mM (NH₄)₂SO₄ | 5 mM ATP |
| TE = | 5 mM DTT |
| 10 mM TrisHCl, pH 8.0 | Dilute TE = |
| 1 mM EDTA | 10 mM TrisHCl, pH 8.0 |
| 1X Neutralizing | 0.1 mM EDTA |
| Solution = | 6X Loading Buffer = |
| 1.5M NaCl | 30% glycerol |
| 1.0M TrisHCl, pH 8.0 | 0.025% bromphenol blue |
| 10X Ligase Buffer (Stratagene, La Jolla, CA) = | 0.025% xylene cyanol |
| 500 mM TrisHCl, pH 7.5 | |
| 70 mM MgCl₂ | |
| 10 mM DTT | |

Abbreviations:
DEPC = diethylpyrocarbonate
dNTP = deoxyribonucleotide triphosphate
DTT = dithiothreitol
IPTG = isopropyl-β-D-thiogalactopyranoside
MMLV-RT = Moloney-Murine Leukemia Virus Reverse Transcriptase
TE = 10 mM Tris-HCl, 1 mM EDTA
Dilute TE = 10 mM Tris-HCl, 0.1 mM EDTA
TAE = 0.04M Tris-acetate, 1 mM EDTA
X-gal = 5-bromo-4-chloro-3-indolyl-β-D-galactopyranoside B. Library Screening To identify clones expressing tomato invertase, the immunological screening protocol described in Sambrook et al. [(1989) Molecular Cloning: A Laboratory Manual, Vol. 2, Cold Spring Harbor Laboratory Press, Cold Spring Harbor, N.Y., pp. 12.16–12.20], was used to screen directionally cloned L. esculentum fruit cDNA expression libraries.

The primary antibody was antisera raised against tomato invertase protein and cleared of anti-glycan antibodies (see Example 3), and was pretreated as follows: 250 µl each of E. coli strain Y1090 extract and crude λgt11-E. coli strain Y1090 lysate were added to 5 ml of a 1:10 dilution of the tomato invertase antisera in blocking buffer (3% BSA in TNT; TNT is 10 mM Tris-HCl, pH 8.0, 150 mM NaCl, 0.05% Tween-20), and the mixture was incubated 4 h at room temperature. The mixture was further diluted 1:100 in blocking buffer before use.

The secondary antibody was an anti-rabbit IgG-alkaline phosphatase (AP) conjugate (Promega Corporation, Madison, Wis.), diluted 1:7500 in TNT. Antigen-antibody-antibody-AP complexes were located using the substrate 5-bromo-4-chloro-3-indolyl phosphate (BCIP) in combination with nitro blue tetrazolium, which detects the precipitated indoxyl group as described in Sambrook et al. [(1989) Molecular Cloning: A Laboratory Manual, Vol. 2, Cold Spring Harbor Laboratory Press, Cold Spring Harbor, N.Y., p. 12.20].

Approximately 250 immunopositive plaques were detected in the primary screen of approximately 300,000 plaques. Six positive plaques were selected for secondary screening. Following plaque purification of these immunopositives, one well-isolated plaque for each clone was picked and stored in 100 µl SM buffer [Maniatis et al. (1982) Molecular Cloning: A Laboratory Manual, Cold Spring Harbor Laboratory Press, Cold Spring Harbor, N.Y., p. 70]. Insert sizes were determined by first amplifying insert DNAs via a polymerase chain reaction (PCR) and then subjecting the amplified products to gel electrophoresis. Each PCR was conducted essentially according to the protocol provided by the Taq DNA Polymerase manufacturer (Perkin-Elmer Cetus, Norwalk, Conn.). For each reaction, 10 µl of phage eluate (containing $1. \times 10^5$ to $1 \times 10^6$ p.f.u.) was combined with λgt11 forward and reverse sequencing primers (New England Biolabs, Beverly, Mass., catalog #1218 and #1222), 10X Taq DNA polymerase buffer, and dNTPs, and the DNA amplification reactions were conducted. In addition to providing sufficient quantities of insert DNA for a size determination, the PCR products verified that each of the plaques contained a single clone. Clones λXTOM4, λTOM5 and λTOM8 each contained inserts of about 1.1 kb. Clone λTOM7 contained an approximately 1.4 kb insert, and clones λTOM3 and λTOM6 each contained an approximately 1.5 kb insert.

The λTOM3, λTOM4 and λTOM7 inserts were excised with SfiI and NotI, purified with Geneclean II (Bio101 Inc., La Jolla, Calif.), and ligated into pGEM-11Zf(−) (Promega Corporation, Madison, Wis.), which had been digested with SfiI and NotI. The ligation protocol was modified from the BRL protocol (GIBCO BRL, Gaithersburg, Md.). In brief, ~100 ng DNA in a 3:1 insert:vector molar ratio was incubated in 25 µl BRL ligase buffer containing 1 unit BRL T4 DNA ligase for ~20 hours at 14° C.

Fifty µl of each of the ligation mixtures diluted ⅕ with dH$_2$O was used to transform *E. coli* strain DH5α. For each transformation, 100 µl *E. coli* DH5α Subcloning Efficiency competent cells (obtained from GIBCO BRL, Gaithersburg, Md.) were mixed with 50 µl of ligation mixture and held for 30 minutes on ice, heat shocked at 42° C. for 45 seconds, and held on ice for two minutes. One ml of LB broth was added, and the mixtures were incubated for 1 hour at 37° C. with shaking at 225 rpm. The mixtures were spread on LB agar plates containing 100 µg/ml ampicillin. The plates had been pre-spread with 70 µl 2% X-gal in N$_1$N$_1$-dimethylformamide plus 30 µl 100 mM IPTG. After approximately 20 hours at 37° C., white colonies were picked, grown in liquid culture, and plasmid mini-preps were done according to the protocol of Sambrook, et al. [1989) *Molecular Cloning: A Laboratory Manual*, Vol. 1, Cold Spring Harbor Laboratory Press, Cold Spring Harbor, N.Y., p.1.40].

The insert DNAs from the resultant subclones pTOM3, pTOM4 and pTOM7 were sequenced according to the USB Sequenase$^R$ (United States Biochemical Corporation, Cleveland, Ohio) protocol. All insert DNAs were found to be identical at the 3' end but of varying lengths. The complete sequence of the longest of these three clones, pTOM3, contains 1339 bp which correspond to bases 837–2160 (shown in Sequence ID No. 2), plus a poly(A) tail comprising 15 adenine residues.

Comparison of the deduced amino acid sequence of the insert in pTOM3 and the amino acid sequence obtained from sequence analysis of a peptide generated by CNBr cleavage of the gel-purified preparation of *L. esculentum* vacuolar invertase revealed that a portion of the deduced amino acid sequence in Sequence ID No. 2 is present in a CNBr-generated fragment of tomato vacuolar invertase protein, CNBr-3. CNBr-3 also contains a consensus sequence for the active site of invertase protein sequenced to date [Sturm and Chrispeels (1990) *The Plant Cell* 2:1107–1119]. The N-terminal protein sequence determined by sequencing the predominant ~52 kDa protein of partially purified preparations of *L. esculentum* fruit vacuolar invertase was not located in the pTOM3-deduced amino acid sequence, implying that this cDNA clone does not encode a full-length invertase mRNA. This conclusion is supported by comparison of the pTOM3 encoded peptide sequence with that of carrot extracellular invertase [Sturm and Chrispeels (1990) *The Plant Cell* 2:1107–1119].

A 462 bp HindIII fragment of pTOM3, containing the 5' half of the DNA insert, was used as a probe to re-screen both the large insert (approximately 2 up to >4 kb) and small insert (~0.6–2.0 kb) λgt11 *L. esculentum* cv. UC82 fruit cDNA expression libraries for full-length invertase cDNA clones. Hybridization was overnight at 42° C. in 50% formamide, 5X SSPE, 5X Denhardt's solution, 0.1% SDS, 200 µg/ml denatured salmon sperm DNA. Eleven hybridizing clones were plaque purified. The insert sizes of these clones, as determined by PCR amplification and electrophoretic visualization of insert DNA, ranged from ~1.4 to ~2.2 kb. Inserts from five of these clones were subcloned and sequenced as described above. Four of the five clones sequenced showed 3' ends identical to that of pTOM3. The longest clone, pTOM3-L1, is 2196 bp in length (see Sequence ID No. 2), encodes full-length tomato invertase, and also contains the following 21 bp insert relative to pTOM3 preceding the poly (A) tail: nucleotides 2161–2181 of SEQ ID NO.2.

The amino acid sequence deduced from pTOM3-L1 was compared to the amino acid sequences of peptides generated by CNBr cleavage of vacuolar invertase purified from *L. esculentum* fruit and the amino-terminal sequence of purified invertase. Four regions of amino acid sequence deduced from this clone are identical to the amino acid sequences of various CNBr cleavage products of *L. esculentum* invertase, and one region of the deduced amino acid sequence is identical to the amino terminus of the purified invertase protein.

The ~30 kDa and ~24 kDa proteins which reacted strongly with anti-carrot invertase antisera in immunoblots of purified *L. esculentum* vacuolar invertase were suggested to be degradation products of the mature invertase protein. The first 22 amino acids of the ~24 kDa protein were determined by sequence analysis to be identical to the first 22 amino acids of the ~52 kDa protein. The first 22 amino acids of the ~30 kDa protein were determined by sequence analysis and did not correspond to the amino terminus of *L. esculentum* fruit vacuolar invertase. The portion of the amino acid sequence deduced from the nucleic acid sequence of pTOM3-L1 beginning at amino acid position +159 relative to the start of the mature protein and extending through position +180 is identical to the sequence of the first 22 amino acids of the ~30 kDa putative degradation product of tomato invertase, thus confirming that this peptide sequence was derived from tomato invertase.

The ATG translation start signal of pTOM3-L1 is the only in-frame ATG that results in an open reading frame from which can be deduced a single peptide including all of the amino acid sequences derived from purified *L. esculentum* fruit vacuolar invertase. Amino terminal sequence analysis of purified *L. esculentum* fruit vacuolar invertase indicates that the mature protein begins at the tyrosine residue at position 93 relative to the methionine encoded by the translation start codon (SEQ ID No. 1). Therefore, it appears that the first 92 amino acids of the protein encoded by pTOM3-L1 are post-translationally cleaved, leaving a 543 amino acid sequence extending from the amino terminus of the mature protein to the residue encoded by the codon preceding the stop codon.

Computer-assisted analysis of the resulting 543 amino acid peptide indicates that it has a molecular weight of ~60 kDa. The molecular weight of the mature deglycosylated tomato fruit vacuolar invertase was estimated to be ~45 kDa by SDS-PAGE. It is possible that additional post-translational modifications of the 635 amino acid precursor protein occur at the carboxy terminus.

Based upon the assumption that the molecular weight of the mature protein is ~45 kDa, the carboxy terminus of the mature protein has been predicted to be at amino acid position 501. This prediction is based upon the apparent molecular weight of the mature protein estimated by SDS-PAGE and thus is subject to experimental error of ±10 amino acids.

EXAMPLE 5

Isolation of a cDNA encoding L. pimpinellifolium vacuolar invertase

An L. pimpinellifolium pink fruit cDNA expression library was prepared from tomatoes (grown by SIBIA from seeds obtained from Dr. Charles Rick, University of California at Davis, Dept. of Vegetable Crops) and was screened, using L. esculentum cDNA clone pTOM3 as a probe, essentially as described in Example 4. Five clones were identified, plaque purified, subcloned, and sequenced, as described for the isolation and characterization of clones from the L. esculentum cDNA library. The longest clone (pLP-19) contains a 2166 bp insert which is 30 bp shorter than the pTOM3-L1 insert.

As observed for L. esculentum clones, two classes of L. pimpinellifolium cDHA clones containing two different 3' ends were identified. One class contained 21 additional nucleotides preceding the poly (A) tail that were absent in the other class. The sequences of the 21-nucleotide 3' inserts in the L. esculentum and L. pimpinellifolium clones are identical. Sequence comparisons of these five clones and the L. esculentum clones have shown that the nucleotide sequences are identical with the exception that the L. pimpinellifolium clones contain a three-nucleotide insertion (TCT) between nucleotide positions 650 and 651 of the L. esculentum cDNA (see SEQ ID NO 2). This results in the insertion of an extra amino acid (leucine) between amino acids 216 and 217 of the full-length product which correspond to amino acids 124 and 125 of the mature protein).

To isolate a full-length cDNA clone that encodes L. pimpinellifolium invertase, the L. pimpinellifolium fruit cDNA expression library was re-screened using a $^{32}$P-labeled synthetic oligonucleotide complementary to nucleotides 7–33 of the L. esculentum cDNA (see, SEQ ID NO 2). Hybridization was carried out overnight at 42° C. in 50% formamide, 5X SSPE, 5X Denhardt's solution, 0.1% SDS, 200 µg/ml denatured salmon sperm DNA and $10^6$ cpm/ml radiolabeled probe. One of the hybridizing clones that was purified and characterized is 2203 nucleotides in length, which is 7 nucleotides longer than the full length L. esculentum invertase cDNA pTOM3-L1. A comparison of the nucleotide sequence of this clone with the pTOM3-L1 sequence revealed that this L. pimpinellifolium clone is a full-length invertase-encoding cDNA that contains 7 nucleotides at the 5' end that are not present at the 5' end of pTOM3-L1; the authenticity of these nucleotides was confirmed by their presence in the 5' untranslated region of L. pimpinellifolium genomic clones (see Example 6).

EXAMPLE 6

Isolation of L. pimpinellifolium vacuolar invertase gene promoter sequences

A. Construction of a genomic library

A genomic library was constructed in λ FIX™ II (Stratagene, La Jolla, Calif.) using DNA isolated from seedling tissue of L. pimpinellifolium cv. Trujillo, LaLibertad Per (grown by SIBIA from seeds obtained from Dr. Charles Rick, University of California at Davis, Dept. of Vegetable Crops). The λ FIX™ II vector accommodates inserts of 9–23 kb in size, and includes phage T3 and T7 promoters, which flank the insert. The promoter and insert-containing fragment can be excised by digestion with NotI.

High molecular weight genomic DNA was prepared from leaves and stems of seedlings of L. pimpinellifolium by the CTAB procedure of Rogers and Bendich [(1988) Plant Molecular Biology Manual, pp. A6/1–10, Kluwer Academic Publishers, S. B. Gelvin, R. A. Schilperoot, eds.]. The genomic DNA was digested with Sau3AI such that the majority of the fragments were between 9 and 23 kb in size. The Sau3AI ends were partially filled in using dATP and dGTP. The λFIXII vector was digested with XhoI, and the overhang was partially filled in with dTTP and dCTP. This treatment resulted in the production of genomic DNA fragments which could ligate only with the vector overhang and eliminated the possibility of multiple DNA inserts in a single clone.

0.43 µg of genomic DNA fragments were ligated with 1 µg of vector. The ligation reaction was packaged using Stratagene Gigapack™ II Gold packaging extracts (Stratagene, La Jolla, Calif.), and the vector was titered on E. coli strain LE392. The titer was approximately $2 \times 10^6$ cfu/ml.

B. Library screening

Plasmid pTOM3-L1 (see Example 4.B), a clone encoding invertase from the L. esculentum fruit cDNA library, was digested with XhoI and HindIII, and the 800 bp insert was excised from a 1% agarose gel and purified. The insert was labeled with 32p and used to probe the L. pimpinellifolium genomic library under the following conditions:

Hybridization: 42° C. overnight in 50% formamide, 5X SSPE, 5X Denhardts, 0.1% SDS, 200 µg/ml salmon sperm DNA, and 32P-labeled probe ($1 \times 10^6$ cpm/ml).

Wash: One wash for 15 min at 42° C. in 2X SSC, 0.1% SDS, then one wash at 42° C. for 15 min in 1X SSC, 0.1% SDS, and then one wash at 60° C. for 15 min in 0.1X SSC, 0.1% SDS.

The screening with the labeled insert was positive for twelve clones containing putative invertase-encoding sequences, and two clones, λPL1 and λPL3, were selected for further characterization. The restriction enzyme maps of these two clones are shown in FIG. 1.

The L. esculentum genomic library was then rescreened by the method described above with the $^{32}$P-labeled, gel-purified 0.84 kb XhoI-HindIII fragment from the 5' end of the pTOM3-L1 insert. Six positive clones were selected for further characterization. Clone λPL6 was determined to encode the largest amount of sequence 5' from the initiation ATG. The restriction map of λPL6 insert DNA is shown in FIG. 1.

C. DNA sequencing

Fragments of the λPL6 insert DNA were subcloned into pGEM-11Zf(−) (Promega Corporation, Madison, Wis.) vector for sequencing as described in Example 4.B. In all cases, approximately 50 ng of gel-purified (1% agarose gel) fragment were ligated to approximately 100 ng of vector digested with the enzyme(s) noted below, and the ligation was transformed into E. coli DH5α cells. White colonies were selected and determined to contain the correct plasmid by visualization of the correctly sized (see below) insert fragments upon digestion with the noted restriction enzymes. The subclones were as follows:

| Insert DNA | Name of subclone |
| --- | --- |
| 2.3 kb BamHI-BglIII | pPI.6BBg2.3 |
| 2.9 kb BglIII-BamHI | pPI.6BgB2.9 |
| 5.3 kb BamHI | pPI.6B5.3 |
| 7.8 kb BamHI | pPI.6B7.8 |
| 4.1 kb BamHI | pPI.6B4.1 |

The subcloned inserts were sequenced by the dideoxynucleotide chain termination method, using Sequenase® (United States Biochemical Corporation, Cleveland, Ohio) and Klenow DNA polymerase and AMV reverse transcriptase from the K/RT kit protocol of Promega Corporation (Madison, Wis.). The sequenced region provided in Sequence I.D. No. 3 is shown by a dotted line in FIG. 1, and includes the promoter and protein encoding regions of the *L. pimpinellifolium* tomato vacuolar invertase gene.

A schematic of the *L. pimpinellifolium* genomic sequence containing the promoter and protein encoding regions (Sequence I.D. No. 5) is shown in FIG. 2. A putative transcription start site is located at nucleotide position 3099. The TATA box is considered to be located at nucleotide positions 3068 through 3071. The translation start site is considered to begin at nucleotide position 3117, and the stop codon begins at nucleotide position 7040. The three nucleotide insertion (TCT), which is not present in the *L. esculentum* cDNA pTOM3-L1 between nucleotides 650 and 651 (Sequence I.D. No. 2, see Example 4.B), is located at nucleotide positions 5306 through 5308 of the genomic sequence. In addition, the 21 bp sequence located at the 3' end of one class of invertase cDNAs but not the other (see Example 4.B) is located at nucleotide positions 7289 through 7309 of the genomic sequence.

EXAMPLE 7

ISOLATION OF *L. ESCULENTUM* INVERTASE GENE PROMOTER SEQUENCES

A. Construction of genomic library

A genomic library was constructed in λ FIX™ II using DNA isolated from seedling tissue of *L. esculentum* cv. UC82 grown by SIBIA from seeds obtained from Hunt-Wesson Foods, Inc. The library construction was conducted according to the procedure described in Example 6.A.

B. Library screening

Plasmid pTOM3 (see Example 4), a clone encoding invertase from the *L. esculentum* fruit cDNA library, was digested with SfiI and NotI, and the 1339 bp insert was excised from a 1% agarose gel and purified. The insert was labeled with $^{32}P$ and used to probe the *L. esculentum* genomic library under the following conditions:

Hybridization: 42° C. overnight in 50% formamide, 5X SSPE, 5X Denhardt's solution, 0.1% SDS, 200 μg/ml salmon sperm DNA, and $^{32}P$-labeled probe (106 cpm/ml);

Wash: One wash at 42° C. for 15 min in 2X SSC, 0.1% SDS, then one wash at 42° C. for 15 min in 1X SSC, 0.1% SDS, and then one wash for 15 min at 60° C. in 0.1X SSC, 0.1% SDS.

Four clones containing putative invertase-encoding sequences were identified, and three were selected for further characterization. The restriction enzyme maps for these clones, λEI.1, λEI.2 and λEI.3 are shown in FIG. 1.

C. DNA sequencing

Fragments of the insert DNAs were subcloned in pGEM-11Zf(−) (Promega Corporation, Madison, Wis.) vector for sequencing as described in Example 6.C. The subclones were as follows:

| Clone | Insert DNA | subclone |
| --- | --- | --- |
| λEI.1 | 5.0 kb BglIII | pEI.1B5.0 |
| λEI.2 | 1.75 kb BglIII-BamHI | pEI.2BB1 |
| λEI.2 | 2.9 kb BamHI-BglIII | pEI.2BB2 |
| λEI.2 | 4.0 kb HindIII** | pEI.2H |
| λEI.3 | 2.2 kb NotI*-BamHI | pEI.3NB2.2 |
| λEI.3 | 3.9 kb NotI*-BglIII | pEI.3NBg3.9 |
| λEI.3 | 7.8 kb BamHI | pEI.3B7.8 |

*Restriction enzyme site is in the vector polylinker
**Insert was ligated into pGEM-5Zf(+) (Promega Corporation, Madison, WI).

The subcloned inserts were sequenced as described in Example 4.C. The sequenced regions provided in Sequence I.D. No. 3 are shown by dotted lines in FIG. 1, and include the promoter and protein-encoding regions of *L. esculentum* tomato vacuolar invertase gene.

Primer extension analysis was carried out by the method of Sambrook et al. [(1989) Molecular Cloning: A Laboratory Manual, Cold Spring Harbor Laboratory Press, Cold Spring Harbor, N.Y., Vol. 1, pp. 7.79–7.83] in order to determine the transcription start site. The oligonucleotide primer used in the primer extension reaction is complementary to nucleotides 74–107 of Sequence I.D. No. 2.

A schematic of the *L. esculentum* genomic sequence containing the promoter and protein-encoding regions (SEQ I.D. No. 3) is shown in FIG. 2. The transcription start site is located at nucleotide position 3099. The TATA box appears to be located at nucleotide positions 3068 through 3071. The translation start site appears to begin at nucleotide position 3117, and the stop codon begins at nucleotide position 7041. The TCT insertion, not present in *L. esculentum* cDNA clone pTOM3-L1, is present in *L. esculentum* genomic clone λEI.3 at nucleotide positions 5307–5309. The 21 bp sequence present in the 3' end of one class of invertase cDNAs, but not the other, is located at nucleotide positions 7289 through 7309 of the genomic sequence.

EXAMPLE 8

PREPARATION OF CONSTRUCTS FOR THE EXPRESSION OF TOMATO INVERTASE

A. *L. pimpinellifolium* invertase promoter/invertase gene constructs

Plasmid pPI.6B7.8 (Example 6.C), a subclone of λP1.6 containing the largest BamHI restriction enzyme fragment (see FIG. 1), was digested with BamHI to obtain the original 7.8 kb insert, and the insert was isolated on a 0.6% agarose gel. Approximately 80 ng of insert were ligated with 80 ng of BamHI-digested pPI.6BgB2.9, another subclone of λP1.6, (see Example 6.C). The ligation mixture was transformed into *E. coli* TB-1 cells (GIBCO BRL, Gaithersburg, Md.), and Amp$^R$ colonies were isolated. The correct plasmid yielded 10.7 kb and 3.3 kb fragments upon digestion with NotI and EcoRI, and was called pPI.6BgB10.7.

Plasmid pPI.6BgB10.7 was digested with EcoRI and BamHI (partial digestion), and the 10.7 kb insert was isolated on a 0.6% agarose gel. Approximately 40 ng of insert DNA were ligated with approximately 200 ng of EcoRI- and BamHI-digested pBIN19 (Clontech, Palo Alto, Calif.), and the ligation mixture was used to transform *E. coli* TB-1 cells. Kan$^R$ colonies were selected, and the correct plasmid was identified by release of 10, 7.8, and 2.9 kb fragments upon digestion with EcoRI and BamHI. The correct plasmid was designated PI.6/BIN and contained the *L. pimpinellifolium* invertase coding region as well as 3.4 kb of upstream and 2.9 kb of downstream sequences.

B. *L. esculentum* invertase promoter/invertase gene constructs

Plasmid pEI.3B7.8 (see Example 7.C) was digested with BamHI, and the 7.8 kb insert was isolated on a 0.6% agarose gel and purified. Approximately 80 ng of DNA insert were ligated to approximately 120 ng of BamHI-digested pEI.2BB2 (see Example 7.C) and the ligation mixture was used to transform *E. coli* TB-1 cells. Amp$^R$ colonies were selected, and the correct plasmid was identified by release of 10.7 and 3.3 kb fragments upon digestion with NotI and EcoRI. The correct plasmid was called pEI.23BgB10.7.

Plasmid pEI.23BgB10.7 was digested with EcoRI and BamHI (partial digestion), to produce a 10.7 kb insert containing the invertase coding sequence and 3.4 kb upstream and 2.9 kb downstream sequence. The 10.7 kb insert was isolated on a 0.6% agarose gel and purified. Approximately 80 ng of insert DNA was ligated to approximately 200 ng of EcoRI- and BamHI-digested pBIN19 (Clontech, Palo Alto, Calif.), and the ligation mixture was used to transform *E. coli* TB-1 cells. Kan$^R$ colonies were selected, and correct plasmid was identified by production of 10, 7.8, and 2.9 kb fragments upon digestion with EcoRI and BamHI. The correct plasmid was designated pEI.23/BIN.

C. *L. esculentum* invertase promoter/GUS gene constructs

Invertase promoter sequences may also be linked to reporter genes, such as the GUS, or β-glucuronidase, gene of *E. coli*. The GUS gene in the present example is obtained from the *E. coli* plasmids identified below.

Sequences in the promoter region of the *L. esculentum* gene between 3 base pairs and either 747, 913, or 1079 base pairs upstream from the initiator ATG from pEI.23BgB10.7 (Example 8.B) were amplified by the polymerase chain reaction (PCR) using the following oligonucleotide primers: primer A (SEQ I.D. No. 13), 5'-CATTCTAGAAGATAGAGGAATG-3', which created an XbaI site 1 bp upstream of the initiator ATG, and primer B (SEQ. I.D. No. 14), 5'-TGAAGCTTAATCAACCTGTAAATCCC-3', located in the region of direct repeats, which created a HindIII site 752 bp, 918 bp, 1084 bp and possibly additional sites upstream of the initiator ATG. These multiple sites are due to the fact that this promoter region contains 5–6 direct repeats of 166 base pairs.

Figure 3B:
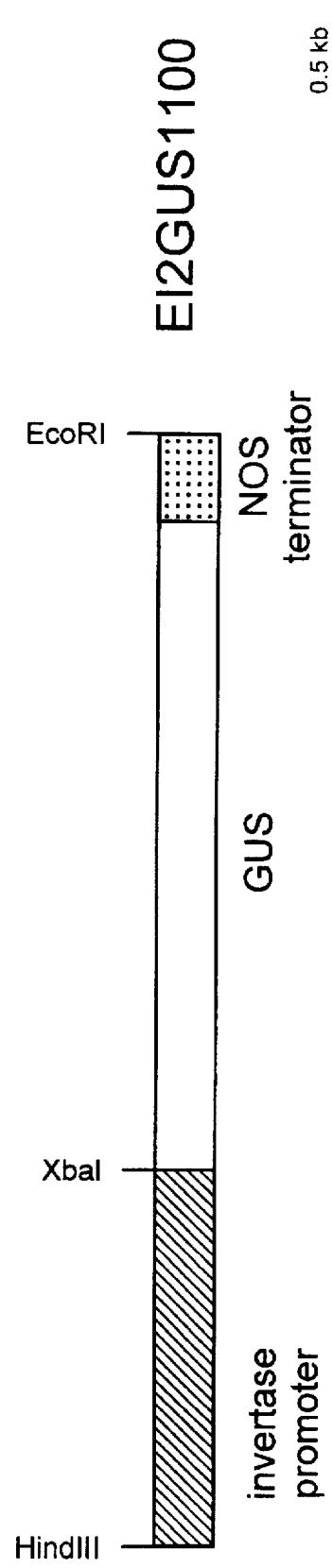

The PCR products were digested with HindIII and XbaI and 40 ng of the digested DNA were ligated with 120 ng of HindIII- and XbaI-digested pBI221 (Clontech, Palo Alto, Calif.) and the ligation mixture was used to transform *E. coli* DH5α cells. Amp$^R$ colonies were selected. One correct plasmid was identified by the production of an approximately 750 bp fragment upon digestion with HindIII and XbaI and was called EI2GUS715 (FIG. 3). A second correct plasmid was identified by production of an approximately 1100 bp fragment upon digestion with HindIII and XbaI and was called EI2GUS1100 (FIG. 3).

Plasmid EI2GUS715 was digested with EcoRI and HindIII, and 100 ng of the 3.1 kb fragment were ligated with 200 ng of EcoRI- and HindIII-digested pBIN19 (Clontech, Palo Alto, Calif.). The ligation mixture was used to transform *E. coli* TB-1 cells, and Kan$^R$ colonies were selected. The correct plasmid was identified by release of a 3.1 kb fragment upon digestion with EcoRI and HindIII and was called EI2GUS715BIN.

The 3.4 kb EcoRI-HindIII fragment of plasmid EI2GUS1100 was ligated into pBIN19 by the same procedure was used for EI2GUS715. The correct plasmid was identified by release of a 3.4 kb fragment upon digestion with EcoRI and HindIII and was called EI2GUS1100BIN.

EXAMPLE 9

TRANSFORMATION OF TOMATO PLANTS WITH INVERTASE PROMOTER CONSTRUCTS

A. Transformation of *L. esculentum* seedlings

The transformation of seedlings of *L. esculentum* cv. UC82 (grown from seeds obtained from Ferry Morse Seed Co., Modesto, Calif.) was done according to the protocol of Fillatti et al. [(1987) *Bio/Technology* 5:726–730], with modifications as described below.

Cotyledons were excised from eight-day-old tomato seedlings germinated in vitro and were cut into three sections. The middle sections with dimensions 0.5 cm×0.25 cm were placed abaxile side up on one-day-preconditioned tobacco feeder plates containing KCMS incubation medium [Murashige and Skoog salt base (Gibco Laboratories, Grand Island, N.Y.) with thiamine-HCl, 1.3 mg/l; 2,4-dichlorophenoxyacetic acid, 0.2 mg/l; kinetin, 0.1 mg/l; monobasic potassium phosphate, 200 mg/l; myo-inositol, 100 mg/l; sucrose, 30 mg/l; tissue culture agar, 8 g/l, pH 5.7] and incubated at 27° C. with 16 hours of light per day.

The tobacco feeder plates were prepared according to the method of Horsch and Jones [(1980) *In Vitro* 16:103–1089, with the following modifications. Cells from a six-day-old tobacco suspension culture were resuspended in fresh MM medium (Murashige and Skoog salt base with thiamine-HCl, 0.1 mg/l; pyridoxine-HCl, 0.5 mg/l; nicotinic acid, 0.5 mg/l; glycine, 2 mg/l; 6-benzylaminopurine, 0.5 mg/l; 2,4-dichlorophenoxyacetic acid, 0.5 mg/l; myo-inositol, 100 mg/l; sucrose, 30 g/l, pH 5.7) to a final density of 0.3 g fresh weight per ml. The suspension were stirred, and 1.5 ml aliquots are pipetted onto KCMS medium (25 ml) solidified with tissue culture agar (0.8% w/v) in 100 mm×20 mm plastic petri plates.

After one day of incubation of tomato cotyledon tissue on the tobacco feeder plates, the explants were floated in 20 ml of Murashige and Skoog liquid medium without hormones containing an overnight culture of *Agrobacterium tumefaciens* strain LBA4404 [Clontech, Palo Alto, Calif.; see also Ooms et al. (1982) *Plasmid* 7:15–19], harboring either plasmid EI2GUS715BIN or EI2GUSUOOBIN, described in Example 8, which were inserted into *A. tumefaciens* through triparental mating.

*A. tumefaciens* strain LBA4404 was maintained at a density of 5×10$^8$ cells/ml. The tissue and Agrobacterium were incubated at room temperature for 30 min, after which time the explants were blotted on sterile Whatman paper No. 1 and transferred to tobacco feeder plates. The cultures were incubated at 27° C. with 16 hr of light per day. After two days of incubation, the treated cotyledon segments were transferred to regeneration 2Z medium (Murashige and Skoog salt base with thiamine-HCl, 1.0 mg/l; pyridoxine-HCl, 0.5 mg/l; nicotinic acid, 0.5 mg/l; glycine, 2 mg/l; zeatin, 2 mg/l; sucrose, 30 g/l; myo-inositol, 100 mg/l; tissue culture agar, 8 g/l, pH 5.7) with 500 µg/ml cefotaxime and 100 µg/ml kanamycin).

The cultures are being incubated at 27° C. with 16 hours of light per day under 4,000 lux of light intensity. When kanamycin-resistant shoots reach a height of one inch, they will be rooted on rooting medium, which is identical to regeneration 2Z medium except that it lacks hormones and contains 250 µg/ml cefotaxime and 50 µg/ml kanamycin. The transgenic shoots will then be grown into fruit-bearing transgenic tomato plants.

B. Assays for Recombinant Gene Expression

Since the promoter sequences are developmentally regulated and fruit-specific, tomato fruit tissues are assayed for invertase or GUS expression at various stages of fruit development. Invertase activity is determined according to the assay described in Example 1. GUS activity is determined according to the following protocol.

200–300 mg of tissue is homogenized in 200–300 µl of GUS extraction buffer [Jefferson (1987) *Plant Mol. Biol. Rep.* 5:387–405). Another 150 µl of GUS extraction buffer is added, and the tissue is frozen in liquid nitrogen, then thawed at room temperature. This procedure is repeated, and the tissue slurry is centrifuged in a microfuge at 4° C. for 10 minutes. Tissue extracts (100 µl) are incubated with 0.6 ml of MUG buffer containing 20% methanol according to the procedure of Jefferson [(1987) *Plant Mol. Biol. Rep.* 5:387–405] to determine GUS activity. Briefly, the assay for GUS activity is a fluorometric assay which measures the production of 4-methyl umbelliferyl from 4-methyl umbelliferyl glucuronide (MUG), a fluorogenic substrate. Protein concentration is determined according to the Protein Assay using reagents obtained from Bio-Rad (Richmond, Calif.).

EXAMPLE 10

CONSTRUCTION OF HDC PROMOTER CONSTRUCTS

A. Isolation of a developmentally regulated gene

1. Construction of cDNA library a. Isolation of RNA

Tomato fruit at the 3-inch intermediate stage was collected from greenhouse-grown *L. esculentum* cv. UC82 (grown from seeds obtained from Hunt-Wesson Foods, Fullerton, Calif.), rinsed in $H_2O$, blotted dry, cut into 6–8 pieces, and frozen in liquid nitrogen. To facilitate chemical extraction, the tissues were pulverized under liquid nitrogen with a mortar and pestle. The skins and seeds were removed from the frozen fruit prior to pulverization.

Ten grams of pulverized frozen *L. esculentum* cv. UC82 tomato tissue from the 3-inch intermediate fruit stage were mixed with 25 ml of buffer (0°–4° C.) and homogenized with a mortar and pestle. The composition of the homogenization buffer was 200 mM Tris-acetate, pH 8.2, 100 mM magnesium acetate, 20 mM potassium acetate, 1% Triton X-100, 5% sucrose, 20 mM EGTA, and 14 mM 2-mercaptoethanol. The crude homogenate was clarified by two ten-minute centrifugations at 15,000× g. The supernatant was layered over a 10 ml sucrose cushion, and the polysomes were pelleted for two hours at 200,000× g. The cushion was made by increasing the sucrose in the homogenization buffer to 40%.

The pellets were resuspended in 0.5 ml of 0.25 M sucrose and added to 4.5 ml of resuspension buffer, which contains 1% SDS in 0.1 M sodium acetate, pH 6.0. This was shaken with 10 ml of phenol equilibrated with resuspension buffer. The aqueous phase was removed and saved, and the residual phenol was shaken with another 5 ml of resuspension buffer. The two aqueous phases were combined and extracted twice with chloroform, then brought to 0.3M with sodium acetate, and precipitated with ethanol. Following ethanol precipitation and in the presence of 3 M sodium acetate, the RNA was pelleted and resuspended in 5 ml of 0.2 M LiCl; 15 ml of absolute ethanol was added, and the mixture was held at –20° C. The RNA was pelleted and resuspended in 500 µl of 0.2 M LiCl, and a 25 µl sample was removed for determination of absorbance. The remaining RNA was brought to 5 ml with 0.2 M LiCl, 15 ml of absolute ethanol was added, and the mixture was held at –20° C. The RNA was pelleted, resuspended to 4 µg/µl in sterile $H_2O$, and stored at –70° C.

Poly(A)+ RNA was selected by affinity chromatography on oligo(dT)-cellulose columns using the procedure of Aviv and Leder [(1972) *Proc. Natl. Acad. Sci. USA* 69:1408–1412], except that LiCl was used instead of NaCl. The poly(A)+ RNA pellet was collected by centrifugation and resuspended to approximately 0.25 µg/µl in sterile $H_2O$, and 4 µl were removed for agarose gel electrophoretic analysis. The remaining RNA solution was brought to 5 ml with 0.2 M LiCl, 10 ml of 95% ethanol was added, and the mixture was held at –20° C. The precipitated RNA was collected by centrifugation and resuspended in 100 µl of sterile $H_2O$ to which was added 50 µl of 7.5 M ammonium acetate plus 300 µl of absolute ethanol; this mixture was held at –20° C.

b. Preparation of cDNA

Ten µg of poly(A)+ RNA were collected by centrifugation and resuspended in 5 µl $H_2O$, brought to a final concentration of 2.7 mM $CH_3HgOH$, and incubated at room temperature for 5 minutes [Payver and Schimke (1979) *J. Biol. Chem.* 254:7636–7642]. The first strand of cDNA was synthesized by incubation of 10 µg of $CH_3HgOH$-treated RNA at 42° C. for 20 minutes in 50 µl of a solution containing 50 mM Tris, pH 8.3, 10 mM $MgCl_2$, 30 mM 2-mercaptoethanol, 70 mM KCl, 500 µM each of dATP, dGTP, and dTTP, 250 µM dCTP, 25 µg/ml oligo(dT), 60 µg/ml actinomycin D, 25 µCi α-$^{32}$P dCTP (32.5 picomoles), and 187.2 units of reverse transcriptase (Molecular Genetic Resources, Tampa, Fla.). The reaction mixture was adjusted to 0.3 N NaOH by the addition of 21.7 µl 11 M NaOH and was held at 65° C. for 30 minutes. Ten µl of 1 M Tris, pH 7.4, were added, and the solution was neutralized by the addition of 21.7 µl 11 M HCl.

Following phenol-chloroform-isoamyl alcohol extraction and chloroform-isoamyl alcohol extraction, the cDNA was passed over a Sephadex G50 column in TE buffer (pH 7.4). The pooled cDNA fraction was dried under vacuum, resuspended in 50 µl of TE buffer, brought to 2.5 M ammonium acetate by the addition of 25 µl of 7.5 M ammonium acetate, and precipitated at –70° C. overnight by the addition of two volumes of ethanol. The precipitate was collected by centrifugation in a microfuge for 15 minutes at room temperature and resuspended in 50 µl of TE buffer. The ethanol precipitation was repeated, and the cDNA precipitate was resuspended in 20 µl of $H_2O$.

The cDNA molecules were made double-stranded by incubating in a volume of 50 µl containing 50 mM $KPO_4$, pH 7.4, 5 mM $MgCl_2$, 1 mM 2-mercaptoethanol, 250 µM each dATP, dGTP, and dTTP, 200 µM dCTP, 25 µCi α-$^{32}$P-dCTP and 11 units of DNA polymerase I, Klenow fragment (New England BioLabs, Beverly, Mass.) at 37° C. for one hour. The reaction was stopped by the addition of 2 µl of 0.5 M EDTA, phenol-chloroform-isoamyl alcohol extracted, chloroform-isoamyl alcohol extracted, and passed over a Sephadex G50 column. The pooled fractions were reduced to 75 µl under vacuum, and the DNA was ethanol precipitated twice as described above.

To insure completion of the second strand synthesis, the DNA molecules were incubated at 42° C. for 15 minutes in a 50 µl solution containing 50 mM Tris, pH 8.3, 10 mM $MgCl_2$, 30 mM 2-mercaptoethanol, 70 mM KCl, 500 µM each of dATP, dCTP, dGTP and dTTP, and 150 units of reverse transcriptase (Molecular Genetic Resources, Tampa, Fla.). The reaction was stopped by the addition of 2 µl of 0.5 M EDTA, and the DNA products were processed as described above.

Following ethanol precipitation, the double-stranded molecules were resuspended in 44 µl of $H_2O$ and digested with 1000 units of S1 nuclease (Boehringer Mannheim Biochemicals, Indianapolis, Ind.) at 22° C. for 30 minutes in a reaction volume of 50 µl containing 280 mM NaCl, 20 mM sodium acetate, pH 4.5, and 4.5 mM ZnSO$_4$. The reaction was stopped by the addition of 2 µl of 0.5 M EDTA, and the DNA products were processed as described above. Following ethanol precipitation, the DNA precipitate was resuspended in TE buffer and ethanol precipitated again. The blunt-ended molecules were then resuspended in H$_2$O and tailed with d(C) in a reaction volume of 50 µl containing 10 µl of 5× terminal transferase buffer (Bethesda Research Laboratories, Inc., Rockville, Md.), 10 picomoles of α-$^{32}$P-dCTP, 2.0 µM of dCTP, and 21 units of terminal transferase (Ratliff Biochemicals, Los Alamos, N.M.) at 37° C. for 30 minutes. The reaction was stopped by the addition of 2 µl of 0.5 M EDTA, and the DNA products were processed as described above except that, following Sephadex G50 chromatography, the volume of the pooled products was reduced by n-butanol extraction. Following two ethanol precipitations, the DNA was resuspended in 20 µl of TE.

c. Construction of cDNA library

The tailed DNAs were annealed to pBR322 DNA which had been digested at the PstI site and tailed with d(G) (New England Nuclear, Boston, Mass.). The volume of the annealing mixture was 500 µl and contained 10 mM Tris, pH 7.4, 0.1M NaCl, 0.001M EDTA, 1 µg of double-stranded, d(C)-tailed insert DNA and 1.25 µg of d(G)-tailed pBR322 DNA. The mixture was incubated at 65° C. for 3 minutes, then at 42° C. for 2 hours and slowly cooled to room temperature.

The recombinant plasmid DNA molecules were used to transform LE392 *E. coli* cells which were then plated on LB-tetracycline (15 µg/ml) plates. The resultant cDNA library was stored by the procedure of Hanahan and Meselson [(1980) *Gene* 10:63–67].

2. Library screening

The cDNA library was screened to identify clones containing insert sequences which were expressed either constitutively or under developmental regulation. To achieve this, "early" and "late" stage RNA probes were prepared, labeled in a polynucleotide kinase reaction, and hybridized with the filter-bound DNAs.

a. Preparation of probes

Twelve grams each of 1-inch green and 3-inch intermediate *L. esculentum* cv. UC82 fruit were pulverized in the presence of liquid nitrogen, then divided into four 3-gram samples. Five ml of 0.1 M Tris-HCl, pH 9.0, and 5 ml of phenol which had been pre- equilibrated with the same Tris solution was added to each sample. Immediately upon addition of these solutions, each sample was homogenized for five seconds with a Brinkmann polytron; this homogenization was repeated four more times. Following homogenization, samples were centrifuged in an IEC centrifuge for 15 minutes at 3500 rpm. The aqueous phase was removed and retained. The phenol layer was mixed with an additional 5 ml of 0.1 M Tris-HCl, pH 9.0, and centrifuged in an IEC centrifuge for 15 minutes at 3500 rpm. The resultant aqueous layers from these extractions were combined, extracted three times with equal volumes of chloroform, and brought to 0.3M with 3M sodium acetate, pH 5.2. Two volumes of absolute ethanol were added, and the mixtures were held at −20° C.

The precipitated RNA was collected by centrifugation at 0°–5° C. for 30 minutes in a Sorvall centrifuge at 10,000 rpm in siliconized Corex™ tubes. Each pellet was resuspended in 9.4 ml of sterile H$_2$O, 3.1 ml of 8 M LiCl was added, and the mixtures were held at −20° C. overnight. RNA pellets were collected by centrifugation at 0°–5° C. for 30 minutes at 10,000 rpm and resuspended in 1 ml of sterile H$_2$O. Ten µl of each preparation were removed for determination of absorbance, and each remaining sample was brought to 3 ml with sterile H$_2$O, 75 µl of 8 M LiCl was added, and, following addition of 7 ml of absolute ethanol, the mixtures were held at −20° C. overnight.

Total RNAs from both 1" green and 3" intermediate fruit were subjected to oligo-dT cellulose chromatography for the selection of poly(A)+ RNA essentially as described by Aviv and Leder [(1972) *Proc. Natl. Acad. Sci. USA* 69:1408–1412], but using LiCl for the binding instead of NaCl.

Poly(A)+ RNA prepared from early and late stages of *L. esculentum* cv. UC82 tomato fruit development (1-inch green and 3-inch intermediate) was fractionated on a 5–20% sucrose gradient to facilitate enrichment and identification of mRNAs encoding proteins ranging in size from 30 to 60 kilodaltons. Linear sucrose gradients, 5–20% sucrose, were prepared in 100 mM NaCl, 10 mM sodium acetate, 1 mM EDTA, pH 5.0, in sterile polyallomer tubes. Fifty micrograms of poly(A)+ RNA were loaded on each gradient in a total volume of 200 µl and subjected to centrifugation at 39,000 rpm in a Beckman SW41 rotor for 10 hours at 5° C. Using a Gilson pump set at 1 ml/minute, approximately 0.5 ml fractions were collected. From each fraction, 1.5 µl were removed for in vitro translation. To each remaining fraction was added 16.67 µl of 3M sodium acetate, pH 5.2, and one ml of absolute ethanol; RNA was precipitated at −20° C. overnight. The approximate size of poly(A)+ RNAs was estimated from the mobility of ribosomal RNAs fractionated in sucrose gradients run in parallel with the gradients containing the poly(A)+ RNAs. Samples of RNA from gradient fractions were translated in an mRNA-dependent rabbit reticulocyte translation system by the method of Pelham and Jackson [(1976) *Eur. J. Biochem.* 67:247–256]. The lysate and reaction conditions were as provided by New England Nuclear (Boston, Mass.; October 1979 Manual) to produce peptides labeled with L-($^{35}$S)-methionine. Protein synthesis was assayed by determining the incorporation of TCA-precipitable label [Pelham and Jackson (1976) *Eur. J. Biochem.* 67:247–256]. The translation products were then subjected to electrophoresis on a 12.5% SDS acrylamide gel [Laemmli (1970) *Nature* 227:680–685] and fluorography.

b. Library screening

Replica filters were prepared and the plasmids amplified [Hanahan and Meselson (1980) *Gene* 10:63–67] using 200 µg/ml chloramphenicol. DNA from cDNA clones was denatured, neutralized, and fixed to 150 mm nitrocellulose filters [Maniatis et al. (1982) *Molecular Cloning: A Laboratory Manual*, Cold Spring Harbor Laboratory Press, Cold Spring Harbor, N.Y.]. The filters were baked at 70° C. for two hours and stored at room temperature prior to prehybridization.

RNAs from a gradient fraction of one-inch green (early) RNA encoding proteins with a molecular mass of approximately 30–60 kDa and from a similar gradient fraction of three-inch intermediate (late) RNA were labeled with $^{32}$P in a polynucleotide kinase reaction. In brief, approximately 500 nanogres each of a selected fraction of "early" or "late" poly(A)+ RNA was precipitated under ethanol, collected and resuspended in sterile H$_2$O, and then dried under vacuum in 1.5 ml microfuge tubes. Each sample was hydrolyzed by resuspending in 10 µl of 0.1 M Na$_2$B$_4$O$_7$ and incubating for 45 minutes at 65° C. This incubation was stopped by chilling on ice and adding 2.5 µl of 0.5 M EDTA; approximately 100 picomoles of α-$^{32}$P-ATP was then added, followed by the addition of 8 μl of a solution of 20 mM MgCl$_2$ and 20 mM DTT. Four units of polynucleotide kinase (Boehringer-Mannheim, Milwaukee, Wis.; at 8 units/μl) were added, and the incubation was continued at 37° C. for 90 minutes. The reaction was stopped by chilling on ice and by adding 2.5 ml of 0.5 M EDTA. Ten μl of *E. coli* tRNA (at 1 mg/ml) were added as carrier, and the mixture was subjected to chromatography on a Sephadex G-50 column. The labeled RNA was eluted with 0.2M NaCl, 0.1% SDS, 10 mM Tris-HCl, pH 7.4, 1 mM EDTA, and approximately 0.5 ml fractions were collected. All fractions were held at 4° C. prior to identification and pooling of the labeled RNAs.

These labeled fruit RNAs were then hybridized to approximately 10,000 cDNA clones (a fraction of the complete cDNA library) bound to nitrocellulose filters as described above. Following hybridization at 65° C. for 18 hours, the filters were washed, dried, and subjected to autoradiography. Of 313 clones which yielded strong hybridization signals, 36% contained insert sequences which appeared to be expressed differentially at the two different stages of development.

3. Identification of clone ptomUC82-3 as encoding a developmentally regulated sequence Clones which yielded strong hybridization signals in the above-described hybridization experiments were used to prepare plasmid DNA which was then used to probe Northern blots of "early" and "late" fruit RNAs. Plasmid DNA was prepared from clones yielding strong hybridization signals and plasmid DNA was labeled with $^{32}$P by nick translation.

Total RNA was prepared from 1" green and 3" intermediate developmental stages of UC82 fruit as described above. RNA blots were prepared essentially as described by [Thomas (1980]. Ten μg of total RNA were heated at 65° C. for 5 minutes in 10 mM NAPO$_4$, pH 7.4, 50% formamide, 2.2M formaldehyde, and 0.5 mM EDTA. This solution was cooled to room temperature and an appropriate amount of 5X sample buffer (0.5% SDS, 0.025% bromophenol blue, 25% glycerol, 24 mM EDTA) was added. The samples were loaded on a 1.5% agarose gel prepared in 1.1M formaldehyde, 10 mM NaPO$_4$, pH 7.4, and electrophoresed in the same buffer. The gel was stained with acridine orange (33 μg/ml) in 10 mM NaPO$_4$, pH 7.4, and destained in the same buffer. The gel was soaked in 10X SSPE (1X SSPE =180 mM NaCl, 10 mM NaH$_2$PO$_4$, 8 mM NaOH, 1 mM EDTA, adjusted to pH 7.0 with NaOH). The RNA was transferred to a nitrocellulose filter. This filter was then cut into separate panels and hybridized with $^{32}$-labeled insert DNA from cDNA clones ptomUC82-2, ptomUC82-3, ptomUC82-6, ptomUC82-9, ptomUC82-10, and ptomUC82-22. After a 4 day exposure with an intensification screen, the autoradiographic patterns of hybridization indicated that clone ptomUC82-3 encodes a developmentally regulated, fruit-specific sequence which hybridized to a single RNA band with an apparent mobility of ~1.7 kb on a 1.5% agarose gel. These northern hybridization data, as well as hybridization/selection analyses, indicated that cDNA clone ptomUC82-3 corresponds to a gene which is expressed at low levels at early stages of fruit ripening, high levels at intermediate fruit ripening stages, and decreased levels in fully ripened fruit. The insert in ptomUC82-3 was restriction-enzyme mapped and sequenced by the dideoxynucleotide chain termination method and was determined to be a less than full length cDNA clone. However, this clone did contain an ATG start codon.

B. ISOLATION OF TOMATO HDC PROMOTER
1. Construction of genomic library

A genomic library was constructed in λ FIX$^{TM}$II (Stratagene, La Jolla, Calif.) using DNA isolated from seedling tissue of *L. esculentum* cv. UC82. The λ FIX$^{TM}$II vector accommodates inserts of 9 to 23 kb in size, with the T3 and T7 promoters flanking the insert, which can be excised by digestion with NotI.

High molecular weight genomic DNA was prepared from leaves and stems of seedlings of *L. esculentum* cv. UC82 by the CTAB procedure of Rogers and Bendich [(1988) *Plant Molecular Biology Manual*, pp. A6/1–10]. The genomic DNA was digested with Sau3AI such that the majority of the fragments were between 9 and 23 kb in size. The Sau3AI ends were partially filled in using dATP and dGTP. The λ FIX$^{TM}$II vector was digested with XhoI, and the overhang was partially filled in with dTTP and dCTP. This treatment resulted in the production of genomic DNA fragments which could ligate only with the vector overhang and eliminated the possibility of multiple DNA inserts in a single clone.

0.43 μg of genomic DNA was ligated with 1 μg of vector. The ligation reaction was packaged using Stratagene Gigapack$^{TM}$ II Gold packaging extracts (Stratagene, La Jolla, Calif.) and titered on *E. coli* strain LE392. This library had a titer of 2×10$^6$ p.f.u./ml.

2. Library screening

The genomic library was screened with a $^{32}$P-labeled probe prepared from the 800 bp insert purified from cDNA ptomUC82-3 following digestion with PstI. The screening conditions were identical to those described above in Example 4. The screening resulted in the identification and plaque-purification of 13 clones which hybridized to the insert.

C. Isolation of HDC Promoters

Figure 4:
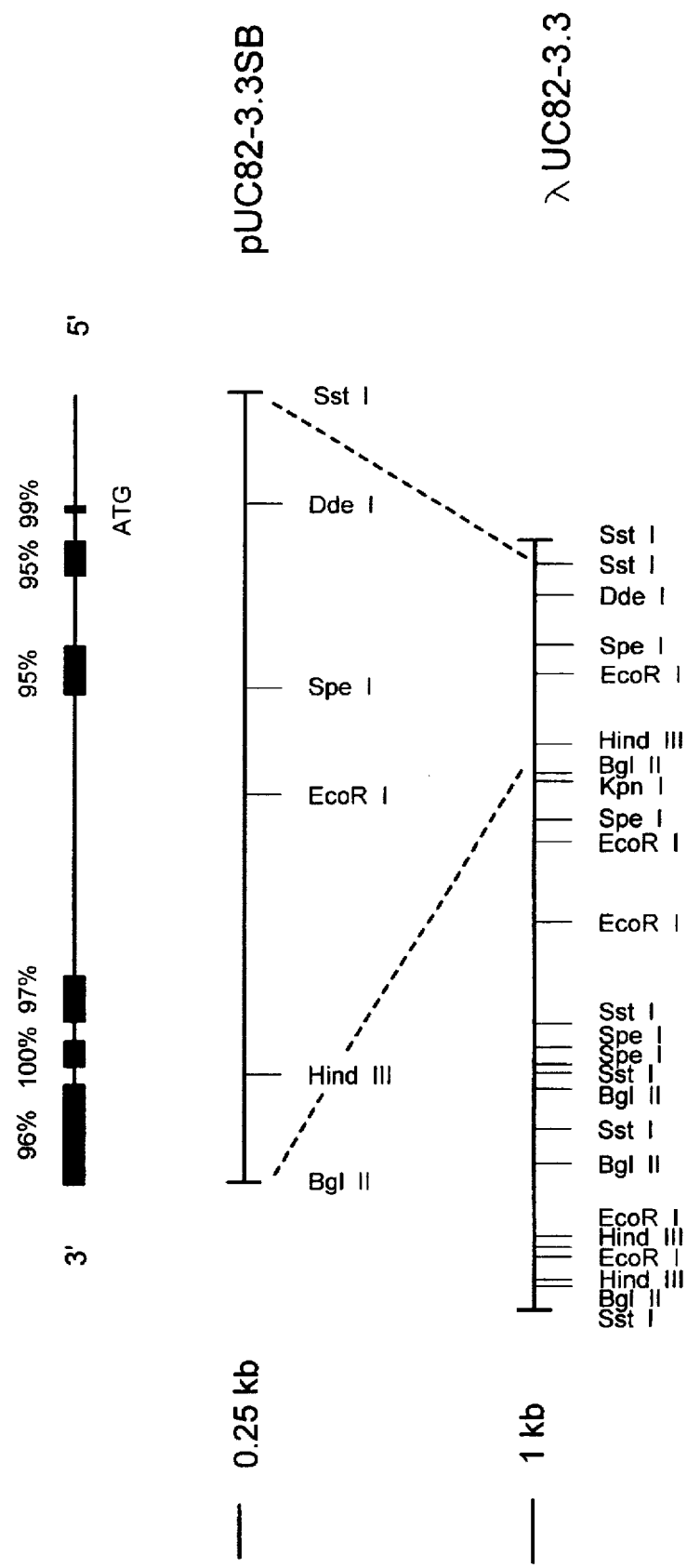
FIG. 4 presents restriction enzyme maps illustrating the derivation of the pUC82-3.3SB insert from the insert of λUC82-3.3. At the bottom of the figure is a schematic diagram of the nucleotide sequence of pUC82-3.3SB, with exons indicated by filled boxes. The percent sequence similarity between this genomic sequence and the HDC-like coding sequence is indicated below each exon.

One of the clones isolated from the genomic DNA library, λUC82-3.3, containing nucleic acids 1–4032 of Sequence I.D. No. 4., was shown by restriction enzyme mapping to contain upstream regulatory regions. A 3.7 kb SstI-BglII fragment from the 5' end of this clone was isolated on a 0.6% agarose gel and purified. This fragment was ligated into pUC119 [Vieira and Messing (1987) In *Methods in Enzymology*, R. Wu and L. Grossman, eds., Vol. 153, pp. 3–11, Academic Press, N.Y.] which had been digested with SstI and BamHI, isolated on a 0.6% agarose gel, and purified. The ligation mixture was used to transform *E. coli* DH5α cells, and Amp$^R$ colonies were selected. The correct plasmid yielded 3.5 and 3.2 kb fragments upon digestion with PstI and SstI and was called pUC82-3.3SB (see FIG. 4). The insert of this subclone was then sequenced completely. This subclone contains six exons that have 95–100% identity with positions 117–302 and 321–1336 of cDNA ptomUC82-3, and appears to include a promoter region.

In order to obtain the remaining 347 bp upstream from the SstI restriction site near the 5' end of the λUC82-3.3 insert, a 3.4 kb restriction enzyme fragment was isolated from λUC82-3.3. This fragment extends from the NotI site in the vector polylinker to the first HindIII site from the 5' end of the XUC82-3.3 insert. This fragment was ligated into 1% agarose gel-purified NotI- and HindIII-digested pGEM-11Zf (−) (Promega Corporation, Madison, Wis.). The ligation mixture was used to transform *E. coli* DH5α cells, and Amp$^R$ colonies were selected. The correct plasmid yielded 3.5 and 3.2 kb fragments upon digestion with Not I and HindIII and was called pUC82-3.3NH. This subclone was then sequenced from the 5' end of the insert to the SstI site, at which point the pUC82-3.3SB sequence begins.

The results of a sequence similarity search through the GenBank database release 67.0 and EMBL database release 26.0 [Devereaux et al. (1984) *Nucl. Acids Res.* 12:387–395] indicate a 60% similarity between the amino acid sequences predicted from cDNA clone ptomUC82-3 and the *Morganella morganii* bacterial histidine decarboxylase gene. Thus, the *L. esculentum* gene identified by hybridization to the cDNA clone ptomUC82-3 probe appears to be a histidine decarboxylase (HDC) gene.

The promoter-containing region, nucleotides 1–888 of Sequence I.D. No. 4, is herein referred to as the HDC promoter.

D. HDC-Promoter/Tomato Fruit Invertase Constructs

1. HDC/3-L1.1

Figures 5A, 5B, 5C:
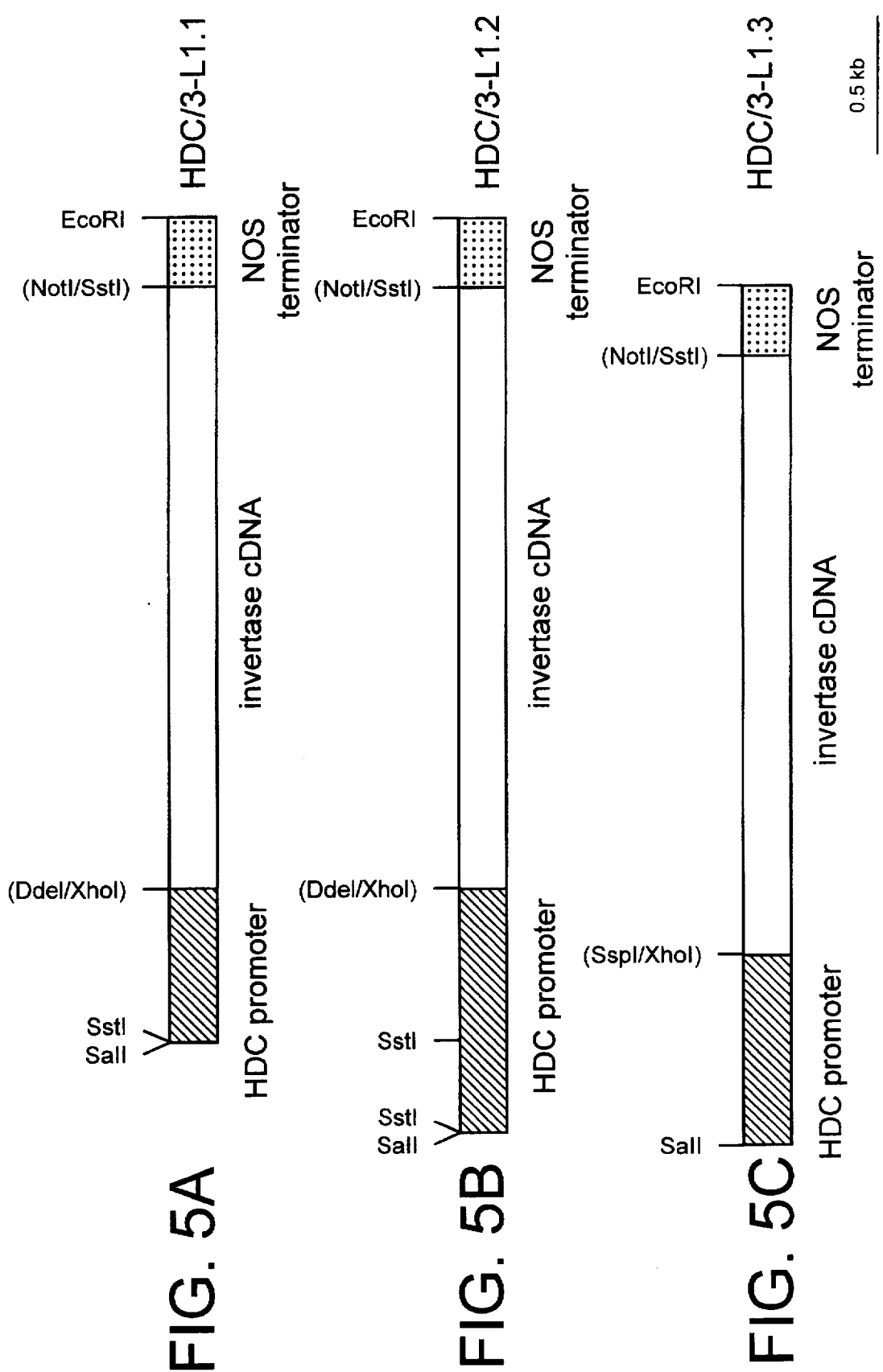
FIGS. 5A–C present diagrams illustrating the composition of constructs HDC/3-Li.1, HDC/3-L1.2, and HDC/3-L1.3.

Construct HDC/3-L1.1 contains 538 bp of the HDC promoter region from λUC82-3.3 (nucleotides 349 to 886 of Sequence I.D. No. 4) fused to the *L. esculentum* cv. UC82 invertase cDNA pTOM3-L1 insert (nucleotides 1 to 2196 of Sequence I.D. No. 2), which is fused at the 3' end to the NOS (nopaline synthase) terminator, as shown in FIG. 5.

pUC82-3.3SB was digested with SpeI and BglII, blunt-ended and the larger fragment was religated. The resulting plasmid, pUC82-3.3SpS, was then digested with DdeI, made blunt-ended with T4 DNA polymerase, and digested with SstI. The resulting 538 bp fragment of the HDC promoter, consisting of nucleotides 349 to 886 of Sequence I.D. No. 4, was gel-purified.

pTOM3-L1 was digested with XhoI, made blunt-ended with T4 DNA polymerase, then digested with NotI. The resulting 2199 bp fragment containing 3 nucleotides from the vector polylinker (AGC) plus the complete *L. esculentum* cv. UC82 invertase cDNA coding sequence (nucleotides 1 to 2196 of Sequence I.D. No. 2) was gel purified.

The fragments prepared from pTOM3-L1 and pUC82-3.3SpS were ligated together with pGEM-11Zf(-) (Promega Corporation, Madison, Wis.) that had been gel purified after digestion with NotI and SstI. The ligation was transformed into *E. coli* DH5= cells and Amp$^R$ colonies were selected. The correct plasmid yielded 3200, 1380, 896, and 460 bp fragments upon digestion with SstI and HindIII and was called -540/3-L1.

The NOS terminator is contained in plasmid pBI101 (Clontech, Palo Alto, Calif.). Plasmid pBI101 was digested with SstI, made blunt-ended with T4 DNA polymerase, digested with SalI, and the resultant approximately 10 kb vector fragment was isolated on a 0.7% agarose gel and purified. The purified vector fragment was ligated to the DNA insert of -540/3-L1 which had been prepared by digestion with NotI, made blunt-ended with T4 DNA polymerase, and digested with SalI. The ligation was used to transform *E. coli* DH5α cells, and Kan$^R$ colonies were selected. The correct plasmid yielded 10 kb, 4kb, and 436 bp fragments upon digestion with EcoRI and Bsu36I and was called HDC/3-L1.1

2. HDC/3-L1.2

Construct HDC/3-L1.2 contains 885 bp of the HDC promoter region from λUC82-3.3 (nucleotides 1 to 886 of Sequence I.D. No. 4) fused to the tomato invertase gene (nucleotides 1 to 2196 of Sequence I.D. No. 2), which is fused at the 3' end to the NOS (hopaline synthase) terminator, as shown in FIG. 5.

Plasmid pUC82-3.3NH was digested with SstI, which cuts in the polylinker and at position 353 of Sequence I.D. No. 4 to release a 360 bp SstI fragment, which was isolated on a 1% agarose gel and purified. The SstI fragment was ligated with SstI-digested plasmid -540/3-L1, the ligation mixture was used to transform *E. coli* DH5α cells, and Amp$^R$ colonies were selected. The correct plasmid yielded 1,385 and 4,500 bp fragments upon digestion with NcoI and SalI and was designated -885/3-L1.

The 3.080 bp SalI-NotI fragment of -885/3-L1 was ligated to pBI101 which had been digested with SstI, made blunt-ended with T4 DNA polymerase, digested with SalI, and gel-purified. The ligation mixture was used to transform *E. coli* DH5α cells, and Kan$^R$ colonies were selected. The correct plasmid yielded 10 kb, 1.7 kb, 1.2 kb, and 460 bp fragments upon digestion with EcoRI and HindIII and was called HDC/3-L1.2.

3. HDC/3-L1.3

Construct HDC/3-L1.3 contains 690 bp of the HDC promoter region from λUC82-3.3 (nucleotides 1 to 690 of Sequence I.D. No. 4) fused to the *L. esculentum* cv. UC82 invertase cDNA (nucleotides 1 to 2196 of Sequence I.D. No. 2) which is fused at the 3' end to the NOS (hopaline synthase) terminator, as shown in FIG. 5.

Plasmid pUC82-3.3NH was digested with SalI and SspI; the SalI site is present in the polylinker. The resultant 700 bp fragment was isolated on a 1% agarose gel and purified.

Plasmid pTOM3-L1 was digested with XhoI, treated with T4 DNA polymerase, and digested with NotI. The resultant 2199 bp fragment (described in section C.1 of this Example) was isolated on a 0.7% agarose gel and purified.

Plasmid pGEM-11Zf(-) (Promega Corporation, Madison, Wis.) was digested with SalI and NotI, and the larger vector fragment was isolated on a 1% agarose gel and purified. A three-way ligation between the fragments prepared from pUC82-3.3NH, pTOM3-L1, and pGEM-11Zf(-) was performed, and the ligation mixture was used to transform *E. coli* DH5α cells. Amp$^R$ colonies were selected, and the correct plasmid was identified by release of 900, 840, 460, 355 and 335 bp fragments upon digestion with SstI and HindIII. The correct plasmid was called -690/3-L1.

Plasmid -690/3-L1 was digested with NotI, made blunt-ended with T4 DNA polymerase, digested with SalI, and the resultant 2886 bp fragment was isolated on a 0.7% agarose gel and purified. The fragment was ligated into gel-purified pBI101 that had been digested with SstI, made blunt-ended with T4 DNA polymerase, and digested with SalI, and the ligation mixture was used to transform *E. coli* DH5α cells. Kan$^R$ colonies were selected, and the correct plasmid was identified by release of 10 kb, 840 bp, 460 bp, 355 bp, and 335 bp fragments upon digestion with HindIII and SstI. The correct plasmid was called HDC/3-L1.3.

E. HDC-promoter/GUS constructs

1. HDC/GUS.1

Construct HDC/GUS.1 contains the promoter fragment from λUC82-3.3 which extends from 794 to 3 bp upstream of the ATG start codon (nucleotides 94 to 886 in Sequence I.D. No. 4) fused to the *E. coli* β-glucuronidase (GUS) gene as shown in FIG. 6.

Plasmid pUC82-3.3NH was digested with DdeI, the ends of the resultant fragment were filled in with Klenow DNA polymerase, and the 792 bp fragment was isolated on a 1% agarose gel and purified. The purified fragment was ligated to HincII-digested pGEM-3Z (Promega Corporation, Madison, Wis.), and the ligation mixture was used to transform *E. coli* DH5α cells. Amp$^R$ colonies were selected, and the correct plasmid was identified by release of a 792 bp fragment upon digestion with EcoRI and HindIII. The correct plasmid was called -790.

Plasmid pBI101.3/pUC was made by inserting the 2200 bp EcoRI-HindIII fragment of pBI101.3 (Clontech, Palo Alto, Calif.) into EcoRI-HindIII-digested pUC119 [Vieira and Messing (1987) In *Methods in Enzymology*, R. Wu and L. Grossman, Eds., Vol. 153, pp. 3–11, Academic Press, N.Y.]. The ligation mixture was used to transform *E. coli* DH5α cells, and Amp$^R$ colonies were selected. The correct plasmid released a 2.2 kb insert upon digestion with HindIII and EcoRI.

Plasmid -790 was digested with HindIII and BamHI, and the 792 bp fragment was isolated on a 1% agarose gel and purified. The 792 bp fragment was ligated to pBI101.3/pUC which had been digested with HindIII and BamHi, and the ligation mixture was used to transform *E. coli* DH5α cells. Amp$^R$ colonies were selected. The correct plasmid released a 2.3 kb fragment upon digestion with SstI and was called -790/GUS.

The 3 kb EcoRI-HindIII fragment containing the HDC promoter-GUS fusion was isolated from -790/GUS and ligated to EcoRI- and HindIII-digested pBIN19 (Clontech, Palo Alto, Calif.). The ligation mixture was used to transform *E. coli* DH5α cells, and Kan$^R$ colonies were selected. The correct plasmid released a 3 kb fragment upon digestion with EcoRI and HindIII and was called HDC/GUS.1.

2. HDC/GUS.2

Construct HDC/GUS.2 contains 690 bp of the HDC promoter region from λUC82-3.3 (nucleotides 1 to 690 of Sequence I.D. No. 4) fused to the *E. coil* GUS gene, as shown in FIG. 6.

Plasmid pUC82-3.3NH was digested with XbaI and SspI, and the 710 bp fragment was isolated on a 1% agarose gel and purified. The fragment was ligated to gel-purified XbaI- and SmaI-digested pBI101.3/pUC, and the ligation mixture was used to transform *E. coli* DH5α cells. Amp$^R$ colonies were selected. The correct plasmid released 3.1 kb and 2.9 kb fragments upon digestion with EcoRI and HindIII and was called -690/GUS.

The 2.9 kb EcoRI-HindIII fragment containing the HDC promoter-GUS fusion was isolated from -690/GUS and ligated to EcoRI- and HindIII-digested pBIN19 (Clontech, Palo Alto, Calif.).

The ligation mixture was used to transform *E. coli* DH5α cells, and Kan$^R$ colonies were selected. The correct plasmid released a 2.9 kb fragment upon digestion with EcoRI and HindIII and was called HDC/GUS.2.

EXAMPLE 11

TRANSFORMATION OF *L. ESCULENTUM* WITH HDC PROMOTER CONSTRUCTS

A. Transformation of *L. esculentum*

The transformation of seedlings grown from *L. esculentum* cv. UC82 seeds was performed by the protocol of Fillatti et al. [(1987) *Bio/Technology* 5:726–730], with modifications as described in Example 9.

B. Analysis For Recombinant Gene Expression

Invertase and GUS expression in the fruit of transformed tomato plants may be assayed as described above in Example 9.

EXAMPLE 12

INVERTASE C-TERMINAL/GUS CONSTRUCTS

Seven amino acids near the C-terminus of tomato fruit vacuolar invertase (amino acids 606 to 612 of Sequence I.D. No. 1) have been identified as having a 85% sequence similarity to the C-terminus of β-1,3-glucanase from *Nicotiana plumbaginifolia*, which is non-homologous to invertase in the rest of its sequence. This 7-amino acid region is presumed to be involved in vacuolar targeting. Two constructs have been assembled using the sequences of proteins which normally are secreted. The first of these constructs (35S/GUS44; see FIG. 7) was assembled to express a fusion protein with the signal sequence from phytohemagglutinin-L (PHA) fused to the amino-terminus of *E. coli* β-glucuronidase (GUS). This plasmid was designed to allow GUS to be targeted to the endoplasmic reticulum and then secreted. The second construct (35S/GUS-INV; see FIG. 7) was prepared to incorporate the C-terminus of tomato fruit vacuolar invertase into GUS and should target GUS to the vacuole.

35S/GUS44 was constructed from plasmid pYE7/PHA44 [Tague et al. (1990) *The Plant Cell* 2:533–546]. Plasmid pYE7/PHA44 contains a PEA-yeast invertase translational fusion. This fusion was cloned as a XhoI fragment into the SalI site of the CaMV35S promoter-octopine synthase (OCS) terminator cassette vector pA35. pA35 is a derivative of pDH51 [Pietrzak et al. (1986) *Nuc. Acid Res.* 14:5857–5868] with a 530 bp CaMV 35S promoter, the multiple cloning site of pUC18, and the octopine synthase (OCS) terminator. The clone with the insert in the proper orientation was designated pA35/PHIN44 [Dickinson et al. (1991) *Plant Physiol.* 95:420–525].

The yeast invertase coding sequence in pA35/PHIN44 was replaced by the GUS coding sequence of plasmid pGUSN358→S (Clontech, Palo Alto, Calif.) by digesting pA35/PHIN44 with SphI and ligating this vector with a SphI-digested fragment derived from PCR amplification of plasmid pGUSN358→S, using SEQ. I.D. NO. 15 5'-GAGCATGCTCCGTCCTGTAG-3,' which anneals to the 5' end of the GUS gene coding sequence, and SEQ. I.D. NO. 16 5'-TTGCATGCCTGCAGTTGTTTGCCTCCCTGCTG-3,' which anneals to the 3' end of the GUS gene coding sequence as primers.

Twenty-nine cycles of denaturation for 30 sec. at 94C., annealing for 30 sec. at 55C., and extension for 3 min. at 72C. were performed with a Perkin Elmer Cetus thermocycler. The resulting 1.8 kb fragment was digested with SphI and ligated into pA35/pHIN44 to produce plasmid 35S/GUS44 shown in FIG. 7. This plasmid contains the following noteworthy features: 1) a cauliflower mosaic virus promoter, CaMV 35S, for high-level expression; 2) the coding sequence for the first 44 amino acids of PHA-L which includes the 20 amino acid signal sequence for efficient translocation across the ER membrane; 3) the GUS reporter protein coding sequence fused in-frame with the PHA sequence and modified by deletion of a glycosylation site that allow GUS to move through secretory system; 4) a unique PstI restriction site which immediately precedes the termination codon of GUS for in-frame C-terminal fusions; and 5) an octopine synthase transcriptional terminator. Upon introduction of this construct into a plant, active GUS which is secreted by the default pathway to the plant cell wall should be produced.

To test the ability of the C-terminus of tomato invertase to target heterologous proteins to the vacuole, the coding sequences for the last 39 amino acids of tomato invertase were fused in-frame to the 3' end of the GUS gene contained in plasmid 35S/GUS44.

First, plasmid 35S/3L-1b was constructed to place the OCS transcriptional terminator after the invertase cDNA sequence and to thereby facilitate subsequent steps. Plasmid pTOM3-L1 was digested with NotI, filled in with Klenow DNA polymerase, digested with XhoI, and the 2.2 kb fragment was gel-purified and cloned into the CaMV 35S promoter/OCS terminator vector pA35. Plasmid pA35 was prepared for this cloning by digesting with SphI, filling-in with Klenow DNA polymerase, and then digesting with SalI. The resulting clone was named 35S/3L-1b and was used for PCR amplification of the 3' end of the invertase sequence.

Figure 7A:
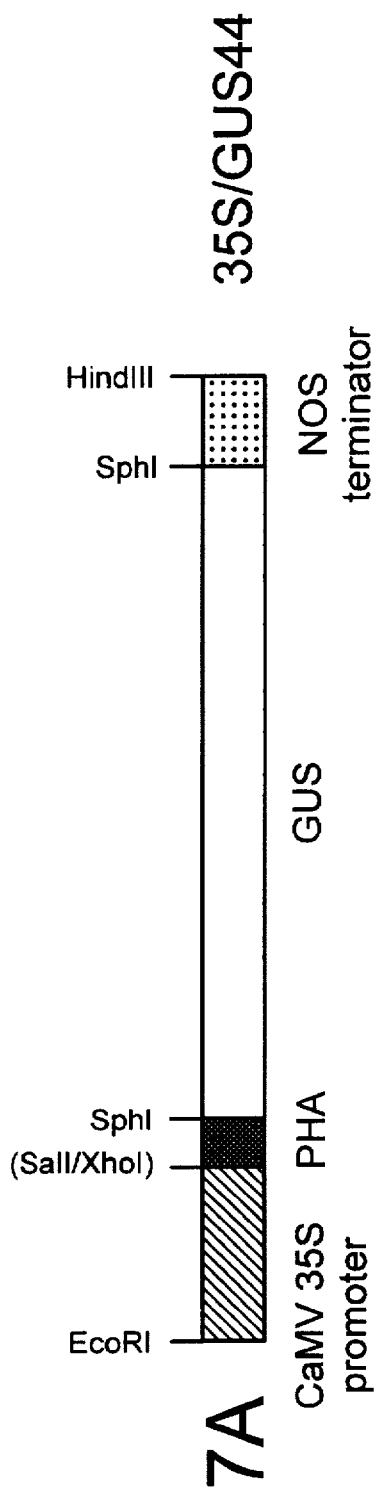
FIGS. 7A and B present diagrams illustrating the composition of constructs 35S/GUS44 and 35S/GUS-INV.
Figure 7B:
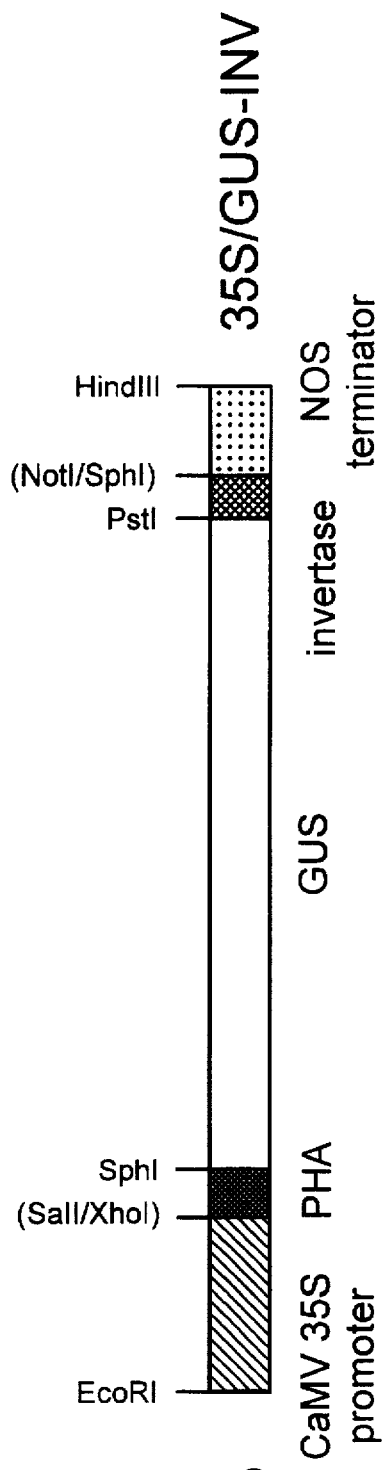

For amplification of a fragment containing the 3' end of the 35S/3L-1b insert, a synthetic oligonucleotide was designed which included a new PstI restriction site to facilitate the in-frame fusion of GUS and invertase sequences. The sequence of one primer was SEQ I.D. No. 17 5'-AACTGCAGAATGGAGCAGCACGACTC. The second primer was the pUC/M13 reverse primer (New England Biolabs, Inc., Beverly, Mass.). Amplification by PCR was conducted according to the procedure of Perkin-Elmer/Cetus (Norwalk, Conn.). The resultant 600 bp fragment was then digested with PstI and HindIII and ligated into 35S/GUS44, which had been digested with PstI and HindIII and gel-purified. The result was plasmid 35S/GUS-INV, as shown in FIG. 7.

These constructs are tranformed into tomato tissue by methods described in the Examples above. The resulting transformed plants are then assayed for GUS activity as described above.

EXAMPLE 13

CaMV 35S PROMOTER/TOMATO FRUIT INVERTASE CONSTRUCTS

A. 35S/3-L1/BIN Overproducing Construct

In order to produce a construct which will allow constitutive overexpression of invertase throughout the plant, the cDNA sequence encoding tomato fruit vacuolar invertase (nucleotides 1–2196 of Sequence I.D. No. 2) was inserted between the CaMV 35S promoter and the nopaline synthase (NOS) terminator in vector pCAMVCN (Pharmacia LKB Biotechnology, Piscataway, N.J.). Plasmid pCAMVCN was digested with PstI, blunt-ended with T4 DNA polymerase, gel-purified, and ligated with the gel-purified 2199 bp XhoI-NotI fragment of pTOM3-L1, which was also made blunt-ended with T4 polymerase. The resulting clone, named 35S/3-L1 (FIG. 8), was ligated into pBIN19 [Bevan (1984) *Nucleic Acids Res.* 12:8711–8721] as a cassette fragment containing the CaMV 35S promoter, the invertase cDNA sequence, and the NOS terminator. (pBIN19 was obtained from Dr. Michael Bevan, Plant Breeding Institute, Cambridge, U.K. but may also be purchased from Clontech, Palo Alto, Calif.) This subcloning was performed by digesting 35S/3-L1 at the 3' end with BglII and at the 5' end with a partial XbaI digestion. A partial XbaI digestion was required due to the presence of an internal XbaI site in the invertase coding sequence contained in pTOM3-L1. The 3.0 kb fragment was gel-purified and ligated into pBIN19 prepared by digestion with XbaI and BamHI. The ligation mixture was used to transform in *E. coli* DH5α cells, and Kan$^R$ colonies were selected. The correct plasmid released 460, 1150, and 1280 bp fragments upon digestion with EcoRI and HindIII. The resulting construct was named 35S/3-L1/BIN.

B. Antisense Construct 35/3-L1(−)

An antisense invertase construct designed to reduce expression of vacuolar invertase in tomato fruit has been prepared. Upon introduction into and expression in a transgenic plant, this construct should reduce invertase activity and thereby alter the soluble solids content of the tomato fruit compared to the fruit of a non-transgenic plant of the same species.

The vacuolar tomato fruit invertase clone pTOM3-L1 cDNA insert was inserted into in the CaMV 35S promoter/terminator cassette in the reverse orientation to create 35/3-L1(−) (FIG. 8). Plasmid pTOM3-L1 was digested with NotI, filled in with Klenow DNA polymerase, digested with XhoI, and the 2.2 kb fragment was gel-purified and cloned into pA35 prepared by digestion with SmaI and SalI. 35S/3-L1 (−) contains the CaMV 35S promoter fused to an antisense pTOM3-L1 cDNA and the OCS transcriptional terminator. This fusion construct was ligated as an EcoRI-SstI fragment into the corresponding sites of pBIN19. The ligation mixture was transformd into *E. coli* DH5α, and Kan$^R$ colonies were selected. The correct plasmid yielded 460, 1060, 1425, and 2700 bp fragments upon digestion with EcoRI and HindIII and was named 35S/3-L1(−)BIN.

C. Cosuppression Construct 35S/3-L1(P)

An alternative approach to reducing invertase production in plant cells is cosuppression.

A coding segment was removed from 35S/3-L1 to create a construct 35S/3-L1(P) encoding a truncated, nonfunctional protein (FIG. 8). To prepare construct 35S/3-L1(P), 35S/3-L1 was digested with PstI, which digests at two sites (nucleotides 1202 and 1383 in Sequence I.D. No. 2) within the invertase coding region, and religated. This produced a 181 bp deletion, creating a shift in the reading frame after codon 399 in Sequence I.D. No. 2 and the introduction of a stop codon four codons beyond codon 399.

Using the same strategy as described above for 35S/3-L1/BIN, 35S/3-L1(P) was mobilized into pBIN19 as an XbaI fragment (obtained following a partial digestion) to create 35S/3-L1(P)BIN.

Transgenic plants that contain this construct should express reduced levels of invertase compared to a non-transgenic plant of the same species.

Since modifications will be apparent to those of skill in the art, it is intended that this invention be limited only by the scope of the appended claims.

---

That which is claimed is:

1. An isolated substantially pure DNA fragment, comprising a sequence of nucleotides that encodes a tomato vacuolar invertase, wherein said DNA fragment is selected from the group consisting of:

(i) a substantially pure DNA fragment which encodes a tomato vacuolar invertase having the amino acid sequence set forth in SEQ ID NO. 2;

(ii) a substantially pure DNA fragment which encodes for a tomato vacuolar invertase having the amino acid sequence set forth in SEQ. ID. No. 1 or a tomato vacuolar invertase which has an amino acid sequence identical to that of SEQ ID No. 1 except for the presence of an additional leucine between residues 215 and 216;

(iii) a substantially pure cDNA or genomic DNA which encodes for a tomato vacuolar invertase having the amino acid sequence set forth in SEQ ID No. 1 or a tomato vacuolar invertase which has an amino acid sequence identical to that of SEQ ID. No. 1 except for the presence of an additional leucine between resides 215 and 216; and (iv) a cDNA or genomic DNA which hybridizes to the DNA of (i) or (iii) and which encodes for a tomato vacuolar invertase.

2. The DNA fragment of claim 1, wherein the genus and species of said tomato is *Lycopersicon esculentum* or *Lycopersicon pimpinellifolium*.

3. The DNA fragment of claim 2 wherein the sequence of nucleotides that encodes said invertase includes introns.

4. The DNA fragment of claim 2, wherein the sequence of nucleotides that encodes said invertase is cDNA.

5. A substantially pure DNA fragment encoding a tomato fruit invertase, comprising a sequence of nucleotides that encodes the amino acid sequence set forth as residues 1–635 in Sequence ID No. 1.

6. An isolated substantially pure, DNA construct, comprising, in the 5' to 3' direction, a developmentally regulated promoter region operatively linked to DNA encoding a tomato vacuolar invertase, wherein:

the operative linkage is for transcription of the DNA encoding the tomato vacuolar invertase; and the promoter region is selected from the group consisting of the HDL promoter region, the *L. pimpinellifolium* tomato vacuolar invertase promoter region, the *L. pimpinellifolium* tomato vacuolar invertase promoter region and the *L. esculentum* invertase tomato vacuolar invertase promoter region; and the HDL promoter region is selected from the group consisting of nucleotides 1–889 of SEQ ID. No. 4, nucleotides 349–886 of SEQ. ID. No. 4, nucleotides 1–886 of SEQ ID. No. 4, and nucleotides 1–690 of SEQ ID. No. 4.

7. The DNA construct of claim 6, wherein said invertase is encoded by the sequence of nucleotides set forth in Sequence ID No. 2.

8. The DNA construct of claim 6, wherein the promoter region includes the sequence of nucleotides set forth in residues about 1–889 of sequence ID No. 4.

9. The DNA construct of claim 6, wherein the promoter region is the promoter region from the *Lycopersicon pimpinellifollium* or *Lycopersicon esculentum* gene that encodes tomato fruit vacuolar invertase.

10. The DNA construct of claim 6 consisting of nucleotides 349–886 of SEQ ID No. 4 operably linked to nucleotides 1–2916 of SEQ ID No. 2 which is in turn operably linked to a 3' nopaline synthase terminator.

11. An isolated DNA construct, comprising, in the 5' to 3' direction the CaMV 35S promoter operatively linked for transcription to the sequence of nucleotides of claim 1 that encodes said invertase.

12. The DNA construct of claim 8, consisting of a CaMV 35S promoter operably linked to nucleotides 1–2196 of SEQ ID No. 2 which is in turn operably linked to a 3' nopaline synthase terminator.

13. An isolated substantially pure DNA construct, comprising, in the. 5' to 3' direction, a promoter region that is constitutively expressed in a tomato plant operatively linked for transcription to the sequence of nucleotides of claim 1 that encodes said invertase.

14. A DNA construct of claim 6 consisting of nucleotides 1–886 of SEQ ID No. 4 operably linked to nucleotides 1–2196 of SEQ ID No. 2 which is in turn operably linked to a 3' nopaline synthase terminator.

15. A DNA construct of claim 6 consisting of nucleotides 1–690 of SEQ ID No. 4 operably linked to nucleotides 1–2196 of SEQ ID No. 2 which in turn is operably joined to a 3' nopaline synthase terminator.

16. The substantially pure cDNA molecule encoding a tomato fruit invertase set forth in SEQ ID No. 2.

17. A method for obtaining a tomato plant having altered tomato vacuolar invertase expression comprising introducing DNA encoding a tomato vacuolar invertase or a fragment thereof, in the sense or anti-sense orientation into a tomato plant thereby producing a tomato plant having altered tomato vacuolar invertase expression.

* * * * *